United States Patent
Sekiguchi et al.

(10) Patent No.: US 9,107,891 B2
(45) Date of Patent: Aug. 18, 2015

(54) METHOD FOR ALLEVIATING FEAR MEMORY

(75) Inventors: Masayuki Sekiguchi, Tokyo (JP); Daisuke Yamada, Tokyo (JP); Jiro Takeo, Tokyo (JP); Wakako Seki, Tokyo (JP); Keiji Wada, Tokyo (JP)

(73) Assignees: NIPPON SUISAN KAISHA, LTD. (JP); NATIONAL CENTER OF NEUROLOGY AND PSYCHIATRY (JP)

( * ) Notice: Subject to any disclaimer, the term of this patent is extended or adjusted under 35 U.S.C. 154(b) by 0 days.

(21) Appl. No.: 14/129,794

(22) PCT Filed: Jun. 29, 2012

(86) PCT No.: PCT/JP2012/066817
§ 371 (c)(1),
(2), (4) Date: Dec. 27, 2013

(87) PCT Pub. No.: WO2013/002404
PCT Pub. Date: Jan. 3, 2013

(65) Prior Publication Data
US 2014/0121276 A1    May 1, 2014

(30) Foreign Application Priority Data
Jun. 29, 2011  (JP) .................................. 2011-143753

(51) Int. Cl.
| | | |
|---|---|---|
| A01N 65/00 | (2009.01) | |
| A61K 31/202 | (2006.01) | |
| A61K 36/00 | (2006.01) | |
| A23L 1/30 | (2006.01) | |
| A61K 31/557 | (2006.01) | |
| A61K 35/612 | (2015.01) | |
| G01N 33/68 | (2006.01) | |

(52) U.S. Cl.
CPC ............. *A61K 31/202* (2013.01); *A23L 1/3006* (2013.01); *A61K 31/557* (2013.01); *A61K 35/612* (2013.01); *A61K 36/00* (2013.01); *G01N 33/6893* (2013.01); *G01N 33/6896* (2013.01); *A23V 2002/00* (2013.01); *G01N 2800/301* (2013.01)

(58) Field of Classification Search
CPC .................................................. A61K 36/00
USPC ................................................... 424/725
See application file for complete search history.

(56) References Cited

U.S. PATENT DOCUMENTS

| | | |
|---|---|---|
| 2004/0241249 A1 | 12/2004 | Sampalis |
| 2007/0254954 A1 | 11/2007 | Sakakibara et al. |
| 2007/0270493 A1 | 11/2007 | Sakakibara et al. |
| 2009/0061067 A1 | 3/2009 | Tilseth et al. |
| 2011/0189760 A1 | 8/2011 | Yoshikawa et al. |

FOREIGN PATENT DOCUMENTS

| | | |
|---|---|---|
| JP | 7-17855 A | 1/1995 |
| JP | 7-82146 A | 3/1995 |
| JP | 2004-534800 A | 11/2004 |
| JP | 2006-83134 A | 3/2006 |
| JP | 2006-83136 A | 3/2006 |
| JP | 2007-126455 A | 5/2007 |
| JP | 2009-532663 A | 9/2009 |
| JP | 2010-537627 A | 12/2010 |
| WO | 2007/098020 A2 | 8/2007 |
| WO | 2009/027692 A2 | 3/2009 |
| WO | 2010/035750 A1 | 4/2010 |

OTHER PUBLICATIONS

Amano et al., "Heightened Amygdala Long-Term Potentiation in Neurotensin Receptor Type-1 Knockout Mice." Neuropsychopharmacology vol. 33, pp. 3135-3145, 2008.
Chhatwal et al., "Enhancing Cannabinoid Neurotransmission Augments the Extinction of Conditioned Fear." Neuropsychopharmacology vol. 30, pp. 516-524, 2005.
DiMarzo et al., "Dietary krill oil increases docosahexaenoic acid and reduces 2-arachidonoylglycerol but not M-acylethoanolamine levels in the brain of obese Zucker rats." International Dairy Journal vol. 20, pp. 231-235, 2010.
Hamazaki et al., "The Effect of Docasahexaenoic Acid on Aggression in Young Adults." Journal of Clinical Investments vol. 97, pp. 1129-1133, 1996.
He et al., "Improved Spatial Learning Performance of Fat-1 Mice is Associated with Enhanced Neurogenesis and Neuritogenesis by docosahexaenoic Acid." Proc. Nat'l. Acad. Sci., USA vol. 106, pp. 11370-11375, 2009.
Iverson, "Cannabis and the Brain." Brain vol. 126, pp. 1252-1270, 2003.
Kawakita et al., "Docosahexaenoic Acid Promotes Neurogenesis In Vitro and In Vivo" Neuroscience vol. 139, pp. 991-997, 2006.
Kiecolt-Glaser JK, et al., "Depressive symptoms, omega-6: omega-3 fatty Acids, and inflammation in older adults." Psychosomatic Medicine, Apr. 2007, vol. 69, No. 3, p. 217-224.
Kreitzer et al., "Retrograde Inhibition of Presynaptic Calcium Influx by Endogenous Cannabinoids at Excitatory Synapses onto Purkinje Cells." Neuron vol. 29, pp. 717-727, Mar. 2001.

(Continued)

*Primary Examiner* — Michael Meller
(74) *Attorney, Agent, or Firm* — Cantor Colburn LLP

(57) ABSTRACT

The present invention provides new methods of intervention for anxiety associated disorders, in particular, trauma-derived disorders such as PTSD, and therapeutic or prophylactic agents for anxiety associated disorders that can be used as foods, beverages, and dietary supplements, for example, and which contain as an active ingredient n-3 polyunsaturated fatty acids contained in krill oil or fish oil, for example. The present invention further provides methods for alleviating fear memory or methods for preventing its formation by adjusting the proportion of n-3 polyunsaturated fatty acids to n-6 polyunsaturated fatty acids as ingested.

11 Claims, 12 Drawing Sheets

(56) References Cited

OTHER PUBLICATIONS

Zushida et al., "Facilitation of Extinction Learning for Contextual Fear Memory by PEPA: A Potentiator of AMPA Receptors." The Journal of Neuroscience, Jan. 3, 2007, 27(1): 158-166.

Maekawa et al. "Arachidonic Acid Drives Postnatal Neurogenesis and Elicits a Beneficial Effect on Prepulse Inhibition, a Biological Trait of Psychiatric Illnesses." PloS One 4, e5085, 2009.

Matsuoka et al., "Omega-3 Fatty Acids for Secondary Prevention of Posttraumatic Stress Disorder After Accidental Injury." An Open-Label Pilot Study, Journal of Clinical Psychopharmacology, vol. 30, No. 2, pp. 217-219, Apr. 2010.

Matsuoka, "Challenge to the Prevention of Posttraumatic Stress Disorder with Fish Oil." Japanese Journal of Molecular Psychiatry, Apr. 2011, vol. 11, No. 2, pp. 154-156 with English Translation.

McKernan et al., "Fear Conditioning induces a lasting potentiation of synaptic currents in vitro", Letters to Nature, vol. 390, pp. 607-611, 1997.

Sekiguchi, "Conditioned Fear Memory and a Balance of Unsaturated Fatty Acids." Japanese Society of Veterinary Science Gakujutsu Shukai Koen Yoshishu, Mar. 1, 2012, vol. 153rd, p. 153 (IS1-6), with English Translation.

Tiemeier H, et al., "Plasma fatty acid composition and depression are associated in the elderly: the Rotterdam Study", The American Journal of Clinical Nutrition, Jul. 2003, vol. 78, No. 1. p. 40-46.

International Search Report for PCT/JP2012/066817, date of mailing: Jul. 24, 2012, with English translation.

US 9,107,891 B2

METHOD FOR ALLEVIATING FEAR MEMORY

This is the U.S. national stage of application No. PCT/JP2012/066817, filed on 29 Jun. 2012. Priority under 35 U.S.C. §119(a) and 35 U.S.C. §365(b) is claimed from Japanese Application No. 2011-143753, filed 29 Jun. 2011, the disclosure of which is also incorporated herein by reference.

TECHNICAL FIELD

The present invention relates to a method of treating or preventing anxiety associated disorders. In particular, the present invention relates to a method of treating or preventing trauma derived disorders such as posttraumatic stress disorder. The present invention also relates to a method for alleviating fear memory or a method for preventing the formation of fear memory. The present invention further relates to biomarkers for determining the risk of suffering a fear memory associated disorder such as anxiety disorder or mood disorder.

BACKGROUND ART

Humans may sometimes suffer fear or aversive experiences in ordinary human relationships or social life or on account of extraordinary accidents, natural disasters, and the like. An event that has caused a serious effect on the survival of an individual or the environment in which the individual has suffered the effect is encoded as "fear memory" in the cranial nerve circuit; in order for the individual to secure behavioral flexibility, this circuit has to be modified or reconstructed as controlled by experience or time. In humans, a failure of this modification or reconstruction is held to be involved in so-called anxiety associated disorders (Non-Patent Document 1.) Anxiety associated disorders are diseases that cause great pain in the patient and are commonly found in people's ordinary life. According to a large-scale epidemiological study made in the United States of America, the lifetime prevalence of mental diseases is as high as 46% (Non-Patent Document 2), of which 29% is occupied by anxiety associated disorders. A survey involving the general Dutch population found that the odds at which people bear a suicide ideation within three years is 2.3 times as high when they have an anxiety disorder as when they have no anxiety associated disorder, even after adjustment of mental illness other than anxiety disorder as well as social factors such as occupation and marital history, and the figure increases to 3.6 in the case of suicide attempt (Non-Patent Document 3.) In Japan, too, more than 30,000 people have committed suicide annually for the past ten years (Non-Patent Document 4.) Thus, carrying out studies on anxiety associated disorders may well be considered to be one of the most important topics in the discipline of psychiatry.

An intense fear memory that is inflicted on the mind by fear or aversive experience can potentially evoke traumatic memory (trauma.) A disorder in certain social function or mental function may derive from such traumatic memory and it can hamper an individual's social life to pose a problem. Posttraumatic stress disorder (PTSD) is a disease characterized by the occurrence of various stress disorders on account of traumatic memory from having experienced a shocking event and there are diverse possible causes, including disasters such as earthquakes, floods and fires, or manmade disasters such as accidents and wars, as well as crimes such as terrorism and physical abuse. PTSD has characteristic features including persistent symptoms of increased arousal (Non-Patent Document 5.) According to a survey of the World Health Organization, 1.1 to 1.6% of the Japanese population suffer PTSD in their lifetime and the incidence tends to rise in their twenties to early thirties, frequently accompanied by anxiety disorder and depressive state, or addictive diseases such as alcohol or drug abuse, as well as eating disorders. While non-drug therapies such as cognitive behavioral therapy are currently practiced as methods to treat PTSD, a study is being made to evaluate the efficacy of a drug therapy using a selective serotonin re-uptake inhibitor (SSRI) (Non-Patent Document 6.)

The amygdala and the hippocampus which are brain areas are considered to play a major role in the formation of trauma-evoking memory of a fearful experience or an aversive experience (Non-Patent Document 7.) It has been reported that in the hippocampus, neurogenesis is taking place even in mature animals and that neurogenesis is involved in long-term changes in the nature of fear and aversive memories (Non-Patent Document 8.)

Polyunsaturated fatty acids such as docosahexaenoic acid (DHA) and arachidonic acid (AA) have been reported to exhibit an action for modifying the neurogenesis in the hippocampus (Non-Patent Documents 9 to 11) and as regards the amygdala and the hippocampus, it has been further reported that fatty acid derivatives such as endocannabinoid function as a nerve transmission modifier (Non-Patent Document 12.) A report has also been published that the modification of cannabinoid's functions affects the memories of fear and aversion (Non-Patent Document 13.)

A report has been made of the use of n-3 polyunsaturated fatty acids such as docosahexaenoic acid, eicosapentaenoic acid, and α-linolenic acid for the purpose of preventing or treating senile dementia (Patent Documents 1 to 3.) A report has also been made of arachidonic acid intended for preventing or improving the lowering of brain functions (Patent Documents 4 and 5.)

It has recently been reported that in an experiment where obese rats (Zucker rats) were kept on a feed mixed with krill oil, the DHA in the brain's phospholipids increased significantly (Non-Patent Document 14.) Heretofore, several reports have been made of experiments using fish oil containing EPA and DHA. Hamasaki et al. reported that upon ingesting DHA-rich fish oil capsules, the aggressiveness of university students was lowered in comparison with a control group (Non-Patent Document 15.) Recently, Matsuoka et al. reported that the ingestion of DHA/EPA capsules had a preventive effect on the development of PTSD (Non-Patent Document 16.) Further, Waku reported that the cannabinoid receptor is closely involved in higher brain functions and that substances acting on the cannabinoid receptor can potentially be applied in therapeutics for obesity, pain, and other conditions (Non-Patent Document No. 17.)

PRIOR ART LITERATURE

Patent Documents

Patent Document 1: Japanese Unexamined Patent Application Publication No. Hei 7-82146
Patent Document 2: Japanese Unexamined Patent Application Publication No. Hei 7-17855
Patent Document 3: Published Japanese Translation of PCT International Publication for Patent Application No. 2009-532663
Patent Document 4: Japanese Unexamined Patent Application Publication No. 2006-83136

Patent Document 5: Japanese Unexamined Patent Application Publication No. 2006-83134

Non-Patent Documents

Non-Patent Document 1: Saibokogaku (Cell Technology), 30 488-492, 2011
Non-Patent Document 2: Arc. Gen. Psychiatry, 62 593-602, 2005
Non-Patent Document 3: Arc. Gen. Psychiatry, 62 1249-1257, 2005
Non-Patent Document 4: Lancet, 371 2071, 2008
Non-Patent Document 5: Diagnostic and Statistical Manual of Mental Disorders IV TR (DSM-IV-TR)
Non-Patent Document 6: Website of the Ministry of Health, Labour and Welfare, http://www.mhlw.go.jp/kokoro/disease/ptsd.html
Non-Patent Document 7: Annu Rev Neurosci 23 155-184, 2000
Non-Patent Document 8: Cell 139 814-827, 2009
Non-Patent Document 9: Neuroscience 139 991-997, 2006
Non-Patent Document 10: Proc Natl Acad Sci USA 106, 11370-11375, 2009
Non-Patent Document 11: PLoS One 4, e5085, 2009
Non-Patent Document 12: Brain 126 1252-1270, 2003
Non-Patent Document 13: Neuropsychopharmacology 30 516-524, 2005
Non-Patent Document 14: Int Dairy Journal 20 231-235, 2010
Non-Patent Document 15: J Clin Invest 97 1129-1133, 1996
Non-Patent Document 16: J Clin Psychopharmacol 30 217-219, 2010
Non-Patent Document 17: Yakugakuzasshi (Journal of the Pharmaceutical Society of Japan), 126(2), 67-81, 2006
Non-Patent Document 18: Nihonjin no shokuji sesshu kijun (Dietary Reference Intakes for the Japanese (2010 ed.), 77-108, 2010
Non-Patent Document 19: Shishitu eiyougaku (Journal of Lipid Nutrition), 6, 164, 1997
Non-Patent Document 20: J Neurosci 27 158-166, 2007
Non-Patent Document 21: Neuropsychopharmacology 33 3135-3145, 2008
Non-Patent Document 22: Neuron 29 717-727, 2001
Non-Patent Document 23: Nature 390 607-611, 1997

SUMMARY OF INVENTION

Technical Problem

Intensive efforts are being made to study the procedures of intervention for anxiety associated disorders, in particular, trauma derived disorders such as PTSD, but as of today, no satisfactory intervention procedures have been established and a new procedure is needed. There exists a further need to develop a therapeutic or prophylactic agent for anxiety associated disorders that is safer to use and which hence can be used as a food, beverage, dietary supplement, and the like.

The formation of an excessive fear memory is known to lead to an anxiety associated disorder such as PTSD. It is also known that patients with an anxiety associated disorder will concurrently develop a mood disorder at high frequency, so alleviation of fear memory is expected to lead not only to the prevention or treatment of anxiety associated disorders but also to the prevention or treatment of mood disorders. However, no satisfactory procedures of intervention for alleviating fear memory or preventing its formation have been established to date and a new procedure is needed. Moreover, the mechanism of action of such a procedure is desirably elucidated.

Solution to Problem

The present inventors conducted intensive studies with a view to attaining the above-stated object and found that krill oil or fish oil derived lipids mainly composed of n-3 polyunsaturated fatty acids reduced the formation of fear memory to thereby exhibit beneficiary effects on the treatment or prevention of anxiety associated disorders; the present invention has been accomplished on the basis of this finding. To state more specifically, the present inventors found that n-3 polyunsaturated fatty acids derived, for example, from krill oil or fish oil derived lipids had an efficacy for reducing the formation of fear memory under such conditions that the ingestion of n-6 polyunsaturated fatty acids was restricted, namely, ingested in such a way that the weight ratio of n-3 polyunsaturated fatty acids to n-6 polyunsaturated fatty acids was not less than a specified value; the present invention has been accomplished on the basis of this finding. The present inventors also found that the n-3 polyunsaturated fatty acids derived from krill oil or fish oil derived lipids according to the present invention displayed the effect of the present invention by acting on cannabinoid signaling pathways.

According to one aspect of the present invention, there are provided therapeutic or prophylactic agents as recited below under (1) to (8).

(1) A therapeutic or prophylactic agent for anxiety associated disorder comprising krill oil as an active ingredient.
(2) The therapeutic or prophylactic agent as recited in (1) above, wherein the krill oil is one purified via a thermal coagulum of krill.
(3) The therapeutic or prophylactic agent as recited in (1) or (2) above, wherein the hill oil has a phospholipid content of at least 30 wt %.
(4) The therapeutic or prophylactic agent as recited in any one of (1) to (3) above, wherein an n-3 polyunsaturated fatty acid accounts for at least 15% of the fatty acid composition of the krill oil.
(5) The therapeutic or prophylactic agent as recited in any one of (1) to (4) above, wherein eicosapentaenoic acid accounts for at least 10% of the fatty acid composition of the krill oil.
(6) The therapeutic or prophylactic agent as recited in any one of (1) to (5) above, wherein docosahexaenoic acid accounts for at least 5% of the fatty acid composition of the krill oil.
(7) The therapeutic or prophylactic agent as recited in any one of (1) to (6) above, wherein the anxiety associated disorder is posttraumatic stress disorder.
(8) The therapeutic or prophylactic agent as recited in any one of (1) to (7) above, which is for administering the krill oil to a subject in a dose of 50-5000 mg/50 kg body weight/day.

According to another aspect of the present invention, there are provided therapeutic or prophylactic agents as recited below under (9) to (14).

(9) A therapeutic or prophylactic agent for anxiety associated disorder comprising as an active ingredient a phospholipid having an n-3 polyunsaturated fatty acid as a constituent fatty acid.
(10) The therapeutic or prophylactic agent as recited in (9) above, comprising a phospholipid containing at least 15% of the n-3 polyunsaturated fatty acid in the fatty acid composition.

(11) The therapeutic or prophylactic agent as recited in (9) or (10) above, comprising a phospholipid containing at least 10% of eicosapentaenoic acid in the fatty acid composition.
(12) The therapeutic or prophylactic agent as recited in any one of (9) to (11) above, comprising a phospholipid containing at least 5% of docosahexenoic acid in the fatty acid composition.
(13) The therapeutic or prophylactic agent as recited in any one of (9) to (12) above, wherein the anxiety associated disorder is posttraumatic stress disorder.
(14) The therapeutic or prophylactic agent as recited in any one of (9) to (13) above comprising krill oil.

According to yet another aspect of the present invention, there is provided a pharmaceutical composition comprising the therapeutic or prophylactic agent as recited in any one of (1) to (14) above.

According to a still another aspect of the present invention, there is provided a food or a beverage comprising the therapeutic or prophylactic agent as recited in any one of (1) to (14) above.

According to another aspect of the present invention, there are provided uses as recited in below (15) to (22).
(15) Use of krill oil in the manufacture of a pharmaceutical drug for treatment or prevention of anxiety associated disorder.
(16) The use as recited in (15) above, wherein the krill oil is one purified via a thermal coagulum of krill.
(17) The use as recited in (15) or (16) above, wherein the krill oil has a phospholipid content of at least 30 wt %.
(18) The use as recited in any one of (15) to (17) above, wherein an n-3 polyunsaturated fatty acid accounts for at least 15% of the fatty acid composition of the krill oil.
(19) The use as recited in any one of (15) to (18) above, wherein eicosapentaenoic acid accounts for at least 10% of the fatty acid composition of the krill oil.
(20) The use as recited in any one of (15) to (19) above, wherein docosahexaenoic acid accounts for at least 5% of the fatty acid composition of the krill oil.
(21) The use as recited in any one of (15) to (20) above, wherein the anxiety associated disorder is posttraumatic stress disorder.
(22) The use as recited in any one of (15) to (21) above, wherein the pharmaceutical drug is one for administering the krill oil to a subject in a dose of 50-5000 mg/50 kg body weight/day.

According to yet another aspect of the present invention, there are provided methods as recited below in (23) to (30).
(23) A method of treating or preventing an anxiety associated disorder, comprising administering krill oil to a subject.
(24) The method as recited in (23) above, wherein the krill oil is one purified via a thermal coagulum of krill.
(25) The method as recited in (23) or (24) above, wherein the krill oil has a phospholipid content of at least 30 wt %.
(26) The method as recited in any one of (23) to (25) above, wherein an n-3 polyunsaturated fatty acid accounts for at least 15% of the fatty acid composition of the krill oil.
(27) The method as recited in any one of (23) to (26) above, wherein eicosapentaenoic acid accounts for at least 10% of the fatty acid composition of the krill oil.
(28) The method as recited in any one of (23) to (27) above, wherein docosahexaenoic acid accounts for at least 5% of the fatty acid composition of the krill oil.
(29) The method as recited in any one of (23) to (28) above, wherein the anxiety associated disorder is posttraumatic stress disorder.
(30) The method as recited in any one of (23) to (29) above, which involves administering the krill oil to a subject in a dose of 50-5000 mg/50 kg body weight/day.

According to a still another aspect of the present invention, there are provided foods or beverages as recited below in (31) to (39).
(31) A food or beverage comprising krill oil which is to be used as an emergency food in disaster or as a field ration.
(32) The food or beverage as recited in (31) above, which is accommodated in a container or package for long storage.
(33) The food or beverage as recited in (31) or (32) above, wherein the krill oil is one purified via a thermal coagulum of krill.
(34) The food or beverage as recited in any one of (31) to (33) above, wherein the krill oil has a phospholipid content of at least 30 wt %.
(35) The food or beverage as recited in any one of (31) to (34) above, wherein an n-3 polyunsaturated fatty acid accounts for at least 15% of the fatty acid composition of the krill oil.
(36) The food or beverage as recited in any one of (31) to (35) above, wherein eicosapentaenoic acid accounts for at least 10% of the fatty acid composition of the krill oil.
(37) The food or beverage as recited in any one of (31) to (36) above, wherein docosahexaenoic acid accounts for at least 5% of the fatty acid composition of the krill oil.
(38) The food or beverage as recited in any one of (31) to (37) above, which is used for prevention or treatment of posttraumatic stress disorder.
(39) The food or beverage as recited in any one of (31) to (38) above, which is for administering the krill oil to a subject in a dose of 50-5000 mg/50 kg body weight/day.

According to a further aspect of the present invention, there are provided foods or beverages as recited below in (40) to (47).
(40) A food or beverage comprising krill oil, which is to be used as a food or beverage for patients having an anxiety associated disorder.
(41) The food or beverage as recited in (40) above, which is accommodated in a container or package for long storage.
(42) The food or beverage as recited in (40) or (41) above, wherein the krill oil is one purified via a thermal coagulum of krill.
(43) The food or beverage as recited in any one of (40) to (42) above, wherein the krill oil has a phospholipid content of at least 30 wt %.
(44) The food or beverage as recited in any one of (40) to (43) above, wherein an n-3 polyunsaturated fatty acid accounts for at least 15% of the fatty acid composition of the hill oil.
(45) The food or beverage as recited in any one of (40) to (44) above, wherein eicosapentaenoic acid accounts for at least 10% of the fatty acid composition of the krill oil.
(46) The food or beverage as recited in any one of (40) to (45) above, wherein docosahexaenoic acid accounts for at least 5% of the fatty acid composition of the krill oil.
(47) The food or beverage as recited in any one of (40) to (46) above, wherein the anxiety associated disorder is posttraumatic stress disorder.
(48) The food or beverage as recited in any one of (40) to (47) above, which is for administering the krill oil to a subject in a dose of 50-5000 mg/50 kg body weight/day.

According to yet another aspect of the present invention, there are provided methods for alleviating fear memory or preventing the formation of fear memory as recited below in (49) to (57).
(49) A method for alleviating fear memory or preventing the formation of fear memory, comprising allowing a subject to ingest an n-3 polyunsaturated fatty acid in an increased amount within a safe range while restricting the ingestion of an n-6 polyunsaturated fatty acid.

(50) The method as recited in (49) above, wherein the weight ratio of the n-3 polyunsaturated fatty acid to the n-6 polyunsaturated fatty acid as ingested is at least 0.8.

(51) The method as recited in any one of (49) to (50) above, wherein the n-3 polyunsaturated fatty acid and/or n-6 polyunsaturated fatty acid is either an unsaturated fatty acid derived from a constituent fatty acid in a lipid or an unsaturated fatty acid derived from an C1-6 alkyl ester.

(52) The method as recited in any one of (49) to (51) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(53) The method as recited in any one of (49) to (52) above, wherein the n-3 polyunsaturated fatty acid is eicosapentaenoic acid or docosahexaenoic acid.

(54) The method as recited in any one of (49) to (53) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(55) The method as recited in any one of (49) to (54) above, wherein the n-6 polyunsaturated fatty acid is linoleic acid or arachidonic acid.

(56) The method as recited in any one of (51) to (55) above, wherein the lipid is one derived from krill oil or fish oil.

(57) The method as recited in any one of (49) to (56) above, which is for use in treatment or prevention of posttraumatic stress disorder.

According to a still further aspect of the present invention, there are provided agents for alleviating fear memory or preventing the formation of fear memory as recited below in (58) to (67).

(58) An agent for alleviating fear memory or preventing the formation of fear memory comprising an n-3 polyunsaturated fatty acid, which is for administration with a restricted ingestion of an n-6 polyunsaturated fatty acid.

(59) The agent for alleviating fear memory or preventing the formation of fear memory as recited in (58) above, which is for administration such that the weight ratio of the n-3 polyunsaturated fatty acid to the n-6 polyunsaturated fatty acid as ingested is at least 0.8.

(60) The agent for alleviating fear memory or preventing the formation of fear memory as recited in any one of (58) to (59) above, wherein the n-3 polyunsaturated fatty acid and/or n-6 polyunsaturated fatty acid is either an unsaturated fatty acid derived from a constituent fatty acid in a lipid or an unsaturated fatty acid derived from an C1-6 alkyl ester.

(61) The agent for alleviating fear memory or preventing the formation of fear memory as recited in any one of (58) to (60) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(62) The agent for alleviating fear memory or preventing the formation of fear memory as recited in any one of (58) to (61) above, wherein the n-3 polyunsaturated fatty acid is eicosapentaenoic acid or docosahexaenoic acid.

(63) The agent for alleviating fear memory or preventing the formation of fear memory as recited in any one of (58) to (62) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(64) The agent for alleviating fear memory or preventing the formation of fear memory as recited in any one of (58) to (63) above, wherein the n-6 polyunsaturated fatty acid is linoleic acid or arachidonic acid.

(65) The agent for alleviating fear memory or preventing the formation of fear memory as recited in any one of (60) to (64) above, wherein the lipid is one derived from krill oil or fish oil.

(66) The agent for alleviating fear memory or preventing the formation of fear memory as recited in any one of (58) to (65) above, which is for use in treatment or prevention of posttraumatic stress disorder.

(67) The agent for alleviating fear memory or preventing the formation of fear memory as recited in any one of (60) to (66) above, which is for allowing a subject to ingest the lipid in a dose of 50-5000 mg/50 kg body weight/day.

According to a still further aspect of the present invention, there is provided a pharmaceutical composition as recited below in (68).

(68) A pharmaceutical composition comprising the agent for alleviating fear memory or preventing the formation of fear memory as recited in any one of (58) to (67) above.

According to a still another aspect of the present invention, there are provided foods and beverages as recited below in (69) to (72).

(69) A food or beverage comprising the agent for alleviating fear memory or preventing the formation of fear memory as recited in any one of (58) to (67) above.

(70) The food or beverage as recited in (69) above, which is to be used as an emergency food in disaster or as a field ration.

(71) The food or beverage as recited in any one of (69) to (70) above, which is accommodated in a container or package for long storage.

(72) The food or beverage as recited in any one of (69) to (71) above, which is to be used as a food for patients having fear memory.

According to yet another aspect of the present invention, there are provided biomarkers as recited below in (73) to (81).

(73) A biomarker for determining the risk of suffering a fear memory associated disorder, comprising fatty acids derived from blood that contains an n-3 polyunsaturated fatty acid and an n-6 polyunsaturated fatty acid, wherein the weight ratio of the n-3 polyunsaturated fatty acid to the n-6 polyunsaturated fatty acid is at least 0.8.

(74) The biomarker as recited in (73) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(75) The biomarker as recited in any one of (73) to (74) above, wherein the n-3 polyunsaturated fatty acid is eicosapentaenoic acid or docosahexaenoic acid.

(76) The biomarker as recited in any one of (73) to (75) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(77) The biomarker as recited in any one of (73) to (76) above, wherein the n-6 polyunsaturated fatty acid is linoleic acid or arachidonic acid.

(78) The biomarker as recited in any one of (73) to (77) above, wherein the fatty acids are ones obtained from a blood sample.

(79) The biomarker as recited in any one of (73) to (78) above, wherein the fear memory associated disorder is an anxiety disorder or a mood disorder.

(80) The biomarker as recited in (79) above, wherein the anxiety disorder is posttraumatic stress disorder.

(81) The biomarker as recited in (79) above, wherein the mood disorder is depression.

According to a still another aspect of the present invention, there are provided methods of diagnosing fear memory associated disorder as recited below in (82) to (89).

(82) A method of diagnosing the risk of suffering a fear memory associated disorder, comprising measuring the weight ratio in blood of an n-3 polyunsaturated fatty acid to an n-6 polyunsaturated fatty acid and determining that a subject found to have a measured weight ratio greater than a reference value is a low-risk subject, wherein the reference value is any one selected from values of 0.8 and greater.

(83) The method of diagnosis as recited in (82) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(84) The method of diagnosis as recited in any one of (82) to (83) above, wherein the n-3 polyunsaturated fatty acid is eicosapentaenoic acid or docosahexaenoic acid.

(85) The method of diagnosis as recited in any one of (82) to (84) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(86) The method of diagnosis as recited in any one of (82) to (85) above, wherein the n-6 polyunsaturated fatty acid is linoleic acid or arachidonic acid.

(87) The method of diagnosis as recited in any one of (82) to (86) above, wherein the fear memory associated disorder is an anxiety disorder or a mood disorder.

(88) The method of diagnosis as recited in (87) above, wherein the anxiety disorder is posttraumatic stress disorder.

(89) The method of diagnosis as recited in (87) above, wherein the mood disorder is depression.

According to yet another aspect of the present invention, there are provided methods of testing for fear memory associated disorder as recited below in (90) to (97).

(90) A method of testing for the risk of suffering a fear memory associated disorder, comprising measuring the weight ratio in blood of an n-3 polyunsaturated fatty acid to an n-6 polyunsaturated fatty acid and determining that a subject found to have a measured weight ratio greater than a reference value is a low-risk subject, wherein the reference value is any one selected from values of 0.8 and greater.

(91) The method of testing as recited in (90) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(92) The method of testing as recited in any one of (90) to (91) above, wherein the n-3 polyunsaturated fatty acid is eicosapentaenoic acid or docosahexaenoic acid.

(93) The method of testing as recited in any one of (90) to (92) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(94) The method of testing as recited in any one of (90) to (93) above, wherein the n-6 polyunsaturated fatty acid is linoleic acid or arachidonic acid.

(95) The method of testing as recited in any one of (90) to (94) above, wherein the fear memory associated disorder is an anxiety disorder or a mood disorder.

(96) The method of testing as recited in (95) above, wherein the anxiety disorder is posttraumatic stress disorder.

(97) The method of testing as recited in (95) above, wherein the mood disorder is depression.

According to a further aspect of the present invention, there is provided a kit as recited below in (98).

(98) A kit comprising reagents for carrying out the method of diagnosis as recited in any one of (82) to (89) above and/or the method of testing as recited in any one of (90) to (97) above.

According to a still further aspect of the present invention, there are provided compositions as recited below in (99) to (110).

(99) A composition for activating endocannabinoid signaling pathway comprising a lipid comprising an n-3 polyunsaturated fatty acid as a constituent fatty acid.

(100) The composition as recited in (99) above, wherein the weight ratio of the n-3 polyunsaturated fatty acid to an n-6 polyunsaturated fatty acid in the fatty acid composition of the lipid is at least 0.8.

(101) The composition as recited in any one of (99) to (100) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(102) The composition as recited in any one of (99) to (101) above, wherein the n-3 polyunsaturated fatty acid is eicosapentaenoic acid or docosahexaenoic acid.

(103) The composition as recited in any one of (99) to (102) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(104) The composition as recited in any one of (99) to (103) above, wherein the n-6 polyunsaturated fatty acid is linoleic acid or arachidonic acid.

(105) The composition as recited in any one of (99) to (104) above, wherein the lipid is one derived from krill oil or fish oil.

(106) The composition as recited in any one of (99) to (105) above, which is to be used to alleviate fear memory or prevent the formation of fear memory.

(107) The composition as recited in any one of (99) to (105) above, which is to be used to treat or prevent an anxiety disorder or a mood disorder.

(108) The composition as recited in (107) above, wherein the anxiety disorder is posttraumatic stress disorder.

(109) The composition as recited in (107) above, wherein the mood disorder is depression.

(110) The composition as recited in any one of (99) to (109) above, which is for administering to a subject in a dose of 50-5000 mg/50 kg body weight/day.

According to another aspect of the present invention, there are provided therapeutic or prophylactic agents as recited below in (111) to (118).

(111) A therapeutic or prophylactic agent for an anxiety associated disorder, comprising a lipid comprising an n-3 polyunsaturated fatty acid as a constituent fatty acid and wherein the weight ratio of the n-3 polyunsaturated fatty acid to an n-6 polyunsaturated fatty acid in the fatty acid composition is at least 0.8.

(112) The therapeutic or prophylactic agent as recited in (111) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(113) The therapeutic or prophylactic agent as recited in any one of (111) to (112) above, wherein the n-3 polyunsaturated fatty acid is eicosapentaenoic acid or docosahexaenoic acid.

(114) The therapeutic or prophylactic agent as recited in any one of (111) to (113) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(115) The therapeutic or prophylactic agent as recited in any one of (111) to (114) above, wherein the n-6 polyunsaturated fatty acid is linoleic acid or arachidonic acid.

(116) The therapeutic or prophylactic agent as recited in any one of (111) to (115) above, wherein the lipid is one derived from krill oil or fish oil.

(117) The therapeutic or prophylactic agent as recited in any one of (111) to (116) above, wherein the anxiety associated disorder is posttraumatic stress disorder.

(118) The therapeutic or prophylactic agent as recited in any one of (111) to (117) above, which is for administering the lipid to a subject in a dose of 50-5000 mg/50 kg body weight/day.

According to yet another aspect of the present invention, there is provided a pharmaceutical composition as recited below in (119).

(119) A pharmaceutical composition comprising the therapeutic or prophylactic agent as recited in any one of (111) to (118) above.

According to a still another aspect of the present invention, there are provided foods and beverages as recited below in (120) to (123).

(120) A food or beverage comprising the therapeutic or prophylactic agent as recited in any one of (111) to (118) above.

(121) The food or beverage as recited in (120) above, which is to be used as an emergency food in disaster or as a field ration.

(122) The food or beverage as recited in any one of (120) to (121) above, which is accommodated in a container or package for long storage.

(123) The food or beverage as recited in any one of (120) to (122) above, which is to be used as a food for patients having fear associated disorder.

According to yet another aspect of the present invention, there are provided biomarkers as recited below in (124) to (130).

(124) A biomarker for determining the risk of suffering a fear memory associated disorder, comprising fatty acids derived from blood comprising an n-3 polyunsaturated fatty acid and an n-6 polyunsaturated fatty acid, wherein the weight ratio of the n-3 polyunsaturated fatty acid to the n-6 polyunsaturated fatty acid is at least 0.8.

(125) The biomarker as recited in (124) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(126) The biomarker as recited in any one of (124) to (125) above, wherein the n-3 polyunsaturated fatty acid is eicosapentaenoic acid or docosahexaenoic acid.

(127) The biomarker as recited in any one of (124) to (126) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(128) The biomarker as recited in any one of (124) to (127) above, wherein the n-6 polyunsaturated fatty acid is linoleic acid or arachidonic acid.

(129) The biomarker as recited in any one of (124) to (128) above, wherein the fatty acids are ones obtained from a blood sample.

(130) The biomarker as recited in any one of (124) to (129) above, wherein the anxiety associated disorder is posttraumatic stress disorder.

According to a still another aspect of the present invention, there are provided methods of diagnosing anxiety associated disorder as recited below in (131) to (136).

(131) A method of diagnosing the risk of suffering an anxiety associated disorder, comprising measuring the weight ratio in blood of an n-3 polyunsaturated fatty acid to an n-6 polyunsaturated fatty acid and determining that a subject found to have a measured weight ratio greater than a reference value is a low-risk subject, wherein the reference value is any one selected from values of 0.8 and greater.

(132) The method of diagnosing as recited in (131) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(133) The method of diagnosing as recited in any one of (131) to (132) above, wherein the n-3 polyunsaturated fatty acid is eicosapentaenoic acid or docosahexaenoic acid.

(134) The method of diagnosing as recited in any one of (131) to (133) above, wherein the n-6 polyunsaturated fatty acid is at least one n-6 polyunsaturated fatty acid selected from among linoleic acid, γ-linolenic acid, eicosadienoic acid, dihomo-γ-linolenic acid, arachidonic acid, docosadienoic acid, and adrenic acid.

(135) The method of diagnosing as recited in any one of (131) to (134) above, wherein the n-6 polyunsaturated fatty acid is linoleic acid or arachidonic acid.

(136) The method of diagnosing as recited in any one of (131) to (135) above, wherein the anxiety associated disorder is posttraumatic stress disorder.

According to yet another aspect of the present invention, there are provided methods of testing for anxiety associated disorder as recited below in (137) to (142).

(137) A method of testing for the risk of acquiring an anxiety associated disorder, comprising measuring the weight ratio in blood of an n-3 polyunsaturated fatty acid to an n-6 polyunsaturated fatty acid and determining that a subject found to have a measured weight ratio greater than a reference value is a low-risk subject, wherein the reference value is any one selected from values of 0.8 and greater.

(138) The method of testing as recited in (137) above, wherein the n-3 polyunsaturated fatty acid is at least one n-3 polyunsaturated fatty acid selected from among α-linolenic acid, eicosapentaenoic acid, docosapentaenoic acid, and docosahexaenoic acid.

(139) The method of testing as recited in any one of (137) to (138) above, wherein the n-3 polyunsaturated fatty acid is eicosapentaenoic acid or docosahexaenoic acid.

(140) The method of testing as recited in any one of (137) to (139) above, wherein the n-6 polyunsaturated fatty acid is at least one n-6 polyunsaturated fatty acid selected from among linoleic acid, linolenic acid, γ-linolenic acid, eicosadienoic acid, dihomo-γ-linolenic acid, arachidonic acid, docosadienoic acid, and adrenic acid.

(141) The method of testing as recited in any one of (137) to (140) above, wherein the n-6 polyunsaturated fatty acid is linoleic acid or arachidonic acid.

(142) The method of testing as recited in any one of (137) to (141) above, wherein the anxiety associated disorder is posttraumatic stress disorder.

According to a further aspect of the present invention, there is provided a kit as recited below in (143).

(143) A kit comprising a reagent for carrying out the method of diagnosing as recited in any one of (131) to (136) above and/or the method of testing as recited in any one of (137) to (142) above.

According to yet another aspect of the present invention, there are provided therapeutic or prophylactic agents as recited below in (144) to (145).

(144) A therapeutic or prophylactic agent for a fear memory associated disorder comprising krill oil as an active ingredient.

(145) A therapeutic or prophylactic agent for a mood associated disorder comprising hill oil as an active ingredient.

Advantageous Effects of Invention

The present invention provides a method of intervention for anxiety associated disorders, in particular, trauma-derived disorders such as PTSD. The present invention particularly provides therapeutic or prophylactic agents for anxiety associated disorders, which are sufficiently safe that they are suitable for continuing ingestion as foods, beverages, or dietary supplements. In addition, the present invention provides a method of intervention for alleviating fear memory or preventing its formation.

BRIEF DESCRIPTION OF DRAWINGS

FIG. 14-1 is a graph showing the correlation between the ratio of n-3 polyunsaturated fatty acids to n-6 polyunsaturated fatty acids in various types of solid diet (horizontal axis) and the relative freezing time in a fear conditioning experiment with mice fed on those diets for 6 weeks (vertical axis); all values refer to mean±standard error.

FIG. 14-2 is a graph showing the correlation between the ratio of n-3 polyunsaturated fatty acid to n-6 polyunsaturated fatty acid in the sera of mice fed on various types of solid diet (horizontal axis) and the relative freezing time in a fear conditioning experiment with the mice fed on those diets for 6 weeks (vertical axis); all values refer to mean±standard error.

FIG. 14-3 is a graph showing the correlation between the ratio of docosahexaenoic acid (DHA) to arachidonic acid (AA) in the sera of mice fed on various types of solid diet (horizontal axis) and the relative freezing time in a fear conditioning experiment with the mice fed on those diets for 6 weeks (vertical axis); all values refer to mean±standard error.

FIG. 14-4 is a graph showing the correlation between the ratio of eicosapentaenoic acid (EPA) to arachidonic acid (AA) in the sera of mice fed on various types of solid diet (horizontal axis) and the relative freezing time in a fear conditioning experiment with the mice fed on those diets for 6 weeks (vertical axis); all values refer to mean±standard error.

FIG. 14-5 is a graph showing the correlation between the ratio of n-3 polyunsaturated fatty acids to n-6 polyunsaturated fatty acids in the cerebral cortex of mice fed on various types of solid diet (horizontal axis) and the relative freezing time in a fear conditioning experiment with the mice fed on those diets for 6 weeks (vertical axis); all values refer to mean±standard error.

FIG. 14-6 is a graph showing the correlation between the ratio of docosahexaenoic acid (DHA) to arachidonic acid (AA) in the cerebral cortex of mice fed on various types of solid diet (horizontal axis) and the relative freezing time in a fear conditioning experiment with the mice fed on those diets for 6 weeks (vertical axis); all values refer to mean±standard error.

FIG. 14-7 is a graph showing the correlation between the ratio of n-3 polyunsaturated fatty acids to n-6 polyunsaturated fatty acids in the hippocampus of mice fed on various types of solid diet (horizontal axis) and the relative freezing time in a fear conditioning experiment with the mice fed on those diets for 6 weeks (vertical axis); all values refer to mean±standard error.

FIG. 14-8 is a graph showing the correlation between the ratio of docosahexaenoic acid (DHA) to arachidonic acid (AA) in the hippocampus of mice fed on various types of solid diet (horizontal axis) and the relative freezing time in a fear conditioning experiment with the mice fed on those diets for 6 weeks (vertical axis); all values refer to mean±standard error.

DESCRIPTION OF EMBODIMENTS

Figure 1:
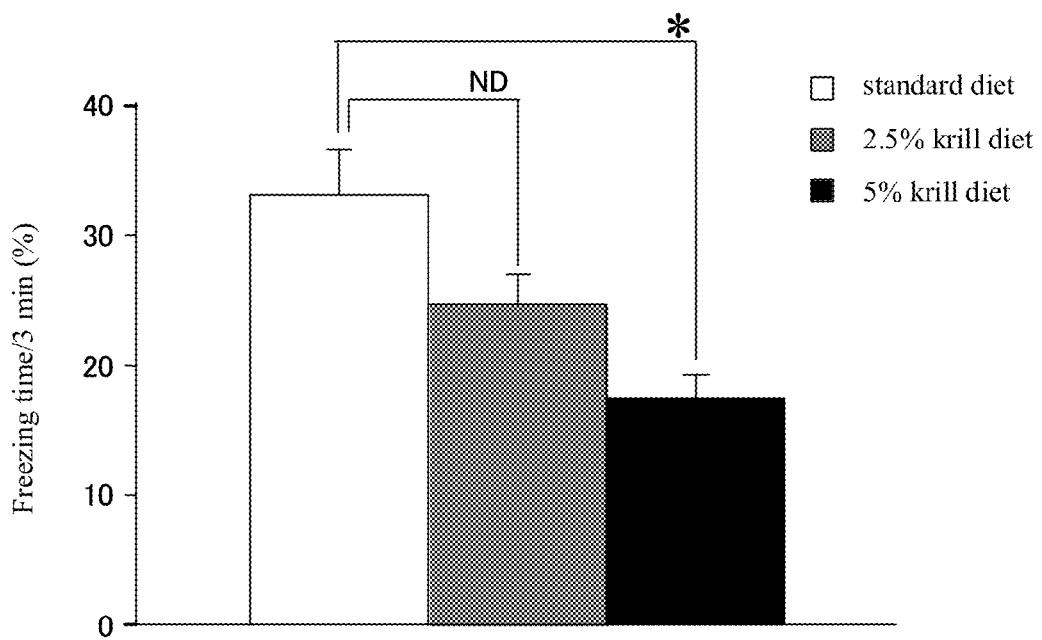
FIG. 1 is a graph showing the effect of 6-week feeding of AIN-93G modified hill solid diet on the freezing response of mice in a fear conditioning experiment; each group consisted of 12 animals; the vertical axis represents the freezing time in a 3-min period; all values refer to mean±standard error; ND indicates the absence of any significant difference and indicates the presence of a significant difference.

On the following pages, the present invention is described more specifically.

The krill oil to be used in the present invention is not particularly limited if it is an oil prepared from hill. The hill as referred to herein may be an arthropod belonging to the phylum Arthropoda, subphylum Crutacea, class Malacostraca, and examples include arthropods belonging to the phylum Arthropoda, subphylum Crutacea, class Malacostraca, order Eucarida, family Euphausiacea, such as antarctic hill (*Euphausia superba*), and arthropods belonging to the phylum Arthropoda, subphylum Crutacea, class Malacostraca, order Peracarida, family Mysidae, such as mysids caught in the seas around Japan. It should, however, be noted that antarctic hill is particularly preferred from the viewpoints of stability in catch and uniformity in the quality of the lipid component.

The krill oil to be used in the present invention can be obtained by known production methods. For example, it can be produced by referring to the known methods described in WO 2000/023546 A1, WO 2009/027692 A1, WO 2010/035749 A1, WO 2010/035750 A1, etc. The lipids that can be produced by the methods described in these international publications can preferably be used in the present invention.

The krill oil can be prepared by extraction with suitable organic solvents from a solids content as a hill-derived starting material in accordance with the methods described in the international publications identified above. Suitable organic solvents include, for example, alcohols such as methanol, ethanol, propanol, isopropanol, butanol, propylene glycol, and butylene glycol, as well as methyl acetate, ethyl acetate, acetone, chloroform, toluene, pentane, hexane, cyclohexane, etc., which may be used either alone or in combination of two or more species. When these solvents are used, their mixing ratio or the proportion between raw material and solvent may be set at any desired value.

The above-mentioned solids content as the krill-derived starting material may be in the form of dried krill, milled hill, raw hill, or frozen hill; alternatively, either whole hill or a part thereof may be pressed into a liquid form and the resulting pressed liquid is heated to separate a solids content from water-soluble components. The pressing operation can be performed with commonly employed apparatuses, including a hydraulic press, a screw press, a meat and bone separator, a press dehydrator, a centrifuge, and combinations thereof.

The pressed liquid may be heated under an atmospheric, superatmospheric, or subatmospheric pressure at 50° C. or higher, preferably at 70-150° C., particularly preferably at 85-110° C. Upon this heating, a solids content (thermal coagulum) is separated from water-soluble components and filtered, centrifuged or otherwise treated to give a thermal coagulum. The thermal coagulum may be dried as appropriate before use. The drying operation can be performed by either one or combinations of hot air drying, drying with vapor, drying through high-frequency/microwave heating, drying under vacuum/reduced pressure, drying through freezing/thawing, and drying with a desiccant. If the drying temperature is unduly high, the lipid is oxidized to give off a malodor; hence, drying is typically performed at 90° C. or below, preferably at 75° C. or below, more preferably at 55° C. or below. Drying is a preferred process because it allows removal of volatile impurities. Said thermal coagulum or dried product thereof contains astaxanthin and can preferably be applied in the present invention.

The above-mentioned thermal coagulum of pressed hill liquid or dried product thereof may be washed with water to lower the concentration of water-soluble components and, hence, are suitable for obtaining krill oil with a lowered residual content of impurities. Washing with water can be performed using freshwater or seawater in a volume at least four times, preferably at least ten times, the weight of the dry content in the thermal coagulum or dried product thereof. Preferably, washing is done at least twice, more preferably at least three times. To perform washing, water may be poured to the thermal coagulum or dried product thereof in a vessel and after standing for at least 5 minutes, the water content is separated. Depending on the form of the thermal coagulum or dried product thereof, thorough agitation is also effective. Alternatively, the thermal coagulum or dried product thereof in a vessel may be washed under flushing water.

Furthermore, the above-mentioned thermal coagulum or dried product thereof, either as they are or after being washed, may be treated in the following way to give a fraction with an increased content of phosphatidylcholine (PC). For example, the thermal coagulum or dried product thereof, either as they are or after being washed, may be treated with a solvent such as ethanol, hexane, chloroform or acetone to give an extracted oil. Then, said extracted oil is subjected to chromatography using silica gel or the like, whereupon impurities are separated from the phospholipid fraction, which is then concentrated. The obtained fraction is PC rich.

Phosphatidylserine (PS) which may be obtained by extraction from animal tissues can be obtained more efficiently by using another phospholipid as the starting material. For example, PS can be obtained by reacting PC and serine enzymatically with the aid of the catalytic action of phospholipase D. The weight ratio of serine to phospholipid that are to be used in said reaction may be set between 0.5 and 3, preferably between 1 and 2. Phospholipase D can be used at a weight ratio between 0.05 and 0.2, preferably between 0.1 and 0.15, per gram of phospholipid. Phospholipase D that can be used is one that is derived from microorganisms or plants such as cabbage.

The above-mentioned enzymatic reaction can be performed using methods known in the technical field of interest; for example, it may be performed in a solvent such as ethyl acetate at 35 to 45° C. for 20 to 24 hours.

The amount of the krill oil to be ingested by subjects in the present invention is not particularly limited if it is at least an effective amount that provides the desired efficacy. The "effective amount" as referred to herein means the necessary amount for treating or preventing anxiety associated disorders. For example, the daily amount of krill oil to be ingested is 100-10000 mg/kg, preferably 200-5000 mg/kg, more preferably 500-2000 mg/kg, per kilogram of an animal's body weight. In particular, the amount to be ingested by a human adult is 50-5000 mg/50 kg body weight, preferably 100-3000 mg/50 kg body weight, more preferably 150-2000 mg/50 kg body weight, and particularly preferably 200-1000 mg/50 kg body weight, per day. In order to obtain a more marked effect in a human adult, the amount of intake is preferably increased but if it is excessive, increased oiliness results to cause undesirable effects including retarded absorption, indigestion, dyspepsia, and loss of appetite. The amounts of ingestion indicated above may refer to a single intake or multiple, for example, two or three intakes.

The krill oil to be used in the present invention contains phospholipids; the content of phospholipids is not particularly limited but it may be at least 10 wt %, preferably at least 20 wt %, and more preferably at least 30 wt %. Purification is required to obtain krill oil containing phospholipids in proportions hither than a certain value; however, the higher the purity of phospholipids to be enriched, the higher the viscosity and the greater the difficulty involved in purification; hence, the content of phospholipids in krill oil may be no greater than 99%, more preferably no greater than 95 wt %.

The term phospholipids as used herein refers to substances in which at least one of the three hydroxyl groups of glycerol is esterified with a fatty acid and another hydroxyl group is covalently bonded to phosphoric acid. Phosphoric acid is typically covalently bonded to a hydroxyl group at the 1- or 3-position of glycerol. Phospholipids are known as a major component of cell membranes and have a hydrophilic phosphate part and a hydrophobic fatty acid part. Phospholipids are divided into two types: diacylglycerophospholipids having the fatty acid parts at 1- and 2-positions on the glycerol backbone, and lysoacylglycerophospholipids. Lysoacylglycerophospholipids are divided into 1-acylglycerolysophospholipids having the fatty acid part only at 1-position on the glycerol backbone and 2-acylglycerolysophospholipids having the fatty acid part only at 2-position on the glycerol backbone. The phospholipids as referred to herein embrace any one of these phospholipids, with diacylglycerophospholipids being particularly preferred. Exemplary diacyiglylcerophospholipids include phosphatidylcholine (PC), phosphatidylethanolamine (PE), phosphatidylserine (PS), phosphatidylinositol (PI), phosphatidylglycerol (PG), cardiolipin (CL), phosphatidic acid (PA), and mixtures of two or more kinds thereof, preferably PC, PE, PS, PI, PA, and mixtures of two or more kinds thereof, particularly preferably PC, PS, and a mixture thereof. Exemplary lysoacylglycerophospholipids include 1- or 2-lysoPC, 1- or 2-lysoPE, 1- or 2-lysoPS, 1- or 2-lysoPI, 1- or 2-lysoPG, 1- or 2-lysoCL, 1- or 2-lysoPA, and mixtures of two or more kinds thereof, preferably 1- or 2-lysoPC, 1- or 2-lysoPE, 1- or 2-lysoPS, 1- or 2-lysoPI, 1- or 2-lysoPA, and mixtures of two or more kinds thereof, particularly preferably 1- or 2-lysoPC, 1- or 2-lysoPS, and a mixture thereof.

The krill oil to be used in the present invention contains n-3 polyunsaturated fatty acids as the fatty acid part of a lipid such as phospholipid or as free fatty acids. The term n-3 polyunsaturated fatty acids as referred to herein are fatty acids that have at least three double bonds and may contain at least 18, preferably at least 20, carbon atoms and in which the third and fourth carbon atoms as counted from the terminal carbon opposite the carboxyl group of the fatty acid molecule form a double bond. Examples of such fatty acids include α-linolenic acid (18:3), eicosapentaenoic acid (20:5, EPA), docosapentaenoic acid (22:5, DPA), docosahexaenoic acid (22:6, DHA), etc., with EPA and DHA being preferred. The proportion of the n-3 polyunsaturated fatty acids in the fatty acid composition of the krill oil to be used in the present invention may be at least 5%, preferably at least 10%, and more preferably at least 15%, as a ratio in the fatty acid composition. The n-3 polyunsaturated fatty acids have high fluidity and, hence, the more they are contained in the lipid, the more effective they are in imparting good properties at low temperature. However, the amount of n-3 polyunsaturated fatty acids that are contained in yet to be purified natural materials is only about 60% at maximum, and to increase their concentration, an extra cost for enrichment will incur. Therefore, the proportion of the n-3 polyunsaturated fatty acids in the constituent fatty acids of the phospholipid in the present invention may be 100% or less, preferably 70% or less, and more preferably 50% or less, as a ratio in the fatty acid composition.

The krill oil to be used in the present invention may contain ingredients such as astaxanthin, sterols, etc.; these ingredients may be added if necessary. Astaxanthin is a carotenoid compound commonly found in crustaceans such as crab and shrimp Astaxanthin may occur either in a free state or in a lipid state involving an ester linkage. The krill oil may contain astaxanthin in a free state at a concentration of 100-5000 ppm, preferably 150-3000 ppm, and more preferably 200-1000 ppm. Astaxanthin is preferably contained in a greater amount because it contributes to stabilizing n-3 polyunsaturated fatty acids as an endogenous antioxidant. It should however be noted that unduly high concentrations of astaxanthin are prone to cause problems with color and flavor. The amount of astaxanthin to be contained in krill oil may be at least 100 ppm, preferably at least 150 ppm, and more preferably at least 200 ppm whereas it may be no greater than 5000 ppm, preferably no greater than 3000 ppm, and more preferably no greater than 1000 ppm.

The sterols contained in the krill oil contribute to the fluidity of lipids, hence, to the absorption of the active ingredients. Exemplary sterols may include cholesterol, sitosterol, stigmasterol, etc. The total amount of sterols contained in phospholipids may be at least 10 ppm, preferably at least 50 ppm, and more preferably at least 200 ppm whereas it may be no greater than 1000 ppm, preferably no greater than 500 ppm, and more preferably no greater than 350 ppm.

In one embodiment of the present invention, eicosapentaenoic acid in the fatty acid composition of krill oil may account for at least 5%, preferably at least 7%, and more preferably at least 10%. In another embodiment of the present invention, docosahexaenoic acid in the fatty acid composition of krill oil may account for at least 1%, preferably at least 3%, and more preferably at least 5%.

The krill oil to be used in the present invention preferably contains phospholipids having n-3 polyunsaturated fatty acids, preferably EPA or DHA, in the fatty acid part. The proportion of n-3 polyunsaturated fatty acids in the constituent fatty acids of the phospholipids to be used in the present invention may be at least 30%, preferably at least 50%, and more preferably at least 70%, as a ratio in the fatty acid composition, whereas it may be no greater than 100%, preferably no greater than 90%, and more preferably no greater than 80%, as a ratio in the fatty acid composition.

In one embodiment of the present invention, there are provided therapeutic or prophylactic agents for anxiety associated disorder that contain as an active ingredient those phospholipids that contain n-3 polyunsaturated fatty acids as constituent fatty acids. The phospholipids referred to herein which contain n-3 polyunsaturated fatty acids as constituent fatty acids may be diacylglycerophospholipids which have the fatty acid part at 1- and 2-positions on the glycerol backbone, or lysoacylglycerophospholipids; the lysoacylglycerophospholipids may be 1-acylglycerolysophospholipids having the fatty acid part only at 1-position on the glycerol backbone or 2-acylglycerolysophospholipids having the fatty acid part only at 2-position on the glycerol backbone. Diacylglycerophospholipids are particularly preferred as the phospholipids to be used in the present invention. Diacylglycerophospholipids and lysoacylglycerophospholipids have already been described hereinabove.

Examples of the 3-polyunsaturated fatty acids contained in the fatty acid part of phospholipids include α-linolenic acid (18:3), eicosapentaenoic acid (20:5, EPA), docosapentaenoic acid (22:5, DPA), docosahexaenoic acid (22:6, DHA), etc., with EPA and DHA being preferred. The proportion of the n-3 polyunsaturated fatty acids in the constituent fatty acids in the phospholipids to be used in the present invention may be at least 30%, preferably at least 50%, and more preferably at least 70%, as a ratio in the fatty acid composition whereas it may be no greater than 100%, preferably no greater than 90%, and more preferably no greater than 80%, as a ratio in the fatty acid composition.

In one embodiment of the present invention, there is provided a method for alleviating fear memory or, preventing the formation of fear memory, which comprises allowing a subject to ingest n-3 polyunsaturated fatty acids while restricting the ingestion of n-6 polyunsaturated fatty acids. The abovementioned n-3 polyunsaturated fatty acids are as already described herein. The term n-6 polyunsaturated fatty acids as referred to herein are fatty acids that have at least two double bonds and may contain at least 18, preferably at least 20, carbon atoms and in which the sixth and seventh carbon atoms as counted from the terminal carbon opposite the carboxyl group of the fatty acid molecule form a double bond. Examples of such fatty acids include linoleic acid (18:2, LA), α-linolenic acid (18:3), eicosadienoic acid (20:2), dihomo-γ-linolenic acid (20:3), arachidonic acid (20:4, AA), docosadienoic acid (22:2), and adrenic acid (22:4). In the technical field of the present invention, n-3 polyunsaturated fatty acids are sometimes referred to as ω3 polyunsaturated fatty acids and n-6 polyunsaturated fatty acids as ω6 polyunsaturated fatty acids; this is also the case in the subject specification and n-3 polyunsaturated fatty acids may sometimes be referred to as ω3 polyunsaturated fatty acids and n-6 polyunsaturated fatty acids as ω6 polyunsaturated fatty acids.

Examples of the n-3 polyunsaturated fatty acids to be ingested by subjects in the present invention include α-linolenic acid (18:3), eicosapentaenoic acid (20:5, EPA), docosapentaenoic acid (22:5, DPA), docosahexaenoic acid (22:6, DHA), etc., with EPA or DHA being preferred. Exemplary n-6 polyunsaturated fatty acids the ingestion of which is to be restricted include linoleic acid (18:2, LA), α-linolenic acid (18:3), eicosadienoic acid (20:2), dihomo-γ-linolenic acid (20:3), arachidonic acid (20:4, AA), docosadienoic acid (22:2), and adrenic acid (22:4), with LA or AA being preferred.

The method for restricting the ingestion of n-6 polyunsaturated fatty acids in the present invention is by adjusting the weight ratio of n-6 polyunsaturated fatty acids in the substance to be ingested by a subject. Specifically, the ingestion of n-6 polyunsaturated fatty acids is restricted by reducing the content of n-6 polyunsaturated fatty acids in the substance to be ingested by the subject. According to Nihonjin no shokuji sesshu kijun (Dietary Reference Intakes for the Japanese (2010 ed.) published by Ministry of Health, Labour and Welfare (Non-Patent Document 18), the adequate daily intake and upper intake level of n-6 polyunsaturated fatty acids is about 5% E and 10% E, respectively, wherein % E is the energy ratio, the percentage in the total energy intake. Note that since n-6 polyunsaturated fatty acids are essential fatty acids and shortage thereof causes deficiency, they must be ingested in an amount of at least 2% E. For example, a minimum amount of n-6 polyunsaturated fatty acids that need be ingested can be assumed to be within the range of 4.8-7.2 g/day. In contrast, the adequate daily intake of n-3 polyunsaturated fatty acids is specified to be about 1% E. It is recommended that eicosapentaenoic acid and docosahexaenoic acid together be ingested in 1 g or more per day. With the dietary habits of Japanese people increasingly changing to western-style food, the intake ratio of n-3 polyunsaturated fatty acids to n-6 polyunsaturated fatty acids (ω3/ω6 ratio) is considerably low at approximate values of 0.1 to 0.2, indicating that the relative ingestion of n-6 polyunsaturated fatty acids is quite high. With traditional Japanese-style food, the relative ingestion of n-3 polyunsaturated fatty acids was higher than it is today and the ω3/ω6 ratio was approximately 0.4 to 0.5 (Non-Patent Document 19.) The substance to be ingested by a subject is preferably provided to the subject in various forms such as food, beverage, and dietary supplement. If the subject is allowed to ingest unsaturated fatty acids in the present invention, the weight ratio of the amount of n-3 polyunsaturated fatty acids to that of n-6 polyunsaturated fatty acids to be ingested is typically at least 0.8, preferably at least 0.9, and more preferably at least 1.0; it is particularly preferred that the intake of n-6 polyunsaturated fatty acids is held to the necessary minimum level whereas n-3 polyunsaturated fatty acids are ingested in increased amounts within a safe range. The weight ratio of unsaturated fatty acids can be determined by commonly employed methods, including, for example, the method of Liparge G. and Roy C. C. (J. Lipid Res., 27, 114-120, 1986.) The methods for measuring the weight ratio of unsaturated fatty acids are not particularly limited and measurement can be performed by using commonly employed measuring apparatuses. For example, the weight ratio of unsaturated fatty acids can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total weight of n-3 polyunsaturated fatty acids to that of n-6 polyunsaturated fatty acids as measured, or is the ratio of the weight of any one or more of n-3 polyunsaturated fatty acids to that of any one or more of n-6 polyunsaturated fatty acids.

The n-3 polyunsaturated fatty acid and/or n-6 polyunsaturated fatty acid which is used in the present invention is either an unsaturated fatty acid derived from a constituent fatty acid in a lipid or an unsaturated fatty acid derived from a $C_{1-6}$ alkyl ester of the n-3 polyunsaturated fatty acid and/or n-6 polyunsaturated fatty acid. Here the lipid having an unsaturated fatty acid as a constituent fatty acid refers to a substance in which at least one of the three hydroxyl groups of glycerol is esterified with the n-3 polyunsaturated fatty acid or n-6 polyunsaturated fatty acid. The lipid having an unsaturated fatty acid as a constituent fatty acid may assume any form, i.e., monoglyceride, diglyceride, or triglyceride. Lipids having unsaturated fatty acids as constituent fatty acids may be ones that are derived from krill oil, fish oil, linseed oil, soy oil, perilla oil, plant oils (soy-derived phospholipid, rapeseed-derived phospholipid), animal-based extracts (egg yolk derived phospholipid), marine extracts (squid extract derived phospholipid, fish extract derived phospholipid, krill extract derived phospholipid), and lipids derived from krill oil or fish oil are preferred.

The $C_{1-6}$ alkyl ester of the n-3 polyunsaturated fatty acid and/or n-6 polyunsaturated fatty acid refers to a substance in which at least one of the hydroxyl groups in a $C_{1-6}$ alcohol is esterified with the n-3 polyunsaturated fatty acid or n-6 polyunsaturated fatty acid. Here, examples of the above-mentioned alkyl ester include methyl ester, ethyl ester, propyl ester, butyl ester, pentyl ester, and hexyl ester or stereoisomers thereof, with methyl ester or ethyl ester being preferred, and ethyl ester being more preferred. Examples of the $C_{1-6}$ alcohol which is a constituent of the above-mentioned alkyl ester include methanol, ethanol, propanol, butanol, heptanol, hexanol or stereoisomers thereof, with methanol or ethanol being preferred, and ethanol being more preferred.

According to the present invention, by adjusting the weight ratio between the n-3 polyunsaturated fatty acid and n-6 polyunsaturated fatty acid to be ingested by subjects, the cannabinoid signaling system can be enhanced efficiently so as to alleviate fear memory or prevent its formation. The method of the present invention for alleviating fear memory or preventing the formation of fear memory can also be used to treat or prevent posttraumatic stress disorder.

In one embodiment of the present invention, there is provided an agent for alleviating fear memory or preventing the formation of fear memory comprising an n-3 polyunsaturated fatty acid, the agent being for administering to a subject the n-3 polyunsaturated fatty acid while restricting the ingestion of an n-6 polyunsaturated fatty acid.

Examples of the n-3 polyunsaturated fatty acids to be used in the present invention include α-linolenic acid (18:3), eicosapentaenoic acid (20:5, EPA), docosapentaenoic acid (22:5, DPA), docosahexaenoic acid (22:6, DHA), etc., with EPA or DHA being preferred. Exemplary n-6 polyunsaturated fatty acids the ingestion of which is to be restricted include linoleic acid (18:2, LA), α-linolenic acid (18:3), eicosadienoic acid (20:2), dihomo-γ-linolenic acid (20:3), arachidonic acid (20:4, AA), docosadienoic acid (22:2), and adrenic acid (22:4), with LA or AA being preferred.

The method for restricting the ingestion of n-6 polyunsaturated fatty acids in the present invention is not particularly limited and this may be attained by, for example, restricting the amount of n-6 polyunsaturated fatty acids in lipids to be ingested as with meals or by adjusting the weight ratio of n-6 polyunsaturated fatty acids in the agent for alleviating fear memory or preventing its formation. Specifically, the ingestion of n-6 polyunsaturated fatty acids is restricted by reducing the content of n-6 polyunsaturated fatty acids in the agent for alleviating fear memory or preventing its formation. The agent for alleviating fear memory or preventing its formation is preferably provided to subjects in such forms as food, beverage, or dietary supplement. When a subject is allowed to ingest n-3 polyunsaturated fatty acids with a restricted ingestion of n-6 polyunsaturated fatty acids in the present invention, the unsaturated fatty acids are ingested by the subject in such a way that the weight ratio of the n-3 polyunsaturated fatty acids ingested as relative to the n-6 polyunsaturated fatty acids is at least 0.8, preferably at least 0.9, and more preferably at least 1.0. It is particularly preferred that the ingestion of the n-6 polyunsaturated fatty acids is held to the necessary minimum level whereas the n-3 polyunsaturated fatty acids are ingested in increased amounts within a safe range. The method for determining the weight ratio of unsaturated fatty acids and the method for measuring the weight ratio of unsaturated fatty acids are as already described herein. Here, the weight ratio of n-3 polyunsaturated fatty acids to n-6 polyunsaturated fatty acids is the ratio of the total weight of n-3 polyunsaturated fatty acids to that of n-6 polyunsaturated fatty acids as measured, or is the ratio of the weight of any one or more of n-3 polyunsaturated fatty acids to that of any one or more of n-6 polyunsaturated fatty acids.

The n-3 polyunsaturated fatty acid and/or n-6 polyunsaturated fatty acid which is used in the present invention is either an unsaturated fatty acid derived from a constituent fatty acid in a lipid or an unsaturated fatty acid derived from a $C_{1-6}$ alkyl ester of then-3 polyunsaturated fatty acid and/or n-6 polyunsaturated fatty acid. Here, the lipid having an unsaturated fatty acid as a constituent fatty acid as well as the $C_{1-6}$ alkyl ester of the n-3 polyunsaturated fatty acid and/or n-6 polyunsaturated fatty acid having unsaturated fatty acid are as already described herein.

The amount of the n-3 polyunsaturated fatty acids to be ingested by subjects in the present invention is not particularly limited if it is at least an effective amount that provides the desired efficacy. For example, the amount of n-3 polyunsaturated fatty acids to be ingested is 15-1500 mg/kg, preferably 30-750 mg/kg, more preferably 75-300 mg/kg, per kilogram of an animal's body weight per day. In particular, the amount to be ingested by a human adult is 7.5-750 mg/50 kg body weight, preferably 15-450 mg/50 kg body weight, more preferably 23-300 mg/50 kg body weight, and particularly preferably 30-150 mg/50 kg body weight, per day. The n-3 polyunsaturated fatty acids can be ingested not only in the form of the composition or medicament of the present invention but also from meals, for example.

The intake of the n-6 polyunsaturated fatty acids whose ingestion is restricted in the present invention may be 15-1900 mg/kg, preferably 30-940 mg/kg, more preferably 75-400 mg/kg, per kilogram of an animal's body weight per day. In particular, the amount to be ingested by a human adult is 7.5-940 mg/50 kg body weight, preferably 15-570 mg/50 kg body weight, more preferably 23-380 mg/50 kg body weight, and particularly preferably 30-190 mg/50 kg body weight, per day. The restricted ingestion of n-6 polyunsaturated fatty acids can be achieved by restricting their intake from meals, for example. According to the present invention, by adjusting the weight ratio of the n-3 polyunsaturated fatty acid and n-6 polyunsaturated fatty acid to be ingested by subjects, the cannabinoid signaling system can be enhanced efficiently so as to alleviate fear memory or prevent its formation. The agent of the present invention for alleviating fear memory or preventing its formation can also be used to treat or prevent posttraumatic stress disorder.

In one embodiment of the present invention, there is provided a composition for activating cannabinoid signaling pathways comprising a lipid comprising n-3 polyunsaturated fatty acids as a constituent fatty acid.

The composition of the present invention for activating cannabinoid signaling pathways contains n-3 polyunsaturated fatty acids. It is particularly preferred that the composition contains no n-6 polyunsaturated fatty acids; if it contains n-6 polyunsaturated fatty acids, the weight ratio of n-3 polyunsaturated fatty acids to n-6 polyunsaturated fatty acids may be at least 0.8, preferably at least 0.9, and more preferably at least 1.0. Examples of the n-3 polyunsaturated fatty acids to be used in the composition of the present invention include α-linolenic acid (18:3), eicosapentaenoic acid (20:5, EPA), docosapentaenoic acid (22:5, DPA), docosahexaenoic acid (22:6, DHA), etc., with EPA or DHA being preferred. Exemplary n-6 polyunsaturated fatty acids include linoleic acid (18:2, LA), α-linolenic acid (18:3), eicosadienoic acid (20:2), dihomo-γ-linolenic acid (20:3), arachidonic acid (20:4, AA), docosadienoic acid (22:2), and adrenic acid (22:4), with LA or AA being preferred.

What is more, the methods for measuring the weight ratio of n-3 polyunsaturated fatty acids to n-6 polyunsaturated fatty acids unsaturated fatty acids are not particularly limited and measurement can be performed by using commonly employed measuring apparatuses. For example, the constituent fatty acids in the lipid can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total weight of the total fatty acid of n-3 polyunsaturated fatty acids to the total weight of n-6 polyunsaturated fatty acids as measured, or is the ratio of the weight of any one or more of n-3 polyunsaturated fatty acids to that of any one or more of n-6 polyunsaturated fatty acids.

According to the present invention, by adjusting the weight ratio between the n-3 polyunsaturated fatty acid and n-6 polyunsaturated fatty acid in the composition, endocannabinoid can be enhanced efficiently so as to alleviate fear memory or prevent its formation. The composition of the present invention can also be used to treat or prevent an anxiety disorder such as posttraumatic stress disorder or a mood disorder such as depression.

In one embodiment of the present invention, there is provided a therapeutic or prophylactic agent for an anxiety associated disorder, comprising a lipid comprising n-3 polyunsaturated fatty acids as a constituent fatty acid and wherein the weight ratio of the n-3 polyunsaturated fatty acids to n-6 polyunsaturated fatty acids in the fatty acid composition of the lipid is at least 0.8.

The lipid to be used in the present invention is one derived from krill oil or fish oil, comprising n-3 polyunsaturated fatty acids as a constituent fatty acid of the lipid. The lipid to be used in the present invention may or may not contain n-6 polyunsaturated fatty acids as a constituent fatty acid. If the lipid to be used in the present invention is composed of n-3 polyunsaturated fatty acids and n-6 polyunsaturated fatty acids, the weight ratio of the n-3 polyunsaturated fatty acids to n-6 polyunsaturated fatty acids in the constituent fatty acids of the lipid may be at least 0.8, preferably at least 0.9, and more preferably at least 1.0 in terms of the fatty acid composition (weight ratio); it is particularly preferred that the constituent fatty acids of the lipid contain no n-6 polyunsaturated fatty acids. The present invention can be used to allow a subject to ingest n-3 polyunsaturated fatty acids while restricting the ingestion of n-6 polyunsaturated fatty acids. In this case, the subject is allowed to ingest the unsaturated fatty acids in such a way that the weight ratio of the n-3 polyunsaturated fatty acids ingested as relative to the n-6 polyunsaturated fatty acids is at least 0.8, preferably at least 0.9, and more preferably at least 1.0. It is particularly preferred that the ingestion of the n-6 polyunsaturated fatty acids is held to the necessary minimum level whereas the n-3 polyunsaturated fatty acids are ingested in increased amounts within a safe range. The proportions of respective fatty acids in the constituent fatty acids of the lipid can be determined by commonly employed methods, including, for example, the method of Liparge G. and Roy C. C. (J. Lipid Res., 27, 114-120, 1986.) The methods for measuring the constituent fatty acids in the lipid are not particularly limited and measurement can be performed by using commonly employed measuring apparatuses. For example, the weight ratio of constituent fatty acids in the lipid can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total weight of the total fatty acid of n-3 polyunsaturated fatty acids to the total weight of n-6 polyunsaturated fatty acids as measured, or is the ratio of the weight of any one or more of n-3 polyunsaturated fatty acids to that of any one or more of n-6 polyunsaturated fatty acids.

Examples of the n-3 polyunsaturated fatty acids contained in the constituent fatty acid part of the lipid include α-linolenic acid (18:3), eicosapentaenoic acid (20:5, EPA), docosapentaenoic acid (22:5, DPA), docosahexaenoic acid (22:6, DHA), etc., with EPA or DHA being preferred. Exemplary n-6 polyunsaturated fatty acids contained in the constituent fatty acid part of the lipid include linoleic acid (18:2, LA), α-linolenic acid (18:3), eicosadienoic acid (20:2), dihomo-γ-linolenic acid (20:3), arachidonic acid (20:4, AA), docosadienoic acid (22:2), and adrenic acid (22:4), with LA or AA being preferred.

Furthermore, the composition containing the lipid which comprises n-3 polyunsaturated fatty acids as a constituent fatty acid is capable of enhancing endocannabinoid efficiently and, hence, can be used to treat or prevent an anxiety associated disorder such as posttraumatic stress disorder.

Any material that contains a phospholipid comprising the above-described n-3 polyunsaturated fatty acids and/or n-6 polyunsaturated fatty acids as constituent fatty acids can be used as the phospholipid of the present invention. Briefly, said phospholipid may be one that contains other components that derive from nature and it is possible to use phospholipids that have a purity of at least, for example, 10 wt %, preferably at least 20 wt %, and more preferably at least 30 wt %. Materials that can be used as the phospholipid of the present invention include extracts of fish and shellfish, animal extracts, egg yolk extracts, plant extracts, fungal extracts, etc., and specific examples include krill oil, fish oil, fish extract, squid extract, bonito ovary extract, extracts of animals fed on diets incorporating n-3 polyunsaturated fatty acids or extracts of the egg yolk of such animals, linseed oil, extracts of genetically recombined plants, etc. and extracts of Labyrinthula, etc. Materials that are particularly abundant in phospholipids include krill oil, squid extract, and bonito ovary extract. By using techniques commonly known in the technical field concerned, such as concentrating, extracting, and/or purifying and blending, the concentrations and purities of lipids in these materials can be adjusted to any desired values. For example, phospholipids containing n-3 polyunsaturated fatty acids at high concentrations can be produced by appropriately blending krill oil, fish oil, linseed oil, soy oil or perilla oil each containing n-3 polyunsaturated fatty acids with lipid-containing krill oil, plant oil (soy derived phospholipid or rapeseed derived phospholipid), animal extract (egg yolk derived phospholipid), or marine extract (squid extract derived phospholipid, fish extract derived phospholipid, or hill extract derived phospholipid). According to the present invention, a phospholipid which comprises n-3 polyunsaturated fatty acids as a constituent fatty acid may be contained as an active ingredient. Phospholipids that can be used are components derived from krill (e.g. ground hill, milled hill, and split hill.)

An orally ingested phospholipid is hydrolyzed to free fatty acids and lysoacylglyerophospholipid, phosphatidic acid, or lysophosphatidic acid. These hydrolyzates dissolve by forming bile acid micelles together with bile acid. Small-intestinal epithelial cells take up the hydrolyzates from the bile micelles and resynthesize triacylglycerol and diacylglyerophospholipid from the incorporated hydrolyzates. Hence, when free polyunsaturated fatty acids are ingested in vivo, they are taken up by small-intestinal epithelial cells via the formation of micelles with bile acid and bind the in vivo glycerol and/or phosphate, whereupon they are taken up again as constituent fatty acids in the triacylglycerol and/or diacylglyerophospholipid. This is how the ingestion of a phospholipid or triacylglycerol together with n-3 polyunsaturated fatty acids contributes to increasing the proportion of an n-3 polyunsaturated fatty acid containing phospholipid in the in vivo resynthesized phospholipid or triacylglycerol and, hence, providing an even higher efficacy.

Ingestion of phospholipids together with n-3 polyunsaturated fatty acids can be realized either by using a lipid prepared by blending fats or oils comprising each of these components as appropriate or by using a phospholipid comprising n-3 polyunsaturated fatty acids as constituent fatty acids; in view of the ease of absorption, stability as materials, and the ease of quality control, a phospholipid comprising n-3 polyunsaturated fatty acids as constituent fatty acids is particularly preferred.

The amount of the phospholipid to be ingested by subjects in the present invention is not particularly limited if it is at least an effective amount that provides the desired efficacy. The effective amount as referred to herein means the necessary amount for treating or preventing anxiety associated disorders. For example, the amount of phospholipid to be ingested is 100-10000 mg/kg, preferably 200-5000 mg/kg, more preferably 500-2500 mg/kg, per kilogram of an animal's body weight per day. In particular, the amount to be ingested by a human adult is 50-5000 mg/50 kg body weight, preferably 100-3000 mg/50 kg body weight, more preferably 150-2000 mg/50 kg body weight, and particularly preferably 200-1000 mg/50 kg body weight, per day. In order to obtain a more marked effect in a human adult, the amount of intake is preferably increased; however, if it is excessive, increased oiliness results to cause undesirable effects including retarded absorption, indigestion, dyspepsia, and loss of appetite. The amounts of ingestion indicated above may refer to a single intake or multiple, for example, two or three intakes.

The phospholipid to be used in the present invention may have other components of krill oil, for example, astaxanthin and sterols, added in appropriate amounts. The phospholipid to be used in the therapeutic or prophylactic agent of the present invention may contain astaxanthin in a free state typically in an amount of 100-5000 ppm, preferably 150-3000 ppm, and more preferably 200-1000 ppm. The amount of astaxanthin to be contained in the phospholipid may be at least 100 ppm, preferably at least 150 ppm, and more preferably at least 200 ppm, but may be no greater than 5000 ppm, preferably no greater than 3000 ppm, and more preferably no greater than 1000 ppm. Sterols may include cholesterol, sitosterol, and stigmasterol. The total amount of sterols to be contained in the phospholipid may be at least 10 ppm, preferably at least 50 ppm, and more preferably at least 200 ppm, but may be no greater than 1000 ppm, preferably no greater than 500 ppm, and more preferably no greater than 350 ppm.

The present invention can be applied to fear memory associated disorders, in particular, trauma derived disorders from among anxiety associated disorders. Examples of anxiety associated disorders include various types of phobia (e.g. agoraphobia, claustrophobia, nyctophobia, acrophobia, fear of low places, atychiphobia, fear of flying, body dysmorphic disorder, nausiphobia, anthrophobia, androphobia, gynephobia, zoo phobia, botanophobia, arachnephobia, belonephobia, etc.), panic disorder, obsessive-compulsive disorder (OCD), posttraumatic stress disorder (PTSD), acute stress disorder (ASD), etc. Exemplary trauma-derived disorders include posttraumatic stress disorder (PTSD) and acute stress disorder (ASD), etc. In particular, the present invention can be applied to a patient of posttraumatic stress disorder (PTSD).

The therapeutic or prophylactic agent of the present invention may, depending on the need, contain conventionally known ingredients such as coloring agents, preservatives, scents, flavoring agents, coating agents, antioxidants, vitamins, amino acids, peptides, proteins, minerals (e.g., iron, zinc, magnesium, iodide), etc.

Examples of antioxidants here mentioned include tocopherol, dried yeast, glutathione, lipoic acid, quercetin, catechin, coenzyme Q10, enzogenol, proanthocyanidins, anthocyanidin, anthocyanin, carotenes, lycopene, flavonoid, resveratrol, isoflavones, zinc, melatonin, ginkgo leaf, *Alpinia zerumbet* leaf, hibiscus, C vitamins, or extracts thereof.

In a specific embodiment, tocopherol is incorporated in such a way that its daily intake is 0.50-650 mg/kg body weight, preferably 5-500 mg/kg body weight, and more preferably 50-300 mg/kg body weight.

In another specific embodiment, catechin is incorporated in such a way that its daily intake is 1-5000 mg/kg body weight, preferably 10-3000 mg/kg body weight, and more preferably 100-1000 mg/kg body weight.

In yet another specific embodiment, C vitamins are incorporated in such a way that their daily intake is 1-1000 mg/kg body weight, preferably 10-800 mg/kg, and more preferably 100-500 mg/kg body weight.

Examples of vitamins include: A vitamins (e.g. retinal, retinol, retinoic acid, carotene, dehydroretinal, lycopene, and salts thereof); B vitamins (e g thiamine, thiamine disulfide, dicethiamine, octothiamine, cycothiamine, bisibuthiamine, bisbenthiamine, prosulthiamine, benfothiamine, fursultiamine, riboflavin, flavin adenine dinucleotide, pyridoxine, pyridoxal, hydroxocobalamin, cyanocobalamin, methylcobalamin, deoxyadenocobalamin, folic acid, tetrahydrofolic acid, dihydrofolic acid, nicotinic acid, nicotinic acid amide, nicotinic alcohol, pantothenic acid, panthenol, biotin, choline, inositol, pangamic acid, and salts thereof); C vitamins (ascorbic acid and its derivatives, erythorbic acid and its derivatives, as well as pharmaceutically acceptable salts thereof); D vitamins (e.g. ergocalciferol, cholecalciferol, hydroxycholecalciferol, dihydroxycholecalciferol, dihydrotachysterol, and pharmaceutically acceptable salts thereof); E vitamins (e.g. tocopherol and its derivatives, ubiquinone derivatives, and pharmaceutically acceptable salts thereof); and other vitamins (e.g. carnitine, ferulic acid, γ-oryzanol, orotic acid, rutin (vitamin P), eriocitrin, hesperidin, and pharmaceutically acceptable salts thereof).

Examples of amino acids include leucine, isoleucine, valine, methionine, threonine, alanine, phenylalanine, tryptophan, lysine, glycine, asparagine, aspartic acid, serine, glutamine, glutamic acid, proline, tyrosine, cysteine, histidine, ornithine, hydroxyproline, hydroxylysine, glycylglycine, aminoethylsulfonic acid (taurine), cystine, and pharmaceutically acceptable salts thereof.

The therapeutic or prophylactic agent of the present invention may be prepared in forms as suitable for pharmaceutical compositions, foods with health-promoting benefits, health foods, beverages, and dietary supplements; examples include various solid formulations such as granules (including dry syrup), capsules (soft and hard capsules), tablets (including chewable tablets and the like), powders (dusts), and pills, as well as liquid formulations such as liquids for internal use (including liquids, suspensions, and syrups.) The therapeutic or prophylactic agent of the present invention may directly be used as pharmaceutical compositions, foods with health-promoting benefits, health foods, dietary supplements, etc.

Examples of additives that may be used to prepare formulations include excipients, lubricants, binders, disintegrants, fluidization agents, dispersants, wetting agents, antiseptics, viscous agents, pH adjusting agents, coloring agents, corrigents, surfactants, and solvent promoters. To make preparations in the form of liquids, thickening agents such as pectin, xanthan gum, and guar gum may be incorporated. If desired, coated tablets may be formulated by using coating agents, or gelatin pastes may be formulated. Even other forms of preparation may be produced in accordance with conventional methods.

The therapeutic or prophylactic agent of the present invention may further be used either as a variety of foods and beverages including drinks, confectionery, bread and soup or as additives therefor. The methods for producing these foods and beverages are not particularly limited if they will not impair the intended effects of the present invention and the methods commonly employed by skilled artisans in the respective applications may be complied with.

According to a further aspect of the present invention, there are provided krill oil containing foods and beverages that are to be ingested by subjects who may potentially suffer a fear experience or an aversive experience and, in particular, there are provided such foods and beverages that are to be used as an emergency food in disaster or as a field ration. According to yet another aspect of the present invention, those foods and beverages are used for ingestion by patients having an anxiety associated disorder, in particular, a trauma-derived disorder.

In the case where the present invention assumes the form of foods and beverages, such foods and beverages are not particularly limited and may cover common types of retort food, frozen food, instant food (e.g. noodle), cans, sausages; cookies, biscuits, cereal bars, crackers, snacks (e.g. potato chips), pastries, cakes, pies, candies, chewing gums (including pellets and sticks), jelly, soup, ice confectionery, dressings, and yogurt; as well as dietary supplements in forms such as tablet, capsule, and emulsion; and soft drinks.

In particular, in order to provide convenience for a subject who ingests it as an emergency food in disaster or as a field ration, the food or beverage of the present invention is preferably accommodated in a container or package for long storage. Examples of such foods and beverages include ones that are sealed in glass containers, resin containers or metal containers, as well as ones that are packaged with highly hermetic materials such as resinous or metallic materials.

The products according to the present invention may be marketed with the therapeutic or prophylactic effect of the present invention being indicated on the packaging container, the product instructions, or the brochure and this practice is within the scope of the present invention. It is also within the scope of the present invention to advertise and market the products according to the present invention with the effects of the present invention being indicated on TV, the internet website, the brochure, newspaper, magazine, and other media.

According to a further aspect of the present invention, there are provided biomarkers for determining the risk of suffering a fear memory associated disorder, comprising n-3 polyunsaturated fatty acids, which are used to determine the risk of suffering a fear memory associated disorder, in particular, an anxiety disorder such as posttraumatic stress disorder or a mood disorder such as depression. Using the biomarkers of the present invention, the weight ratio of n-3 polyunsaturated fatty acids to n-6 polyunsaturated fatty acids is measured and compared with a reference value; if the weight ratio indicated by the biomarker is greater than the reference value, it is concluded that the risk of suffering a fear memory associated disorder is low. The reference value here used in the present invention is for determining the risk of suffering a fear memory associated disorder and it may be any numerical value that is selected from values of, for example, 0.8 and above, preferably 0.9 and above, and more preferably 1.0 and above. For example, if 0.8 is selected as the reference value and exceeded by the measured weight ratio, the subject is held to have a low risk for suffering a fear memory associated disorder. On the other hand, if the measured weight ratio is less than the reference value, the subject is held to have a relatively high risk for suffering a fear memory associated disorder. The subject in the present invention is a mammal, for example, human, bovine, equine, feline, mouse or rat, and human is preferred.

The n-3 polyunsaturated fatty acids and n-6 polyunsaturated fatty acids contained in the biomarker of the present invention are as already described hereinabove. The fatty acids that compose the biomarker are preferably ones that derive from lipids and free fatty acids as obtained from blood samples. Furthermore, the methods for measuring the weight ratio of n-3 polyunsaturated fatty acids to n-6 polyunsaturated fatty acids are not particularly limited and measurement can be performed by using commonly employed measuring apparatuses. For example, the weight ratio of fatty acids can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total fatty acid of the total weight of n-3 polyunsaturated fatty acids to the total weight of n-6 polyunsaturated fatty acids as measured, or is the ratio of the weight of any one or more of n-3 polyunsaturated fatty acids to that of any one or more of n-6 polyunsaturated fatty acids.

According to a still further aspect of the present invention, there are provided a method of diagnosing the risk of suffering a fear memory associated disorder, in particular, an anxiety disorder such as posttraumatic stress disorder or a mood disorder such as depression, as well as a method for testing such risk. The diagnostic method and test method of the present invention each comprises measuring the weight ratio in blood of n-3 polyunsaturated fatty acids to n-6 polyunsaturated fatty acids, preferably the weight ratio of eicosapentaenoic acid (EPA) or docosahexaenoic acid (DHA) to arachidonic acid (AA), and if the measured value is greater than a reference value, the subject is held to have a low risk for suffering a fear memory associated disorder. The reference value here used in the present invention is for determining the risk of suffering a fear memory associated disorder and it may be any numerical value that is selected from values of, for example, 0.8 and above, preferably 0.9 and above, and more preferably 1.0 and above. For example, if 0.8 is selected as the reference value and exceeded by the measured weight ratio, the subject is held to have a low risk for suffering a fear memory associated disorder. On the other hand, if the measured weight ratio is less than the reference value, the subject is held to have a relatively high risk for suffering a fear memory associated disorder. The subject in the present invention is a mammal, for example, human, bovine, equine, feline, mouse or rat, and human is preferred.

The n-3 polyunsaturated fatty acids and n-6 polyunsaturated fatty acids which are to be measured in the diagnostic method and test method of the present invention are as already described hereinabove. The weight ratio of n-3 polyunsaturated fatty acids to n-6 polyunsaturated fatty acids can be determined by commonly employed methods, including, for example, the method of Liparge G. and Roy C. C. (J. Lipid Res., 27, 114-120, 1986.) The methods for measuring the weight ratio of n-3 polyunsaturated fatty acids to n-6 polyunsaturated fatty acids are not particularly limited and measurement can be performed by using commonly employed measuring apparatuses. For example, the weight ratio of fatty acids can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total fatty acid of the total weight of n-3 polyunsaturated fatty acids to the total weight of n-6 polyunsaturated fatty acids as measured, or is the ratio of the weight of any one or more of n-3 polyunsaturated fatty acids to that of any one or more of n-6 polyunsaturated fatty acids.

According to a yet another aspect of the present invention, there is provided a kit comprising reagents for carrying out the diagnostic method and/or test method of the present invention. The kit may comprise a reagent such as an acid, an alkali or a hydrolase that is capable of degrading lipids in blood into fatty acids, and other reagents such as a solvent and a buffer that are used to perform diagnosis and/or test. The kit may further comprise a device or apparatus that are used to measure the weight ratio of n-3 polyunsaturated fatty acids to n-6 polyunsaturated fatty acids, as exemplified by a container, gas chromatography (GC), mass spectrometer (MS), high-performance liquid chromatography (HPLC), liquid chromatography-mass spectrometer (LC/MS), etc. If desired, the kit of the present invention may be accompanied by an instruction manual as an attachment.

According to a still further aspect of the present invention, there are provided biomarkers for determining the risk of suffering a fear memory associated disorder, comprising n-3 polyunsaturated fatty acids, which are used to determine the risk of suffering an anxiety associated disorder, in particular, a trauma-derived disorder. Using the biomarkers of the present invention, the weight ratio of n-3 polyunsaturated fatty acids to n-6 polyunsaturated fatty acids is measured and compared with a reference value; if the weight ratio indicated by the biomarker is greater than the reference value, it is concluded that the risk of suffering an anxiety associated disorder is low. The reference value here used in the present invention is for determining the risk of suffering an anxiety associated disorder and it may be any numerical value that is selected from values of, for example, 0.8 and above, preferably 0.9 and above, and more preferably 1.0 and above. For example, if 0.8 is selected as the reference value and exceeded by the measured weight ratio, the subject is held to have a low risk for suffering an anxiety associated disorder. On the other hand, if the measured weight ratio is less than the reference value, the subject is held to have a relatively high risk for suffering an anxiety associated disorder. The subject in the present invention is a mammal, for example, human, bovine, equine, feline, mouse or rat, and human is preferred.

The n-3 polyunsaturated fatty acids and n-6 polyunsaturated fatty acids contained in the biomarker of the present invention are as already described hereinabove. The fatty acids that compose the biomarker are preferably ones that derive from lipids and free fatty acids as obtained from blood samples. Furthermore, the methods for measuring the weight ratio of n-3 polyunsaturated fatty acids to n-6 polyunsaturated fatty acids are not particularly limited and measurement can be performed by using commonly employed measuring apparatuses. For example, the weight ratio of fatty acids can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total weight of the total fatty acid of n-3 polyunsaturated fatty acids to the total weight of n-6 polyunsaturated fatty acids as measured, or is the ratio of the weight of any one or more of n-3 polyunsaturated fatty acids to that of any one or more of n-6 polyunsaturated fatty acids.

According to a still further aspect of the present invention, there are provided a method of diagnosing the risk of suffering an anxiety associated disorder, in particular, a trauma-derived disorder, as well as a method for testing such risk. The diagnostic method and test method of the present invention each comprises measuring the weight ratio in blood of n-3 polyunsaturated fatty acids to n-6 polyunsaturated fatty acids, preferably the weight ratio of eicosapentaenoic acid (EPA) or docosahexaenoic acid (DHA) to arachidonic acid (AA), and if the measured value is greater than a reference value, the subject is held to have a low risk for suffering an anxiety associated disorder. The reference value here used in the present invention is for determining the risk of suffering an anxiety associated disorder and it may be any numerical value that is selected from values of, for example, 0.8 and above, preferably 0.9 and above, and more preferably 1.0 and above. For example, if 0.8 is selected as the reference value and exceeded by the measured weight ratio, the subject is held to have a low risk for suffering an anxiety associated disorder. On the other hand, if the measured weight ratio is less than the reference value, the subject is held to have a relatively high risk for suffering an anxiety associated disorder. The subject in the present invention is a mammal, for example, human, bovine, equine, feline, mouse or rat, and human is preferred.

The n-3 polyunsaturated fatty acids and n-6 polyunsaturated fatty acids which are to be measured in the diagnostic method and test method of the present invention are as already described hereinabove. The weight ratio of n-3 polyunsaturated fatty acids to n-6 polyunsaturated fatty acids can be determined by commonly employed methods, including, for example, the method of Liparge G. and Roy C. C. (J. Lipid Res., 27, 114-120, 1986.) The methods for measuring the weight ratio of n-3 polyunsaturated fatty acids to n-6 polyunsaturated fatty acids are not particularly limited and measurement can be performed by using commonly employed measuring apparatuses. For example, the weight ratio of fatty acids can be measured by gas chromatography (GC), mass spectrometer (MS), high-performance liquid chromatography (HPLC), or liquid chromatography-mass spectrometer (LC/MS), preferably by gas chromatography (GC). Here, the weight ratio of n-3 polyunsaturated fatty acids to n-6 polyunsaturated fatty acids is the ratio of the total weight of the total fatty acid of n-3 polyunsaturated fatty acids to the total weight of n-6 polyunsaturated fatty acids as measured, or is the ratio of the weight of any one or more of n-3 polyunsaturated fatty acids to that of any one or more of n-6 polyunsaturated fatty acids.

According to a yet another aspect of the present invention, there is provided a kit comprising reagents for carrying out the diagnostic method and/test method of the present invention. The kit may comprise a reagent such as an acid, an alkali or a hydrolase that is capable of degrading lipids in blood into fatty acids, and other reagents such as a solvent and a buffer that are used to perform diagnosis and/or test. The kit may further comprise a device or apparatus that are used to measure the weight ratio of n-3 polyunsaturated fatty acids to n-6 polyunsaturated fatty acids, as exemplified by a container, gas chromatography (GC), mass spectrometer (MS), high-performance liquid chromatography (HPLC), liquid chromatography-mass spectrometer (LC/MS), etc. If desired, the kit of the present invention may be accompanied by an instruction manual as an attachment.

EXAMPLES

The present invention is described more specifically by means of the examples given below but it should be understood that the scope of the present invention is in no way limited by those examples.

[Production of Krill Oil]

A krill oil used for tests was prepared through extraction from antarctic krill by the method described in WO 2010/035750. The ingredients and fatty acid composition of the krill oil used for tests are shown in Tables 1 and 2, respectively. Analysis of the fatty acid composition was outsourced to JAPAN FOOD RESEARCH LABORATORIES. The analysis of basic ingredients covered water content (AOAC 984.20), acid value (AOAC 969.17), peroxide value (AOAC 965.33), astaxanthin (free form, HPLC), and total phospholipid (by the column separation method).

TABLE 1

Basic Ingredients in Krill Oil

| Water content | 0.6% |
| Phospholipid | 47.2% |
| Acid value | 6 |
| Peroxide value | 0.1 meq/kg |
| Astaxanthin | 252 ppm |

TABLE 2

Fatty Acid Composition of Krill Oil (%)

| Fatty acid | Composition (%) |
| --- | --- |
| 14:0 | 12.1 |
| 16:0 | 21.5 |
| 18:1 | 17.7 |
| 18:2n-6 | 1.7 |
| 18:3n-3 | 1.2 |
| 18:4n-3 | 3.4 |
| 20:5n-3 | 15.1 |
| 22:6n-3 | 7.6 |

Test Example 1

Fear Conditioning Test (1)

It has been reported that mice accumulate fear and aversive memories as humans do (Nature 406 722-726, 2000).

The present inventors evaluated the actions of food ingredients on fear memory by the "fear conditioning experiment" (J Neurosci 27 158-166, 2007) which is extensively used as an evaluation system for fear memory in mice.

In this study, AIN-93G solid diet, a standard diet for mice, was modified by replacing part of soy oil as the fat component (accounting for 7% of the total diet weight) with the above-described krill oil. Through this replacement, a diet containing 2.5% krill oil (4.5% soy oil) and another containing 5% krill oil (2% soy oil) in the total diet weight (referred to as 2.5% krill diet and 5% krill diet, respectively) were prepared. The fatty acid composition of each diet is shown in Table 3. Analysis of the fatty acid composition was outsourced to JAPAN FOOD RESEARCH LABORATORIES.

TABLE 3

Fatty Acid Composition of Each Diet (%)

| Fatty acid | Standard diet (7% soy oil) | 5% Krill oil diet (2% soy oil) | 2.5% Krill oil diet (4.5% soy oil) |
| --- | --- | --- | --- |
| 12:0 | 0 | 0.2 | 0 |
| 14:0 | 0 | 7.6 | 3.5 |
| 15:0 | 0 | 0.3 | 0.2 |
| 16:0 | 11.4 | 18.8 | 14.9 |
| 17:0 | 0 | 1.6 | 0.8 |
| 18:0 | 4.1 | 2.3 | 3.3 |
| 20:0 | 0.3 | 0.2 | 0.3 |
| 22:0 | 0.3 | 0.1 | 0.3 |
| 24:0 | 0.1 | 0 | 0 |
| Total of saturated fatty acids | 16.2 | 31.1 | 23.3 |
| 14:1 | 0 | 0.2 | 0 |
| 16:1 | 0 | 3.9 | 1.9 |
| 17:1 | 0 | 0.2 | 0.1 |
| 18:1 | 22.7 | 19.4 | 21.5 |
| 20:1 | 0.2 | 0.6 | 0.4 |
| 22:1 | 0 | 0.4 | 0.2 |
| Total of monounsaturated fatty acids | 22.9 | 24.7 | 24.1 |
| 16:2 | 0 | 0.4 | 0.2 |
| 16:3 | 0 | 0 | 0.0 |
| 16:4 | 0 | 0.5 | 0.2 |
| 18:2n-6 | 52.5 | 20.2 | 38.2 |
| 18:3n-3 | 7.6 | 3.3 | 5.7 |
| 18:4n-3 | 0 | 2.1 | 0.9 |
| 20:3n-3 | 0 | 0.1 | 0 |
| 20:4n-6 | 0 | 0.2 | 0 |

TABLE 3-continued

Fatty Acid Composition of Each Diet (%)

| Fatty acid | Standard diet (7% soy oil) | 5% Krill oil diet (2% soy oil) | 2.5% Krill oil diet (4.5% soy oil) |
|---|---|---|---|
| 20:4n-3 | 0 | 0.2 | 0 |
| 20:5n-3 | 0 | 9.2 | 4.1 |
| 21:5n-3 | 0 | 0.3 | 0 |
| 22:5n-3 | 0 | 0.3 | 0 |
| 22:6n-3 | 0 | 4.5 | 2 |
| Total of polyunsaturated fatty | 60.1 | 41.3 | 51.3 |
| unknown | 0.8 | 2.9 | 1.3 |
| ω3/ω6 ratio | 0.14 | 0.98 | 0.33 |

In this study, experimental mice at 6 weeks after birth were fed on the standard diet, 2.5% krill diet, or 5% krill diet for 6 weeks. The mice had been fed on CE2 solid diet (product of CLEA Japan, Inc.) until the feeding with those diets started.

A cubic experimental box made of acrylic resin having a bottom of 20 cm×20 cm and a height of 33 cm, with a conductive metallic grid being laid across the bottom, was used as a new environment for conditioning; each mouse was put into the experimental box and conditioned by applying electric shocks (0.8 mA, 2 s) from the bottom grid. Feeling an intense pain from each electric shock, a mouse memorizes that when placed in the new environment, it will suffer pain from electric shocks. The mice were then returned to the breeding cage where they had been kept before the conditioning.

On the next day (the second day of the behavioral experiment), each mouse was put again into the experimental box where it was given electric shocks on the previous day; even in the absence of applied electric shocks, it would be scared to cringe, a characteristic freezing behavior from fear. The degree of fear memory was assessed by the degree of the freezing behavior, namely, the freezing time during a 3-minute exposure to the experimental box.

The above-described fear conditioning experiment was performed on mice that had been fed on the standard diet, 2.5% krill diet, or 5% krill diet for 6 weeks and an example of the results is shown in FIG. 1. The mouse group fed on the 2.5% krill diet (12 animals/group) and the group fed on the 5% krill diet (12 animals/group) showed shorter freezing times than the mouse group fed on the standard diet (12 animals/group) (FIG. 1). Variance analysis, ANOVA, showed a significant variance in the data for the three groups, and upon post-hoc analysis by the Turkey method, a high level of significant difference (p<0.001) was observed between the standard diet group and the 5% krill diet fed group. On the other hand, no significant difference was detected between the standard diet group and the 2.5% krill diet fed group when the same analysis was applied.

The above results show that the 6-week ingestion of the 5% krill diet significantly attenuated the formation of fear memory due to fear conditioning.

Test Example 2

Fear Conditioning Test (2)

In this test, to investigate how the different fat components initially present in the standard diet would affect the action of krill oil, AIN-93G solid diet prepared by using corn oil (accounting for 5% of the total diet weight) as the fat component was used as the standard diet (hereinafter referred to as standard diet C); the corn oil component in standard diet C was totally replaced by krill oil to prepare a solid diet (hereinafter referred to as 5% krill diet C) and the effect of ingesting 5% krill diet C was investigated. Analysis of the fatty acid composition was outsourced to JAPAN FOOD RESEARCH LABORATORIES. The fatty acid composition of these diets were in substantial agreement with those of standard powder diet C and krill powder diet C which are set forth in Table 4. As in Test Example 1, experimental mice at 6 weeks after birth were fed on standard diet C or 5% krill diet C for 6 weeks.

TABLE 4

Fatty Acid Composition of Each Diet (%)

| Fatty acid | Standard powder diet (5% corn oil) | 5% Krill powder diet C (0% corn oil) | 2% Fish oil powder diet C (3% corn oil) |
|---|---|---|---|
| 12:0 | 0 | 0.3 | 0 |
| 14:0 | 0.4 | 11.5 | 2.2 |
| 15:0 | 0 | 0.5 | 0.1 |
| 16:0 | 11.7 | 21.7 | 9.8 |
| 17:0 | 0.1 | 2.5 | 0.1 |
| 18:0 | 2.2 | 1.6 | 1.6 |
| 20:0 | 0.4 | 0 | 0.3 |
| 22:0 | 0.1 | 0.1 | 0.1 |
| 24:0 | 0.1 | 0 | 0 |
| Total of saturated fatty acids | 15.0 | 38.2 | 14.3 |
| 14:1 | 0 | 0.2 | 0 |
| 16:1 | 0.2 | 7.1 | 3.4 |
| 17:1 | 0 | 0.3 | 0 |
| 18:1 | 29.0 | 18.5 | 21.9 |
| 20:1 | 0.3 | 1.2 | 0.3 |
| 22:1 | 0 | 0.7 | 0.3 |
| Total of monounsaturated fatty acids | 29.5 | 27.9 | 25.8 |
| 16:2 | 0 | 0 | 0 |
| 16:4 | 0 | 0 | 0 |
| 18:2n-6 | 53.9 | 2.5 | 34.9 |
| 18:3n-3 | 0.9 | 1.2 | 1.0 |
| 18:4n-3 | 0 | 3.2 | 1.8 |
| 20:3n-3 | 0 | 0.1 | 0 |
| 20:4n-6 | 0 | 0.2 | 0.4 |
| 20:4n-3 | 0 | 0.4 | 0.4 |
| 20:5n-3 | 0 | 13.8 | 10.2 |
| 21:5n-3 | 0 | 0 | 0 |
| 22:5n-3 | 0 | 0.4 | 0.9 |
| 22:6n-3 | 0 | 6.6 | 4.7 |
| Total of polyunsaturated fatty | 54.8 | 28.5 | 54.3 |
| unknown | 0.7 | 5.2 | 5.5 |

Figure 2:
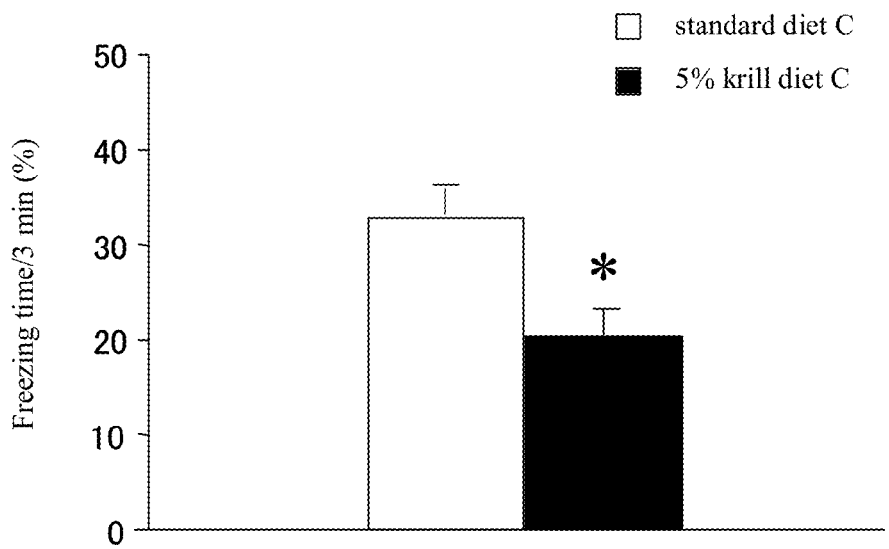
FIG. 2 is a graph showing the effect of 6-week feeding of 5% krill solid diet C on the freezing response of mice in a fear conditioning experiment; the standard diet fed group consisted of 8 animals whereas the krill diet fed group consisted of 9 animals; the vertical axis represents the freezing time in a 3-min period; all values refer to mean±standard error; and * indicates the presence of a significant difference.

These mice were subjected to a fear conditioning test as in Example 2; the result is shown in FIG. 2. A group of mice fed on 5% krill diet C (9 animals/group) showed a shorter freezing time than a group of mice fed on standard diet C (8 animals/group) (FIG. 2). Upon a two-tailed Student's t-test, a significant difference was observed between the data sets for the two groups at p=0.013. These results suggest that regardless of the fat component in the standard diet (whether it was corn oil or soy oil), the formation of fear memory is alleviated by replacing the fat component with krill oil.

Test Example 3

Fear Conditioning Test (3)

In this test, to investigate how the shape of diet would affect the action of krill oil, the diets used in Test Example 2 were prepared in powder form (hereinafter referred to as standard powder diet C and 5% hill powder diet C) and an experiment was performed by feeding these diets to mice. In this experiment, experimental mice at 6 weeks after birth were fed on standard powder diet C or 5% hill powder diet C for 4 weeks.

Figure 3:
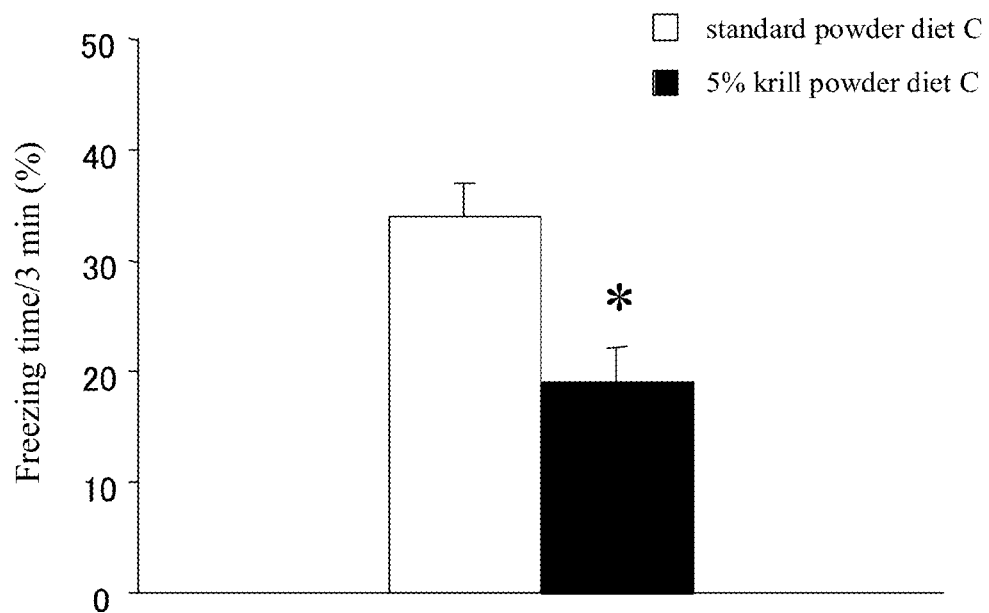
FIG. 3 is a graph showing the effect of 4-week feeding of 5% powdered krill diet C on the freezing response of mice in a fear conditioning experiment; each group consisted of 10 animals; the vertical axis represents the freezing time in a 3-min period; all values refer to mean±standard error; and * indicates the presence of a significant difference.

These mice were subjected to a fear conditioning test as in Test Example 2; the result is shown in FIG. 3. A group of mice fed on 5% hill powder diet C (10 animals/group) showed a shorter freezing time than a group of mice fed on standard powder diet C (10 animals/group) (FIG. 3). Upon a two-tailed Student's t-test, a significant difference was observed between the data sets for the two groups at $p<0.01$.

The above results show that the action of krill oil for alleviating the formation of fear memory is exhibited independently of the shape of the diet (solid or powder). In addition, although the process of producing solid diets involves heating at 80° C. for 30-40 minutes in the drying step, the results of the present study suggest that there is no influence of heating the diet at 80° C.

Test Example 4

Fear Conditioning Test Using Fish Oil

In this test, it was investigated whether fish oil also has an action for alleviating fear memory. To this end, standard powder diet C was modified by replacing 40% of its corn oil component with sardine extracted oil to prepare fish oil powder diet C (sardine oil accounting for 2% of the total diet weight+corn oil accounting for 3% of the total diet weight). As the result of this replacement, the contents of DHA and EPA (eicosapentaenoic acid) in the diet became comparable to those in 5% hill containing powder diet C. Experimental mice at 6 weeks after birth were fed on standard powder diet C or fish oil powder diet C for 4 weeks. The fatty acid composition of each diet is shown in Table 4.

Figure 4:
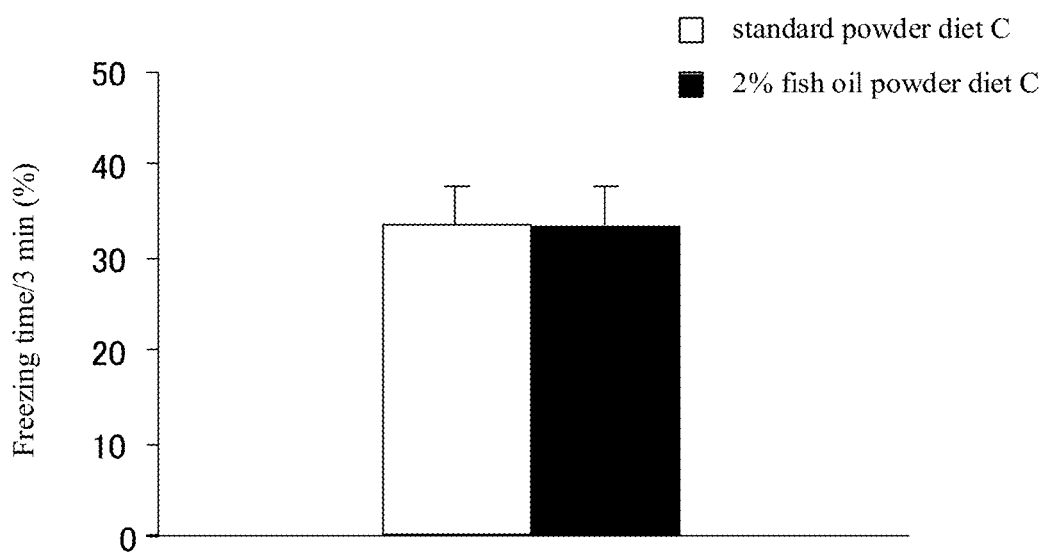
FIG. 4 shows the effect of 4-week feeding of fish oil diet C on the freezing response of mice in a fear conditioning experiment; each group consisted of 10 animals; the vertical axis represents the freezing time in a 3-min period; all values refer to mean±standard error.

These mice were subjected to a fear conditioning test as in Test Example 3; the result is shown in FIG. 4. There was little difference in freezing time between the mouse group fed on standard powder diet (10 animals/group) and the mouse group fed on fish oil powder diet (10 animals/group). This result shows that the fish oil incorporating diet which contains EPA and DHA in comparable amounts to the krill oil incorporating diet does not have the fear memory alleviating action exhibited by the krill oil incorporating diet.

Test Example 5

Open Field Test and Light/Dark Box Test

In the present invention, it was investigated whether the 5% krill diet would affect behaviors other than that derived from fear memory by examining the motility and anxiety affect of mice.

Figure 5:
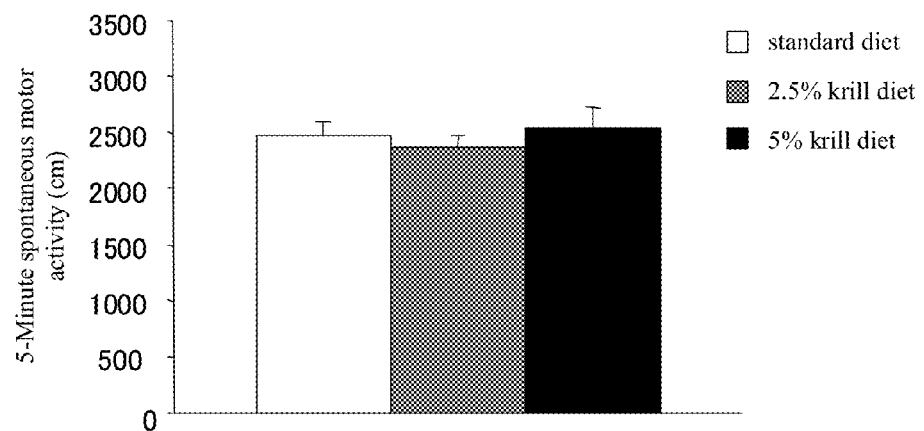
FIG. 5 is a graph showing the result of an open field test with mice fed on 5% krill diet for 6 weeks; each group consisted of 12 animals; the vertical axis represents the spontaneous motor activity in a 5-min period; all values refer to mean±standard error.
Figure 6:
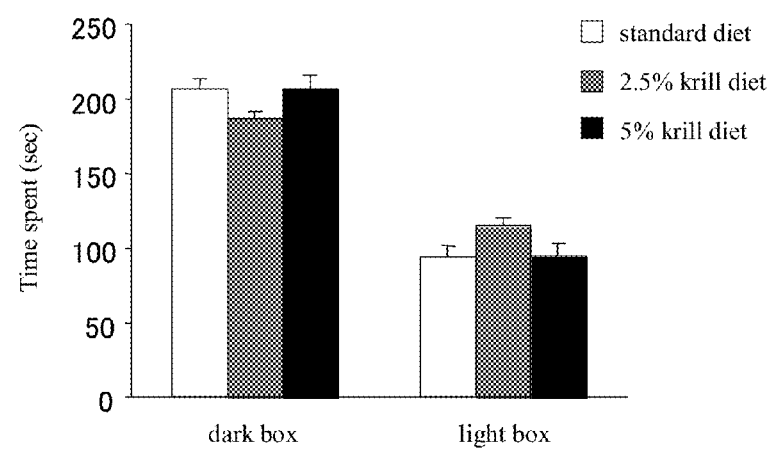
FIG. 6 is a graph showing the result of a light/dark box test with mice fed on 5% krill diet for 6 weeks; each group consisted of 12 animals; the vertical axis represents the time spent by mice in each of the dark and light boxes in a 5-min test period; all values refer to mean±standard error.

The motility of mice was assessed by an open field test (J Neurosci 27 158-166, 2007) in terms of the 5-min spontaneous motor activity (FIG. 5) whereas the anxiety affect was assessed by a light/dark box test (Mol Psychiatry 7 113-117, 2002) in terms of the time spent by mice in the light box (FIG. 6). It is generally held that a mouse in a state of low anxiety will spend a longer time in the light box.

The group fed on the standard diet and the group fed on the 5% krill diet for 6 weeks had no significant differences in these items of assay.

Test Example 6

Pain Sensitivity Test

In the present invention, it was also investigated whether the krill diet would affect the sensitivity of mice for pain. The fear conditioning experiment involves conditioning of mice by inflicting the pain of an electric shock. Therefore, if the pain sensitivity of mice is considerably lowered by ingestion of the krill diet, the formation of fear memory may potentially be reduced.

Figure 7:
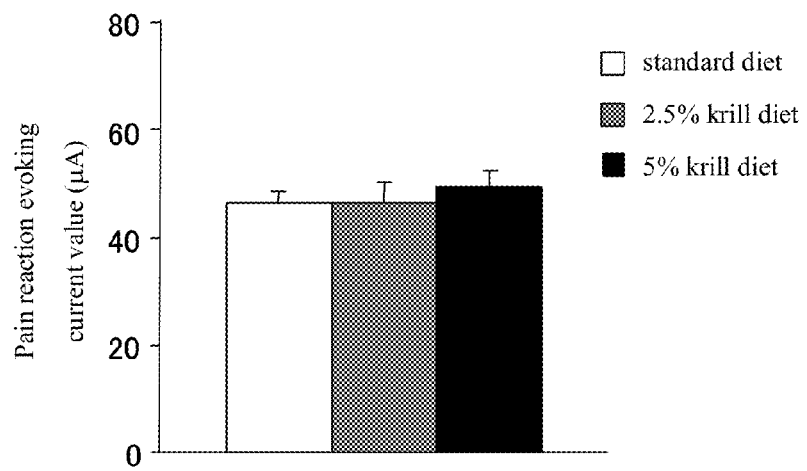
FIG. 7 is a graph showing the effect of ingestion of krill diet on the pain sensitivity of mice; each group consisted of 12 animals; the vertical axis represents the value of an electric current that caused a pain reaction in the mice; all values refer to mean±standard error.

FIG. 7 shows the result of measuring threshold values at which the application of an electric current from the floor grid used in fear conditioning evoked a pain reaction in the mice (Pharmacol Biochem Behav 96 363-369, 2010.) The pain reaction of a mouse was the pulling up of a hind leg in response to the application of an electric current. As shown in FIG. 7, the standard diet group and the krill diet group had no significant difference in the threshold current value that evoked a pain reaction.

Test Example 7

Y-Maze Test

Subsequently, the effect of the krill diet on learning behavior was investigated using a Y-maze test, an evaluation system for spontaneous motor activity and spatial working memory. The maze test was performed in accordance with the method of Suter et al. (Psychopharmacology, 1988, 94, 491-495). A Y-shaped maze consisting of three gray PVC arms (each arm was 40 cm long, 5 cm wide, and 12 cm high) was used. The mouse was placed at the end of either one arm and allowed to freely explore the maze for 8 minutes. The number of times the mouse entered each arm was recorded. When all four limbs were within an arm, the mouse was considered to have entered that arm. After the test, the percentage of alternation was calculated for each mouse by the following formulas:

Percent alternation=(Number of alternation/maximum number of alternation)×100

Maximum number of alternation=(Total number of arm entries)−1

Spontaneous motor activity is expressed by the total number of arm entries. Spatial working memory is short-term memory which enables a mouse to memorize the order of previous arm entries in order to avoid repeated entry into the same arm.

Results

Figure 8:
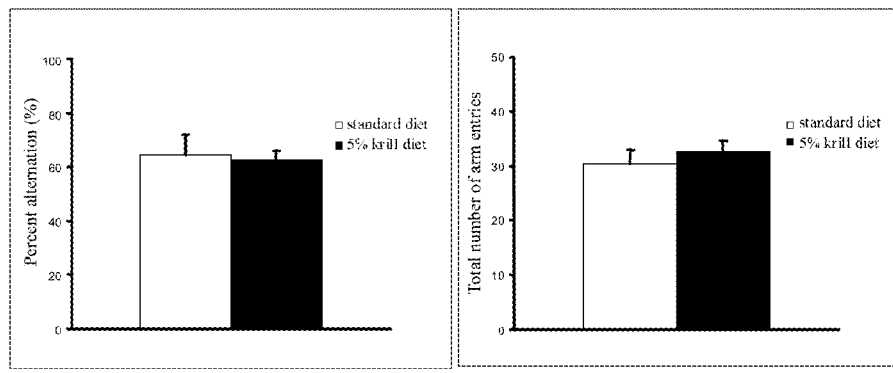
FIG. 8 graphically shows the effect of 6-week feeding of AIN-93G modified 2% sardine oil solid diet on a Y-maze test; each group consisted of 12 animals; all values refer to mean±standard error; the vertical axis of the graph on the left represents the percentage of alternation, and that of the graph on the right represents the total number of arm entries.

As shown in FIG. 8, no significant change was observed between the control diet group and the krill diet group in terms of both the total number of arm entries and the percentage of alternation. This suggests that ingestion of the krill diet for 6 weeks does not affect the spontaneous motor activity and spatial working memory of mice and the krill diet is considered to cause no adverse effect on learning behavior, as exemplified by amnesia.

Test Example 8

Fatty Acid Composition of Serum, Cerebral Cortex, and Hippocampus

Mice were allowed to ingest the 5% krill diet for 6 weeks and thereafter the fatty acids in their serum, cerebral cortex, and hippocampus were quantified. The fatty acid composition of serum, cerebral cortex, and hippocampus was determined in accordance with the method of Liparge G. and Roy C. C. (J. Lipid Res., 27, 114-120, 1986.) To be more specific, serum (50 µL) was added to 4:1 methanol/hexane (2 mL) and, under stirring, tricosanoic acid (C23:0, Tokyo Chemical Industry Co., Ltd, 40 µg) was added as an internal standard. After slowly adding acetyl chloride (200 µL), the mixture was incubated at 80° C. for an hour to complete the reaction; the mixture was then placed in ice, to which 6% potassium carbonate (5 mL) was added and the mixture was stirred for one minute; subsequently, the mixture was centrifuged at 4000 rpm for 10 minutes at 4° C. and hexane in the upper layer was recovered into a gas chromatographic vial and, after being concentrated and purged with argon gas, subjected to measurement by gas chromatography (Agilent Technologies 6890N) under the following conditions.

Column: DB-WAX (Agilent Technologies)
30 m×0.25 mm ID, 0.25 µm film thickness
Carrier gas: He, 1.0 mL/min
Injection port: 250° C., 1 mL, Split (1:30)
Detector: 250° C., FID In the case of the cerebral cortex, a tissue weighing about 70-90 mg was prepared and, after adding methanol-hexane (4 mL), it was homogenized and then cis-13,16,19-docosatrienoic acid methyl ester (C22:3 n-3, Sigma-Aldrich, 640 µg) was added as an internal standard. A 2-mL portion of the homogenate was taken into a glass tube and after slowly adding acetyl chloride (200 µL), the subsequent processing was performed as in the case of the serum.

In the case of the hippocampus, a tissue weighing about 10-20 mg was prepared and, after adding methanol-hexane (2.2 mL), it was homogenized and then cis-13,16,19-docosatdrienoic acid methyl ester (C22:3 n-3, Sigma-Aldrich, 115 µg) was added as an internal standard. A 2-mL portion of the homogenate was taken into a glass tube and after slowly adding acetyl chloride (200 µt), the subsequent processing was performed as in the case of the serum.

The results are shown in Tables 5-7.

TABLE 5

Quantified Values of Fatty Acids in Serum (µg/ml)

| Fatty acid | Standard diet | 2.5% Krill diet | 5% krill diet |
|---|---|---|---|
| C16:0 | 479.7 ± 77.1 | 515.4 ± 108.3 | 539.7 ± 60.5 |
| C16:1n-7 | 51.8 ± 12.3 | 85.6 ± 24.7 | 127.1 ± 17.2** |
| C18:0 | 80.2 ± 12.4 | 75.0 ± 16.6 | 114.4 ± 17.4* |
| C18:1n-9 | 262.9 ± 73.9 | 296.6 ± 76.9 | 313.5 ± 47.4 |
| C18:2n-6 | 627.5 ± 118.9 | 688.2 ± 143.1 | 504.8 ± 73.7 |
| AA | 384.1 ± 30.6 | 169.4 ± 25.6 | 66.3 ± 7.9** |
| EPA | 10.8 ± 1.8 | 95.9 ± 17.6 | 213.1 ± 33.8** |
| DHA | 159.1 ± 24.2 | 220.1 ± 30.7 | 254.2 ± 28.0** |

All values are mean ± standard deviation (n = 6).
With significant difference from the standard diet at *P < 0.05 and **P < 0.01 (Kruskal-Wallis-Dunn test).

TABLE 6

Quantified Values of Fatty Acids in Cerebral Cortex (µg/mg tissue)

| Fatty acid | Standard diet | 2.5% Krill diet | 5% krill diet |
|---|---|---|---|
| C16:0 | 10.5 ± 0.4 | 10.4 ± 0.1 | 10.5 ± 0.4 |
| C16:1 | 0.3 ± 0.0 | 0.3 ± 0.0 | 0.3 ± 0.0** |
| C18:0 | 11.0 ± 0.3 | 10.9 ± 0.1 | 10.8 ± 0.4 |
| C18:1 | 6.9 ± 0.3 | 6.9 ± 0.1 | 7.2 ± 0.4 |
| AA | 5.4 ± 0.2 | 4.6 ± 0.2 | 4.0 ± 0.2** |
| DHA | 9.5 ± 0.5 | 9.9 ± 0.2 | 10.3 ± 0.4* |

All values are mean ± standard deviation (n = 6).
With significant difference from the standard diet at *P < 0.05 and **P < 0.01 (Kruskal-Wallis-Dunn test).

TABLE 7

Quantified Values of Fatty Acids in Hippocampus (µg/mg tissue)

| Fatty acid | Standard diet | 2.5% Krill diet | 5% krill diet |
|---|---|---|---|
| C16:0 | 10.4 ± 0.4 | 10.7 ± 0.8 | 10.7 ± 0.5 |
| C16:1n-7 | 0.3 ± 0.0 | 0.3 ± 0.1 | 0.3 ± 0.0* |
| C18:0 | 11.0 ± 0.9 | 11.3 ± 0.8 | 11.4 ± 0.6 |
| C18:1n-9 | 6.7 ± 0.3 | 7.2 ± 0.4 | 7.7 ± 0.7* |
| AA | 6.0 ± 0.2 | 5.3 ± 0.5 | 4.6 ± 0.2** |
| DHA | 8.1 ± 0.3 | 8.7 ± 0.5 | 9.2 ± 0.4** |

All values are mean ± standard deviation (n = 6).
With significant difference from the standard diet at *P < 0.05 and **P < 0.01 (Kruskal-Wallis-Dunn test).

The relative values (Area %) in the mouse serum, cerebral cortex and hippocampus as measured by gas chromatography under the conditions set forth above, with the chromatographic area values of total fatty acids being taken as 100%, and quantified values (µg/ml) for fatty acids are shown in Tables 8-10 side by side. For C16:0 and C18:0, Table 5 quote different values than Table 8 and the reason is as follows: in Table 5, the chromatographic peaks for C16:0 and C18:0 potentially involved noise from the container, so a blank sample (container only) was subjected to the preliminary treatment described in Test Example 8 and the chromatographic values for the resulting GC sample were subtracted; the amount of the noise, however, was uncertain and not corrected in Table 8.

TABLE 8

Relative Values (Area %) for Fatty Acid Composition and Quantified Values (µg/ml) for Fatty Acid in Serum

| Serum | Control group | | | | 2.5% Krill oil | | | | 5% Krill oil | | | |
|---|---|---|---|---|---|---|---|---|---|---|---|---|
| FA | av (%) | s.e.(%) | av (µg/ml) | s.e.(µg/ml) | av (%) | s.e.(%) | av (µg/ml) | s.e.(µg/ml) | av (%) | s.e.(%) | av (µg/ml) | s.e.(µg/ml) |
| 12:0 | 0.02 | 0.02 | 0.50 | 0.50 | 0.09 | 0.03 | 2.32 | 0.75 | 0.13 | 0.01 | 3.57 | 0.17 |
| 14:0 | 0.43 | 0.01 | 11.02 | 0.66 | 0.64 | 0.02 | 17.31 | 1.37 | 0.91 | 0.02 | 24.72 | 1.24 |
| 14:1 | 0.00 | 0.00 | 0.00 | 0.00 | 0.00 | 0.00 | 0.00 | 0.00 | 0.00 | 0.00 | 0.00 | 0.00 |
| 16:0 | 23.39 | 0.13 | 599.61 | 31.46 | 23.53 | 0.18 | 635.29 | 44.21 | 24.30 | 0.20 | 659.59 | 24.68 |
| 16:1n-7 | 2.00 | 0.10 | 51.82 | 5.03 | 3.12 | 0.19 | 85.58 | 10.09 | 4.68 | 0.19 | 127.08 | 7.01 |
| 18:0 | 12.31 | 0.66 | 311.37 | 5.06 | 11.55 | 0.64 | 306.09 | 6.77 | 12.80 | 0.46 | 345.54 | 7.08 |
| 18:1n-9 | 10.06 | 0.68 | 262.88 | 30.19 | 10.84 | 0.48 | 296.54 | 31.40 | 11.50 | 0.29 | 313.49 | 19.35 |
| 18:1n-7 | 1.62 | 0.05 | 41.92 | 3.66 | 1.78 | 0.07 | 48.57 | 5.00 | 1.90 | 0.06 | 52.00 | 3.45 |
| 18:2n-6 | 24.29 | 0.67 | 627.45 | 48.56 | 25.36 | 0.53 | 688.22 | 58.40 | 18.55 | 0.61 | 504.84 | 30.08 |
| 18:3n-6 | 0.67 | 0.03 | 17.40 | 1.43 | 0.46 | 0.02 | 12.46 | 0.92 | 0.27 | 0.02 | 7.33 | 0.64 |
| 18:3n-3 | 0.73 | 0.06 | 19.20 | 2.41 | 0.80 | 0.06 | 22.05 | 3.12 | 0.70 | 0.05 | 19.27 | 1.89 |
| 20:0 | 0.16 | 0.01 | 4.00 | 0.12 | 0.17 | 0.01 | 4.54 | 0.25 | 0.15 | 0.03 | 4.10 | 0.84 |
| 20:1n-9 | 0.25 | 0.02 | 6.53 | 0.95 | 0.33 | 0.03 | 9.21 | 1.34 | 0.37 | 0.10 | 10.31 | 3.09 |
| 20:2n-6 | 0.00 | 0.00 | 0.00 | 0.00 | 0.00 | 0.00 | 0.00 | 0.00 | 0.00 | 0.00 | 0.00 | 0.00 |
| 20:3n-6 | 0.51 | 0.03 | 12.96 | 0.98 | 0.81 | 0.07 | 22.15 | 2.80 | 0.51 | 0.17 | 14.37 | 5.14 |
| 20:4n-6 | 15.12 | 0.67 | 384.05 | 12.50 | 6.34 | 0.32 | 169.44 | 10.46 | 2.45*** | 0.13 | 66.25*** | 3.24 |
| 20:5n-3 | 0.42 | 0.02 | 10.80 | 0.73 | 3.56 | 0.15 | 95.94 | 7.19 | 7.86*** | 0.46 | 213.04*** | 13.79 |

TABLE 8-continued

Relative Values (Area %) for Fatty Acid Composition and Quantified Values (μg/ml) for Fatty Acid in Serum

| Serum | Control group | | | | 2.5% Krill oil | | | | 5% Krill oil | | | |
|---|---|---|---|---|---|---|---|---|---|---|---|---|
| FA | av (%) | s.e.(%) | av (μg/ml) | s.e.(μg/ml) | av (%) | s.e.(%) | av (μg/ml) | s.e.(μg/ml) | av (%) | s.e.(%) | av (μg/ml) | s.e.(μg/ml) |
| 22:0 | 0.17 | 0.04 | 4.30 | 0.88 | 0.24 | 0.02 | 6.21 | 0.31 | 0.23 | 0.02 | 6.11 | 0.31 |
| 22:4n-6 | 0.00 | 0.00 | 0.00 | 0.00 | 0.00 | 0.00 | 0.00 | 0.00 | 0.00 | 0.00 | 0.00 | 0.00 |
| 22:5n-3 | 0.34 | 0.01 | 8.83 | 0.68 | 0.66 | 0.02 | 17.84 | 1.37 | 0.93 | 0.03 | 25.46 | 1.72 |
| 22:6n-3 | 6.23 | 0.27 | 159.14 | 9.89 | 8.19 | 0.16 | 220.13 | 12.52 | 9.36*** | 0.19 | 254.24** | 11.44 |
| 24:1 | 0.00 | 0.00 | 0.00 | 0.00 | 0.00 | 0.00 | 0.00 | 0.00 | 0.00 | 0.00 | 0.00 | 0.00 |

(n = 6)
With significant difference from the standard diet at $P < 0.01$ and *$P < 0.001$ (Kruskal-Wallis-Dunn test); the test was performed on arachidonic acid, eicosapentaenoic acid, and docosahexaenoic acid.

TABLE 9

Relative Values (Area %) for Fatty Acid Composition and Quantified Values (μg/ml) for Fatty Acid in Cerebral Cortex

| Cerebral cortex FA | Control group | | | | 2.5% Krill oil | | | | 5% Krill oil | | | |
|---|---|---|---|---|---|---|---|---|---|---|---|---|
| | av (%) | s.e. (%) | av (μg/mg) | s.e. (μg/mg) | av (%) | s.e. (%) | av (μg/mg) | s.e. (μg/mg) | av (%) | s.e. (%) | av (μg/mg) | s.e. (μg/mg) |
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.12 | 0.00 | 0.06 | 0.00 | 0.13 | 0.00 | 0.07 | 0.00 | 0.12 | 0.02 | 0.06 | 0.01 |
| 16:0 | 19.64 | 0.14 | 10.52 | 0.14 | 19.79 | 0.07 | 10.35 | 0.04 | 20.06 | 0.18 | 10.52 | 0.17 |
| 16:1n-7 | 0.50 | 0.00 | 0.27 | 0.00 | 0.56 | 0.01 | 0.29 | 0.00 | 0.63 | 0.03 | 0.33 | 0.02 |
| 18:0 | 20.60 | 0.14 | 11.04 | 0.11 | 20.74 | 0.06 | 10.85 | 0.06 | 20.52 | 0.12 | 10.76 | 0.17 |
| 18:1n-9 | 12.87 | 0.03 | 6.90 | 0.13 | 13.17 | 0.05 | 6.89 | 0.06 | 13.65 | 0.13 | 7.17 | 0.17 |
| 18:1n-7 | 3.54 | 0.02 | 1.90 | 0.03 | 3.49 | 0.02 | 1.83 | 0.02 | 3.57 | 0.03 | 1.88 | 0.04 |
| 18:2n-6 | 0.60 | 0.01 | 0.32 | 0.01 | 0.52 | 0.01 | 0.27 | 0.01 | 0.35 | 0.01 | 0.18 | 0.00 |
| 18:3n-6 | 0.00 | 0.00 | 0.00 | 0.00 | 0.00 | 0.00 | 0.00 | 0.00 | 0.00 | 0.00 | 0.00 | 0.00 |
| 18:3n-3 | 0.00 | 0.00 | 0.00 | 0.00 | 0.00 | 0.00 | 0.00 | 0.00 | 0.00 | 0.00 | 0.00 | 0.00 |
| 20:0 | 0.28 | 0.00 | 0.15 | 0.00 | 0.52 | 0.09 | 0.27 | 0.05 | 0.64 | 0.18 | 0.33 | 0.09 |
| 20:1n-9 | 0.00 | 0.00 | 0.00 | 0.00 | 0.00 | 0.00 | 0.00 | 0.00 | 0.00 | 0.00 | 0.00 | 0.00 |
| 20:2n-6 | 0.93 | 0.36 | 0.51 | 0.20 | 0.14 | 0.13 | 0.07 | 0.07 | 0.02 | 0.02 | 0.01 | 0.01 |
| 20:3n-6 | 0.45 | 0.01 | 0.24 | 0.01 | 0.66 | 0.01 | 0.35 | 0.01 | 0.69 | 0.12 | 0.36 | 0.07 |
| 20:4n-6 | 10.02 | 0.07 | 5.37 | 0.07 | 8.86 | 0.10 | 4.63 | 0.06 | 7.69*** | 0.17 | 4.03*** | 0.07 |
| 20:3n-3 | 0.00 | 0.00 | 0.00 | 0.00 | 0.00 | 0.00 | 0.00 | 0.00 | 0.00 | 0.00 | 0.00 | 0.00 |
| 20:5n-3 | 0.00 | 0.00 | 0.00 | 0.00 | 0.16 | 0.01 | 0.09 | 0.01 | 0.35 | 0.01 | 0.19 | 0.01 |
| 22:0 | 0.25 | 0.00 | 0.14 | 0.00 | 0.28 | 0.02 | 0.14 | 0.01 | 0.26 | 0.02 | 0.14 | 0.01 |
| 22:1n-9 | 0.11 | 0.00 | 0.06 | 0.00 | 0.10 | 0.00 | 0.05 | 0.00 | 0.07 | 0.02 | 0.04 | 0.01 |
| 22:2n-6 | 0.02 | 0.02 | 0.01 | 0.01 | 0.00 | 0.00 | 0.00 | 0.00 | 0.04 | 0.03 | 0.02 | 0.01 |
| 22:4n-6 | 2.27 | 0.04 | 1.22 | 0.02 | 1.74 | 0.06 | 0.91 | 0.03 | 1.40 | 0.07 | 0.73 | 0.03 |
| 22:5n-3 | 0.13 | 0.03 | 0.07 | 0.01 | 0.39 | 0.02 | 0.20 | 0.01 | 0.60 | 0.02 | 0.31 | 0.01 |
| 24:0 | 0.48 | 0.01 | 0.26 | 0.01 | 0.48 | 0.01 | 0.25 | 0.00 | 0.44 | 0.02 | 0.23 | 0.01 |
| 22:6n-3 | 17.77 | 0.20 | 9.52 | 0.20 | 18.90 | 0.10 | 9.89 | 0.06 | 19.64*** | 0.27 | 10.3* | 0.18 |
| 24:1 | 1.13 | 0.02 | 0.61 | 0.01 | 1.09 | 0.02 | 0.57 | 0.01 | 1.00 | 0.05 | 0.52 | 0.03 |

(n = 6)
With significant difference from the standard diet at *$P < 0.05$, $P < 0.01$ and *$P < 0.001$ (Kruskal-Wallis-Dunn test); the test was performed on arachidonic acid and docosahexaenoic acid.

TABLE 10

Relative Values (Area %) for Fatty Acid Composition and Quantified Values (μg/ml) for Fatty Acid in Hippocampus

| Hippo-campus FA | Control group | | | | 2.5% Krill oil | | | | 5% Krill oil | | | |
|---|---|---|---|---|---|---|---|---|---|---|---|---|
| | av (%) | s.e. (%) | av (μg/mg) | s.e. (μg/mg) | av (%) | s.e. (%) | av (μg/mg) | s.e. (μg/mg) | av (%) | s.e. (%) | av (μg/mg) | s.e. (μg/mg) |
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.00 | 0.00 | 0.00 | 0.00 | 0.03 | 0.03 | 0.02 | 0.02 | 0.00 | 0.00 | 0.00 | 0.00 |
| 16:0 | 19.89 | 0.19 | 10.40 | 0.15 | 19.99 | 0.33 | 10.69 | 0.31 | 19.74 | 0.12 | 10.74 | 0.20 |
| 16:1n-7 | 0.49 | 0.01 | 0.26 | 0.01 | 0.58 | 0.04 | 0.31 | 0.02 | 0.56 | 0.02 | 0.31 | 0.01 |
| 18:0 | 21.08 | 0.11 | 11.03 | 0.16 | 21.08 | 0.17 | 11.27 | 0.31 | 20.87 | 0.07 | 11.36 | 0.23 |
| 18:1n-9 | 12.86 | 0.14 | 6.73 | 0.14 | 13.50 | 0.13 | 7.21 | 0.17 | 14.03 | 0.21 | 7.65 | 0.28 |
| 18:1n-7 | 3.80 | 0.04 | 1.99 | 0.04 | 3.75 | 0.02 | 2.01 | 0.05 | 3.85 | 0.05 | 2.10 | 0.07 |
| 18:2n-6 | 0.56 | 0.01 | 0.29 | 0.01 | 0.36 | 0.12 | 0.19 | 0.06 | 0.23 | 0.07 | 0.13 | 0.04 |
| 18:3n-6 | 0.03 | 0.03 | 0.02 | 0.02 | 0.03 | 0.03 | 0.02 | 0.02 | 0.09 | 0.04 | 0.05 | 0.02 |
| 18:3n-3 | 0.00 | 0.00 | 0.00 | 0.00 | 0.00 | 0.00 | 0.00 | 0.00 | 0.00 | 0.00 | 0.00 | 0.00 |
| 20:0 | 0.25 | 0.01 | 0.13 | 0.00 | 0.32 | 0.06 | 0.17 | 0.04 | 0.25 | 0.01 | 0.14 | 0.01 |
| 20:1n-9 | 0.88 | 0.07 | 0.46 | 0.04 | 0.76 | 0.16 | 0.41 | 0.09 | 0.96 | 0.08 | 0.52 | 0.05 |

TABLE 10-continued

Relative Values (Area %) for Fatty Acid Composition and
Quantified Values (μg/ml) for Fatty Acid in Hippocampus

| Hippo-campus FA | Control group | | | | 2.5% Krill oil | | | | 5% Krill oil | | | |
|---|---|---|---|---|---|---|---|---|---|---|---|---|
| | av (%) | s.e. (%) | av (μg/mg) | s.e. (μg/mg) | av (%) | s.e. (%) | av (μg/mg) | s.e. (μg/mg) | av (%) | s.e. (%) | av (μg/mg) | s.e. (μg/mg) |
| 20:2n-6 | 0.00 | 0.00 | 0.00 | 0.00 | 0.11 | 0.05 | 0.06 | 0.03 | 0.14 | 0.05 | 0.08 | 0.03 |
| 20:3n-6 | 0.44 | 0.00 | 0.23 | 0.01 | 0.65 | 0.02 | 0.35 | 0.01 | 0.55 | 0.00 | 0.30 | 0.01 |
| 20:4n-6 | 11.41 | 0.11 | 5.97 | 0.09 | 9.94 | 0.22 | 5.32 | 0.21 | 8.53*** | 0.20 | 4.63** | 0.08 |
| 20:3n-3 | 0.00 | 0.00 | 0.00 | 0.00 | 0.00 | 0.00 | 0.00 | 0.00 | 0.00 | 0.00 | 0.00 | 0.00 |
| 20:5n-3 | 0.00 | 0.00 | 0.00 | 0.00 | 0.08 | 0.05 | 0.04 | 0.03 | 0.40 | 0.03 | 0.22 | 0.01 |
| 22:0 | 0.26 | 0.01 | 0.13 | 0.01 | 0.21 | 0.04 | 0.11 | 0.02 | 0.26 | 0.01 | 0.14 | 0.01 |
| 22:1n-9 | 0.00 | 0.00 | 0.00 | 0.00 | 0.00 | 0.00 | 0.00 | 0.00 | 0.00 | 0.00 | 0.00 | 0.00 |
| 22:2n-6 | 0.00 | 0.00 | 0.00 | 0.00 | 0.00 | 0.00 | 0.00 | 0.00 | 0.00 | 0.00 | 0.00 | 0.00 |
| 22:4n-6 | 2.49 | 0.03 | 1.30 | 0.02 | 1.87 | 0.06 | 1.00 | 0.05 | 1.51 | 0.04 | 0.82 | 0.02 |
| 22:5n-3 | 0.05 | 0.03 | 0.03 | 0.02 | 0.39 | 0.02 | 0.21 | 0.01 | 0.59 | 0.02 | 0.32 | 0.02 |
| 24:0 | 0.38 | 0.03 | 0.20 | 0.01 | 0.36 | 0.07 | 0.19 | 0.04 | 0.43 | 0.03 | 0.23 | 0.02 |
| 22:6n-3 | 15.44 | 0.15 | 8.08 | 0.12 | 16.22 | 0.19 | 8.67 | 0.21 | 16.97*** | 0.12 | 9.23** | 0.17 |
| 24:1 | 1.06 | 0.06 | 0.56 | 0.03 | 0.05 | 0.19 | 0.51 | 0.10 | 1.12 | 0.05 | 0.61 | 0.04 |

(n = 6)
With significant difference from the standard diet at $P < 0.01$ and *$P < 0.001$ (Kruskal-Wallis-Dunn test); the test was performed on arachidonic acid and docosahexaenoic acid.

Table 8 lists the quantified values (μg/ml) of fatty acids in the sera of mice fed on the standard diet and the krill diet for 6 weeks, as well as their relative values (Area %), with the chromatographic area value of total fatty acid being taken as 100%. The fatty acid composition of the sera, reflecting that of diet, showed marked increases in EPA, DHA, and C16:1n-7 (palmitoleic acid) but a considerable decrease in arachidonic acid (AA). Tables 9 and 10 list the quantified values (μg/ml) of fatty acids in the cerebral cortex and hippocampus of mice fed on the standard diet and the krill diet for 6 weeks, as well as their relative values (Area %), with the GC area value of total fatty acid being taken as 100%. In the cerebral cortex and hippocampus, DHA increased significantly whereas AA decreased significantly. In particular, the DHA/AA ratio and the ω3/ω6 ratio (the ratio of the total of ω3 polyunsaturated fatty acids to the total of ω6 polyunsaturated fatty acids) in the cerebral cortex had the following values in the control group, 2.5% krill oil group, and 5% krill oil group, respectively: 1.77, 2.14, and 2.56 (DHA/AA ratio), and 1.26, 1.63, and 2.03 (ω3/ω6 ratio). The present inventors then hypothesized that the mechanism by which the fear memory alleviating action demonstrated in the present study is exhibited would be that the ω3/ω6 ratio in diet exerts considerable effects on the ω3/ω6 ratio or DHA/AA ratio in the blood and brain, and conducted the following experiments to validate this hypothesis.

Test Example 9

Fear Conditioning Test with Krill Oil Diet Supplemented with Linoleic Acid (LA)

Figure 9:
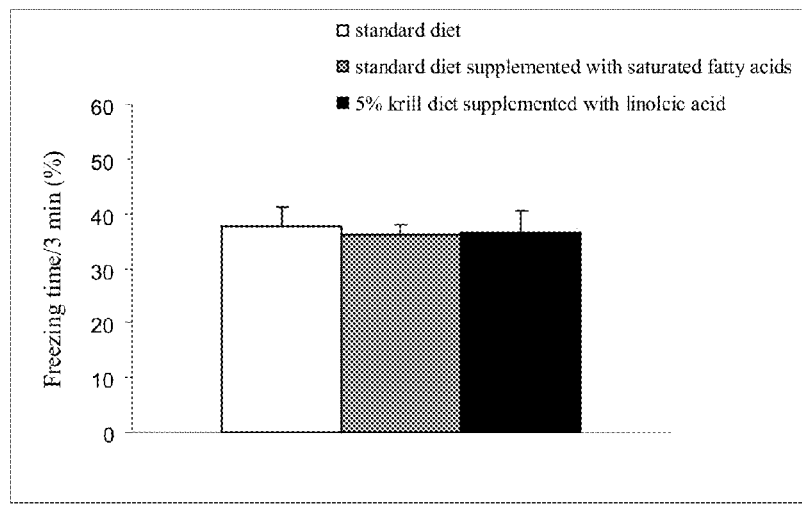
FIG. 9 is a graph showing the effect of added linoleic acid on the effect on the freezing response of mice fed on 5% hill solid diet for 6 weeks in a fear conditioning experiment; each group consisted of 10 animals; the vertical axis represents the freezing time in a 3-min period; all values refer to mean±standard error; and NS indicates the absence of any significant difference.

The standard diet containing 7% soy oil had an ω3/ω6 ratio of 0.12 whereas the 5% krill oil diet had an ω3/ω6 ratio of 1, so in order to make it substantially comparable to the standard diet, linoleic acid (LA) was added to the krill oil diet to adjust its ω3/ω6 ratio in the krill oil diet to a smaller value of 0.32 (with increased ω6.) In the meantime, lauric acid, myristic acid, and palmitic acid (all being saturated fatty acids) were added to the standard diet so as to adjust its lipid content to 9.5%. The fear conditioning test was performed as in Test Example 1. The result of the fear conditioning test is shown in FIG. 9. Analysis of the fatty acid composition was outsourced to JAPAN FOOD RESEARCH LABORATORIES. The ω3/ω6 ratio in diet was 0.12 in the control group and 0.32 in the krill oil+LA group. The fatty acid composition of each diet is shown in Table 11. The fatty acid composition in the serum, cerebral cortex, and hippocampus was measured as in Test Example 8.

TABLE 11

Fatty Acid Composition of Each Diet (%)

| Fatty acid | Standard diet (7% soy oil) | Control diet (supplemented with saturated fatty acids) (7% soy oil) | Krill oil diet (supplemented with linoleic acid) (2% soy oil) |
|---|---|---|---|
| 12:0 | 0 | 13.4 | 0.2 |
| 14:0 | 0.2 | 5.4 | 5.5 |
| 15:0 | 0 | 0 | 0.2 |
| 16:0 | 11.6 | 14.3 | 13.3 |
| 17:0 | 0 | 0 | 1.1 |
| 18:0 | 4.2 | 3.2 | 1.8 |
| 20:0 | 0.3 | 0.3 | 0.1 |
| 22:0 | 0.4 | 0.3 | 0 |
| 24:0 | 0.2 | 0 | 0 |
| Total of saturated fatty acids | 16.9 | 36.9 | 22.2 |
| 14:1 | 0 | 0 | 0 |
| 16:1 | 0 | 0 | 2.8 |
| 17:1 | 0 | 0 | 0.2 |
| 18:1 | 24.3 | 18.5 | 16.5 |
| 20:1 | 0.2 | 0.2 | 0.4 |
| 22:1 | 0 | 0 | 0 |
| Total of monounsaturated fatty acids | 24.5 | 18.7 | 19.9 |
| 16:2 | 0 | 0 | 0.3 |
| 16:3 | 0 | 0 | 0 |
| 16:4 | 0 | 0 | 0.4 |
| 18:2n-6 | 51.6 | 39 | 41.9 |
| 18:3n-3 | 6.3 | 4.8 | 2.1 |
| 18:4n-3 | 0 | 0 | 1.4 |
| 20:4n-6 | 0 | 0 | 0 |
| 20:4n-3 | 0 | 0 | 0.1 |
| 20:5n-3 | 0 | 0 | 6.3 |
| 21:5n-3 | 0 | 0 | 0.2 |
| 22:5n-3 | 0 | 0 | 0.2 |
| 22:6n-3 | 0 | 0 | 3 |
| Total of polyunsaturated fatty acids | 57.9 | 43.8 | 55.9 |

TABLE 11-continued

Fatty Acid Composition of Each Diet (%)

| Fatty acid | Standard diet (7% soy oil) | Control diet (supplemented with saturated fatty acids) (7% soy oil) | Krill oil diet (supplemented with linoleic acid) (2% soy oil) |
|---|---|---|---|
| unknown | 0.7 | 0.6 | 1.7 |
| ω3/ω6 ratio | 0.12 | 0.12 | 0.32 |

Results

The group ingesting the krill oil diet supplemented with linoleic acid (LA) to have its ω3/ω6 ratio lowered to 0.32 was in no way different from the control group in terms of the freezing time (FIG. 9), suggesting the extreme importance of the ω3/ω6 ratio in diet for the development of the desired action. The fatty acid composition in serum, cerebral cortex, and hippocampus is shown in Tables 12-14.

TABLE 12

Relative Values (Area %) for Fatty Acid Composition and Quantified Values (μg/ml) for Fatty Acid in Serum

| Serum | Control group (+SFA) | | | | 5% Krill oil + LA | | | |
|---|---|---|---|---|---|---|---|---|
| FA | av (%) | s.e.(%) | av (μg/ml) | s.e.(μg/ml) | av (%) | s.e.(%) | av (μg/ml) | s.e.(μg/ml) |
| 12:0 | 0.05 | 0.05 | 1.39 | 1.39 | 0.00 | 0.00 | 0.00 | 0.00 |
| 14:0 | 0.59 | 0.03 | 15.27 | 2.20 | 0.65 | 0.04 | 16.79 | 1.12 |
| 16:0 | 20.83 | 0.76 | 549.65 | 80.35 | 21.40 | 0.46 | 552.20 | 17.09 |
| 16:1n-7 | 2.49 | 0.12 | 65.79 | 10.16 | 2.89 | 0.13 | 74.56 | 3.78 |
| 18:0 | 7.33 | 0.52 | 184.02 | 23.85 | 6.28 | 0.21 | 162.53 | 8.47 |
| 18:1n-9 | 11.59 | 0.45 | 305.68 | 45.96 | 9.99 | 0.38 | 259.86 | 19.52 |
| 18:1n-7 | 1.90 | 0.18 | 48.59 | 8.24 | 1.70 | 0.08 | 44.08 | 3.32 |
| 18:2n-6 | 26.49 | 0.91 | 697.80 | 100.68 | 31.73 | 0.49 | 818.56 | 22.68 |
| 18:3n-6 | 0.68 | 0.11 | 18.39 | 4.13 | 0.32 | 0.07 | 7.95 | 1.62 |
| 18:3n-3 | 0.57 | 0.04 | 15.48 | 2.60 | 0.47 | 0.02 | 12.10 | 0.80 |
| 20:1n-9 | 0.26 | 0.09 | 6.16 | 2.31 | 0.23 | 0.08 | 5.88 | 1.93 |
| 20:3n-6 | 1.09 | 0.20 | 27.18 | 6.42 | 1.00 | 0.10 | 25.08 | 2.92 |
| 20:4n-6 | 16.90 | 0.83 | 430.33 | 56.42 | 4.34** | 0.25 | 111.41** | 4.46 |
| 20:5n-3 | 0.47 | 0.02 | 12.38 | 1.80 | 6.22** | 0.33 | 162.03** | 14.13 |
| 22:0 | 0.18 | 0.08 | 3.76 | 1.92 | 0.23 | 0.07 | 6.12 | 1.95 |
| 22:5n-3 | 0.16 | 0.07 | 4.86 | 2.18 | 0.81 | 0.05 | 21.03 | 1.97 |
| 22:6n-3 | 7.02 | 0.11 | 182.80 | 25.01 | 10.33** | 0.16 | 267.59** | 13.10 |

**With significant difference from the control group at P < 0.01 (Mann-Whitney U-test); the test was performed on arachidonic acid, eicosapentaenoic acid, and docosahexaenoic acid.

TABLE 13

Relative Values (Area %) for Fatty Acid Composition and Quantified Values (μg/ml) for Fatty Acid in Cerebral Cortex

| Cerebral cortex | Control group (+SFA) | | | | 5% Krill oil + LA | | | |
|---|---|---|---|---|---|---|---|---|
| FA | av (%) | s.e.(%) | av (μg/mg) | s.e.(μg/mg) | av (%) | s.e.(%) | av (μg/mg) | s.e.(μg/mg) |
| 12:0 | 0.00 | 0.00 | 0.00 | 0.00 | 0.00 | 0.00 | 0.00 | 0.00 |
| 14:0 | 0.15 | 0.00 | 0.05 | 0.00 | 0.15 | 0.00 | 0.04 | 0.00 |
| 16:0 | 20.10 | 0.08 | 6.37 | 0.05 | 20.71 | 0.10 | 6.27 | 0.05 |
| 16:1n-7 | 0.51 | 0.01 | 0.16 | 0.00 | 0.57 | 0.01 | 0.17 | 0.00 |
| 18:0 | 20.26 | 0.09 | 6.42 | 0.05 | 20.17 | 0.05 | 6.11 | 0.05 |
| 18:1n-9 | 12.92 | 0.06 | 4.09 | 0.03 | 13.23 | 0.03 | 4.01 | 0.03 |
| 18:1n-7 | 3.30 | 0.02 | 1.05 | 0.01 | 3.27 | 0.02 | 0.99 | 0.01 |
| 18:2n-6 | 0.77 | 0.05 | 0.24 | 0.02 | 0.77 | 0.03 | 0.23 | 0.01 |
| 18:3n-6 | 0.01 | 0.01 | 0.00 | 0.00 | 0.01 | 0.01 | 0.00 | 0.00 |
| 18:3n-3 | 0.01 | 0.01 | 0.00 | 0.00 | 0.00 | 0.00 | 0.00 | 0.00 |
| 20:0 | 0.27 | 0.00 | 0.09 | 0.00 | 0.25 | 0.00 | 0.08 | 0.00 |
| 20:1n-9 | 1.02 | 0.03 | 0.32 | 0.01 | 0.94 | 0.05 | 0.29 | 0.01 |
| 20:2n-6 | 0.13 | 0.00 | 0.04 | 0.00 | 0.06 | 0.03 | 0.02 | 0.01 |
| 20:3n-6 | 0.43 | 0.01 | 0.14 | 0.00 | 0.65 | 0.01 | 0.20 | 0.00 |
| 20:4n-6 | 10.02 | 0.04 | 3.17 | 0.02 | 8.67** | 0.06 | 2.63** | 0.03 |
| 20:3n-3 | 0.00 | 0.00 | 0.00 | 0.00 | 0.17 | 0.11 | 0.05 | 0.03 |
| 20:5n-3 | 0.57 | 0.26 | 0.18 | 0.08 | 0.20 | 0.02 | 0.06 | 0.01 |
| 22:0 | 0.37 | 0.00 | 0.12 | 0.00 | 0.33 | 0.00 | 0.10 | 0.00 |
| 22:1n-9 | 0.07 | 0.02 | 0.02 | 0.01 | 0.03 | 0.02 | 0.01 | 0.01 |
| 22:2n-6 | 0.07 | 0.02 | 0.02 | 0.01 | 0.00 | 0.00 | 0.00 | 0.00 |
| 22:4n-6 | 2.28 | 0.01 | 0.72 | 0.00 | 1.71 | 0.02 | 0.52 | 0.00 |
| 22:5n-3 | 0.16 | 0.01 | 0.05 | 0.00 | 0.42 | 0.01 | 0.13 | 0.00 |
| 24:0 | 0.42 | 0.01 | 0.13 | 0.00 | 0.37 | 0.01 | 0.11 | 0.00 |

TABLE 13-continued

Relative Values (Area %) for Fatty Acid Composition and Quantified Values (μg/ml) for Fatty Acid in Cerebral Cortex

| Cerebral cortex | Control group (+SFA) | | | | 5% Krill oil + LA | | | |
|---|---|---|---|---|---|---|---|---|
| FA | av (%) | s.e.(%) | av (μg/mg) | s.e.(μg/mg) | av (%) | s.e.(%) | av (μg/mg) | s.e.(μg/mg) |
| 22:6n-3 | 16.55 | 0.07 | 5.24 | 0.03 | 18.18 | 0.07 | 5.51** | 0.06 |
| 24:1 | 0.90 | 0.02 | 0.29 | 0.01 | 0.78 | 0.01 | 0.24 | 0.00 |

**With significant difference from the control group at $P < 0.01$ (Mann-Whitney U-test); the test was performed on arachidonic acid, eicosapentaenoic acid, and docosahexaenoic acid.

TABLE 14

Relative Values (Area %) for Fatty Acid Composition and Quantified Values (μg/ml) for Fatty Acid in Hippocampus

| Hippocampus | Control group (+SFA) | | | | 5% Krill oil + LA | | | |
|---|---|---|---|---|---|---|---|---|
| FA | av (%) | s.e.(%) | av (μg/mg) | s.e.(μg/mg) | av (%) | s.e.(%) | av (μg/mg) | s.e.(μg/mg) |
| 12:0 | 0.00 | 0.00 | 0.00 | 0.00 | 0.00 | 0.00 | 0.00 | 0.00 |
| 14:0 | 0.02 | 0.02 | 0.01 | 0.01 | 0.09 | 0.03 | 0.03 | 0.01 |
| 16:0 | 19.92 | 0.20 | 6.54 | 0.24 | 19.60 | 0.18 | 6.15 | 0.03 |
| 16:1n-7 | 0.50 | 0.01 | 0.16 | 0.01 | 0.53 | 0.01 | 0.17 | 0.00 |
| 18:0 | 20.86 | 0.09 | 6.85 | 0.29 | 20.38 | 0.07 | 6.39 | 0.07 |
| 18:1n-9 | 13.38 | 0.20 | 4.40 | 0.22 | 13.79 | 0.11 | 4.33 | 0.08 |
| 18:1n-7 | 3.33 | 0.04 | 1.10 | 0.05 | 3.20 | 0.06 | 1.00 | 0.02 |
| 18:2n-6 | 0.78 | 0.05 | 0.26 | 0.02 | 0.80 | 0.03 | 0.25 | 0.01 |
| 18:3n-6 | 0.00 | 0.00 | 0.00 | 0.00 | 0.00 | 0.00 | 0.00 | 0.00 |
| 18:3n-3 | 0.00 | 0.00 | 0.00 | 0.00 | 0.00 | 0.00 | 0.00 | 0.00 |
| 20:0 | 0.24 | 0.05 | 0.08 | 0.02 | 0.28 | 0.01 | 0.09 | 0.00 |
| 20:1n-9 | 0.92 | 0.04 | 0.30 | 0.02 | 0.93 | 0.04 | 0.29 | 0.01 |
| 20:2n-6 | 0.03 | 0.03 | 0.01 | 0.01 | 0.09 | 0.03 | 0.03 | 0.01 |
| 20:3n-6 | 0.47 | 0.00 | 0.15 | 0.01 | 0.68 | 0.00 | 0.21 | 0.00 |
| 20:4n-6 | 11.43 | 0.14 | 3.76 | 0.17 | 9.61** | 0.08 | 3.01** | 0.02 |
| 20:3n-3 | 0.12 | 0.08 | 0.04 | 0.03 | 0.43 | 0.24 | 0.14 | 0.08 |
| 20:5n-3 | 0.00 | 0.00 | 0.00 | 0.00 | 0.36 | 0.17 | 0.11 | 0.05 |
| 22:0 | 0.19 | 0.09 | 0.06 | 0.03 | 0.39 | 0.03 | 0.12 | 0.01 |
| 22:1n-9 | 0.00 | 0.00 | 0.00 | 0.00 | 0.02 | 0.02 | 0.01 | 0.01 |
| 22:2n-6 | 0.00 | 0.00 | 0.00 | 0.00 | 0.00 | 0.00 | 0.00 | 0.00 |
| 22:4n-6 | 2.49 | 0.02 | 0.82 | 0.04 | 1.86 | 0.02 | 0.58 | 0.01 |
| 22:5n-3 | 0.03 | 0.03 | 0.01 | 0.01 | 0.44 | 0.01 | 0.14 | 0.00 |
| 24:0 | 0.29 | 0.09 | 0.10 | 0.03 | 0.42 | 0.03 | 0.13 | 0.01 |
| 22:6n-3 | 15.43 | 0.26 | 5.06 | 0.19 | 16.27* | 0.19 | 5.10 | 0.03 |
| 24:1 | 0.91 | 0.06 | 0.30 | 0.03 | 0.94 | 0.05 | 0.29 | 0.02 |

With significant difference from the control group at *$P < 0.05$ and **$P < 0.01$ (Mann-Whitney U-test); the test was performed on arachidonic acid, eicosapentaenoic acid, and docosahexaenoic acid.

Test Example 10

Fear Conditioning Test Using Fish Oil Diet with its ω3/ω6 Ratio Modified

Figure 10:
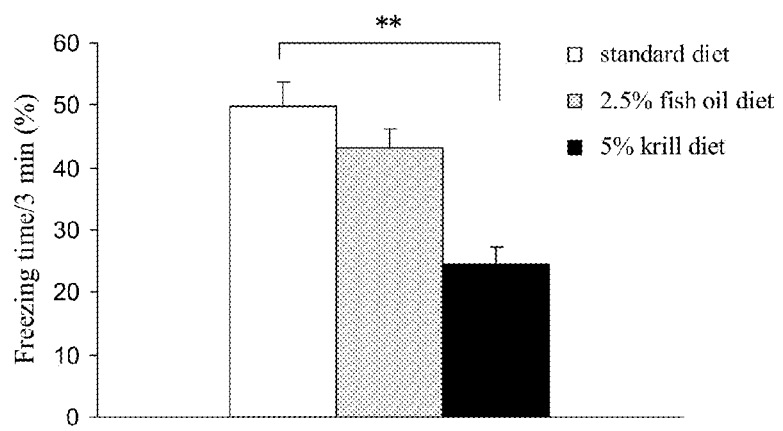
FIG. 10 is a graph showing the effect of 6-week feeding of AIN-93G modified 2.5% sardine oil solid diet on the freezing response of mice in a fear conditioning experiment; each group consisted of 12 animals; the vertical axis represents the freezing time in a 3-min period; all values refer to mean±standard error; and ND indicates the absence of any significant difference; the vertical axis represents the freezing time in a 3-min period; all values refer to mean±standard error; and ** indicates the presence of a significant difference between the control group and the krill oil group at $P<0.01$.
Figure 15:
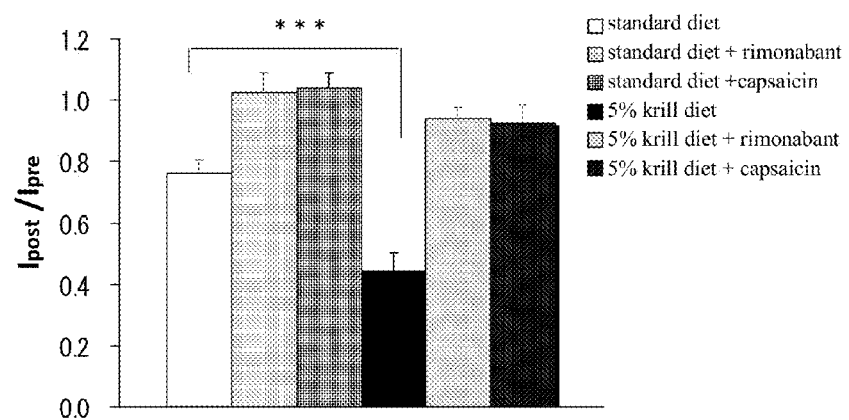
FIG. 15 is a graph showing the ratio of the amplitude after depolarization ($I_{post}$) to the amplitude before depolarization ($I_{pre}$) for excitatory postsynaptic currents from pyramidal cells in the amygdala; all values refer to mean±standard error; and *** indicates the presence of a significant difference between the control group and the krill oil group at $P<0.001$.

First, a fear conditioning test was conducted to investigate the effect of a fish oil diet on fear memory using a soy oil, rather than corn oil, based diet to feed a control group. The method of the fear conditioning test was the same as in Test Example 1. The results of the fear conditioning test are shown in FIG. 10. The control group was fed on an AIN-93G based diet supplemented with 7% soy oil, whereas the fish oil diet was one supplemented with 2.5% sardine oil+4.5% soy oil. As a positive control group, a krill oil diet group (5% krill oil plus 2% soy oil) was included. The fatty acid composition of each diet is shown in FIG. 15. Analysis of the fatty acid composition was outsourced to JAPAN FOOD RESEARCH LABORATORIES. The ω3/ω6 ratio in diet was 0.12 in the control group, 0.94 in the krill oil group, and 0.57 in the fish oil group. The fatty acid composition in serum, cerebral cortex, and hippocampus was measured as in Test Example 8.

TABLE 15

Fatty Acid Composition of Each Diet (%)

| Fatty acid | Standard diet (7% soy oil) | 5% Krill oil diet (2% soy oil) | 2.5% Fish oil diet (4.5% soy oil) |
|---|---|---|---|
| 12:0 | 0 | 0.2 | 0 |
| 14:0 | 0.2 | 7.8 | 1.7 |
| 15:0 | 0 | 0.3 | 0 |
| 16:0 | 11.6 | 19.1 | 10.4 |
| 17:0 | 0 | 1.6 | 0.2 |
| 18:0 | 4.2 | 2.5 | 2.9 |
| 20:0 | 0.3 | 0.2 | 0.2 |
| 22:0 | 0.4 | 0.2 | 0.3 |
| 24:0 | 0.2 | 0 | 0 |
| Total of saturated fatty acids | 16.9 | 31.9 | 15.7 |
| 14:1 | 0 | 0.2 | 0 |
| 16:1 | 0 | 4 | 2.9 |
| 17:1 | 0 | 0.2 | 0 |
| 18:1 | 24.3 | 20.1 | 18.5 |

TABLE 15-continued

Fatty Acid Composition of Each Diet (%)

| Fatty acid | Standard diet (7% soy oil) | 5% Krill oil diet (2% soy oil) | 2.5% Fish oil diet (4.5% soy oil) |
|---|---|---|---|
| 20:1 | 0.2 | 0.6 | 0.2 |
| 22:1 | 0 | 0.4 | 0 |
| Total of monounsaturated fatty acids | 24.5 | 25.5 | 21.6 |
| 16:2 | 0 | 0.4 | 0.6 |
| 16:3 | 0 | 0 | 1.0 |
| 16:4 | 0 | 0.5 | 1.7 |
| 18:2n-6 | 51.6 | 19.9 | 36.7 |
| 18:3n-3 | 6.3 | 2.9 | 4.7 |
| 18:4n-3 | 0 | 2 | 1.6 |
| 20:4n-6 | 0 | 0.2 | 0.3 |
| 20:4n-3 | 0 | 0.2 | 0.3 |
| 20:5n-3 | 0 | 8.9 | 9.2 |
| 21:5n-3 | 0 | 0.3 | 0.4 |
| 22:5n-3 | 0 | 0.3 | 0.8 |
| 22:6n-3 | 0 | 4.2 | 4.2 |
| Total of polyunsaturated fatty acids | 57.9 | 39.8 | 61.5 |
| unknown | 0.7 | 2.8 | 1.2 |
| ω3/ω6 ratio | 0.12 | 0.94 | 0.57 |

Figure 11:
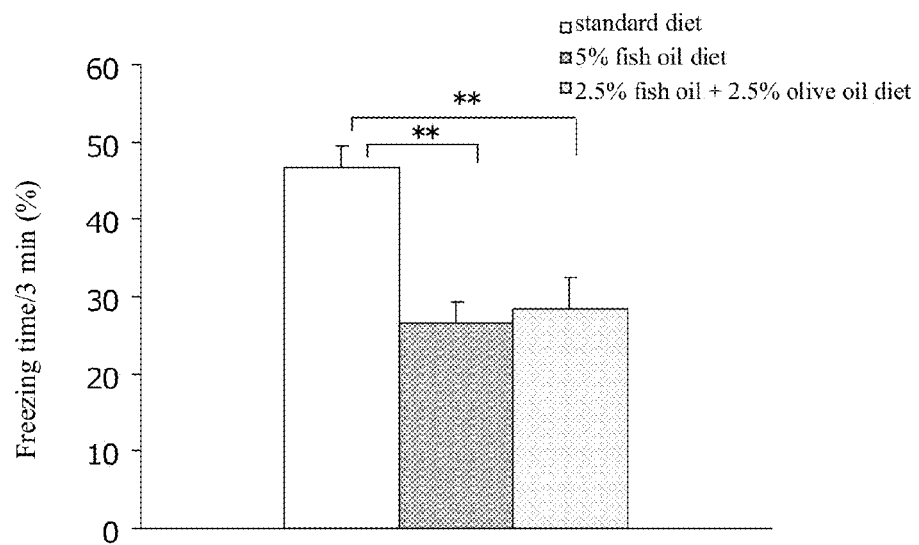
FIG. 11 is a graph showing the effects of 6-week feeding of 5% fish oil solid diet or 2.5% fish oil+olive oil diet on the freezing response of mice in a fear conditioning experiment; each group consisted of 10 animals; the vertical axis represents the freezing time in a 3-min period; all values refer to mean±standard error; and ** indicates the presence of a significant difference between the control group and each of the fish oil group and the fish oil+olive oil group at $P<0.01$.

Subsequently, a diet comprising 2.5% fish oil, 2.5% olive oil, and 2% soy oil was prepared by adding olive oil to the fish oil diet to alter the ω3/ω6 ratio, and a diet comprising 5% fish oil and 2% soy oil was prepared by adding twice the amount of fish oil (5%) to the fish oil diet. Using these diets, a fear conditioning test was conducted. The method of the fear conditioning test was the same as in Test Example 1. The results of the fear conditioning test are shown in FIG. 11. The ω3/ω6 ratio in diet was 0.12 in the control group, 2.02 in the 5% fish oil group, and 0.98 in the 2.5% fish oil+2.5% olive oil group. The fatty acid composition in each diet is shown in Table 16.

TABLE 16

Fatty Acid Composition of Each Diet (%)

| Fatty acid | Standard diet (7% soy oil) | 5% Fish oil diet (2% soy oil) | 2.5% Fish oil + 2.5% Olive oil diet (2% soy oil) |
|---|---|---|---|
| 12:0 | 0 | 0 | 0 |
| 14:0 | 0.1 | 3.4 | 1.7 |
| 15:0 | 0 | 0.2 | 0 |
| 16:0 | 11.8 | 8.8 | 10.7 |
| 17:0 | 0 | 0.2 | 0.2 |
| 18:0 | 3.8 | 1.7 | 2.9 |
| 20:0 | 0.4 | 0 | 0.3 |
| 22:0 | 0.4 | 0.5 | 0.4 |
| 24:0 | 0.2 | 0 | 0 |
| Total of saturated fatty acids | 16.7 | 14.8 | 16.2 |
| 16:1 | 0 | 5.7 | 3.1 |
| 17:1 | 0 | 0.2 | 0 |
| 18:1 | 26.6 | 13.2 | 37.6 |
| 20:1 | 0.2 | 0.3 | 0.3 |
| Total of monounsaturated fatty acids | 26.8 | 19.4 | 41.0 |
| 16:2 | 0 | 1.1 | 0.5 |
| 16:3 | 0 | 1.8 | 0.9 |
| 16:4 | 0 | 3.3 | 1.6 |
| 18:2n-6 | 49.9 | 18 | 19.5 |
| 18:3n-3 | 5.8 | 2.6 | 2.4 |
| 18:4n-3 | 0 | 3.2 | 1.6 |
| 20:2n-6 | 0 | 0.1 | 0 |
| 20:4n-6 | 0 | 0.8 | 0.4 |
| 20:4n-3 | 0 | 0.7 | 0.3 |
| 20:5n-3 | 0 | 19.8 | 9.3 |
| 21:5n-3 | 0 | 0.7 | 0.4 |
| 22:5n-6 | 0 | 0.2 | 0 |
| 22:5n-3 | 0 | 1.8 | 0.9 |
| 22:6n-3 | 0 | 9.8 | 4.6 |
| Total of polyunsaturated fatty | 55.7 | 63.9 | 42.4 |
| unknown | 0.8 | 1.9 | 0.4 |
| ω3/ω6 ratio | 0.12 | 2.02 | 0.98 |

Results

As in Test Example 4, no significant difference in the freezing time was observed in the 2.5% fish oil group as compared with the control group; on the other hand, the freezing time was significantly decreased in the krill oil group (FIG. 10). In contrast, both the 5% fish oil group and the 2.5% fish+2.5% olive oil group saw a significant decrease in freezing time as compared with the control group (FIG. 11). When fatty acid composition was measured in each of serum, cerebral cortex, and hippocampus and calculated for ω3/ω6 ratio, the 2.5% fish oil+2.5% olive oil group had higher ω3/ω6 ratios than the 2.5% fish oil group (Tables 17-22.) These results suggest that the fear response can be alleviated by modifying the ω3/ω6 ratio in diet such that the proportion of ω3 becomes higher than that of ω6. The fatty acid composition in the serum, cerebral cortex, and hippocampus is shown in Tables 17-22.

TABLE 17

Relative Values (Area %) for Fatty Acid Composition and Quantified Values (μg/ml) for Fatty Acid in Serum

| Serum | Control group | | | | 5% Krill oil | | | | 2.5% Fish Oil | | | |
|---|---|---|---|---|---|---|---|---|---|---|---|---|
| FA | av (%) | s.e.(%) | av (μg/ml) | s.e.(μg/ml) | av (%) | s.e.(%) | av (μg/ml) | s.e.(μg/ml) | av (%) | s.e.(%) | av (μg/ml) | s.e.(μg/ml) |
| 12:0 | 0.00 | 0.00 | 0.00 | 0.00 | 0.10 | 0.02 | 2.49 | 0.51 | 0.00 | 0.00 | 0.00 | 0.00 |
| 14:0 | 0.37 | 0.02 | 9.54 | 0.55 | 1.13 | 0.05 | 28.11 | 2.11 | 0.44 | 0.02 | 10.83 | 0.71 |
| 14:1 | 0.00 | 0.00 | 0.00 | 0.00 | 0.12 | 0.02 | 2.93 | 0.61 | 0.00 | 0.00 | 0.00 | 0.00 |
| 16:0 | 22.57 | 0.20 | 587.33 | 15.09 | 24.15 | 0.06 | 595.93 | 23.63 | 24.23 | 0.15 | 596.45 | 18.80 |
| 16:1n-7 | 2.58 | 0.15 | 67.41 | 4.93 | 6.31 | 0.27 | 155.32 | 7.92 | 2.55 | 0.13 | 62.78 | 4.17 |
| 18:0 | 7.17 | 0.26 | 186.50 | 7.56 | 5.31 | 0.13 | 131.37 | 7.58 | 6.36 | 0.07 | 157.00 | 7.02 |
| 18:1n-9 | 10.90 | 0.31 | 283.86 | 12.36 | 13.53 | 0.28 | 334.23 | 16.83 | 11.21 | 0.27 | 276.29 | 11.81 |

TABLE 17-continued

Relative Values (Area %) for Fatty Acid Composition and Quantified Values (μg/ml) for Fatty Acid in Serum

| Serum FA | Control group av (%) | s.e.(%) | av (μg/ml) | s.e.(μg/ml) | 5% Krill oil av (%) | s.e.(%) | av (μg/ml) | s.e.(μg/ml) | 2.5% Fish Oil av (%) | s.e.(%) | av (μg/ml) | s.e.(μg/ml) |
|---|---|---|---|---|---|---|---|---|---|---|---|---|
| 18:1n-7 | 1.42 | 0.05 | 36.85 | 1.58 | 1.67 | 0.02 | 41.23 | 1.83 | 0.97 | 0.01 | 23.88 | 1.02 |
| 18:2n-6 | 25.83 | 0.15 | 671.81 | 15.31 | 21.40 | 0.60 | 529.58 | 31.60 | 26.19 | 0.34 | 646.70 | 30.89 |
| 18:3n-6 | 0.69 | 0.03 | 18.09 | 0.86 | 0.22 | 0.05 | 5.59 | 1.33 | 0.37 | 0.01 | 9.19 | 0.39 |
| 18:3n-3 | 0.71 | 0.03 | 18.61 | 1.15 | 0.73 | 0.02 | 18.19 | 1.16 | 0.64 | 0.03 | 15.78 | 1.13 |
| 20:0 | 0.02 | 0.02 | 0.54 | 0.54 | 0.04 | 0.02 | 0.90 | 0.58 | 0.00 | 0.00 | 0.00 | 0.00 |
| 20:1n-9 | 0.19 | 0.06 | 4.93 | 1.59 | 0.21 | 0.05 | 5.39 | 1.23 | 0.12 | 0.06 | 3.10 | 1.48 |
| 20:2n-6 | 0.01 | 0.01 | 0.39 | 0.39 | 0.02 | 0.02 | 0.46 | 0.46 | 0.20 | 0.13 | 4.74 | 3.01 |
| 20:3n-6 | 0.77 | 0.04 | 19.96 | 1.28 | 0.43 | 0.03 | 10.55 | 0.65 | 0.32 | 0.11 | 8.12 | 2.73 |
| 20:4n-6 | 17.81 | 0.53 | 462.00 | 5.45 | 2.93*** | 0.12 | 72.02** | 3.62 | 5.65 | 0.23 | 138.80 | 5.57 |
| 20:5n-3 | 0.48 | 0.02 | 12.40 | 0.47 | 8.66 | 0.70 | 211.04*** | 11.53 | 6.43 | 0.24 | 158.88 | 9.74 |
| 22:0 | 0.18 | 0.06 | 4.80 | 1.53 | 0.18 | 0.06 | 4.58 | 1.48 | 0.00 | 0.00 | 0.00 | 0.00 |
| 22:4n-6 | 0.02 | 0.02 | 0.41 | 0.41 | 0.00 | 0.00 | 0.00 | 0.00 | 0.00 | 0.00 | 0.00 | 0.00 |
| 22:5n-3 | 0.37 | 0.01 | 9.63 | 0.36 | 0.91 | 0.03 | 22.40 | 0.78 | 1.08 | 0.03 | 26.47 | 0.61 |
| 22:6n-3 | 7.00 | 0.09 | 181.91 | 2.67 | 9.27 | 0.16 | 228.80 | 9.87 | 11.15** | 0.27 | 274.23*** | 9.75 |
| 24:1 | 0.06 | 0.06 | 1.64 | 1.64 | 0.24 | 0.05 | 6.03 | 1.24 | 0.23 | 0.05 | 5.57 | 1.16 |

***With significant difference from the standard diet at $P<0.001$ (Kruskal-Wallis-Dunn test); the test was performed on arachidonic acid, eicosapentaenoic acid, and docosahexaenoic acid.

TABLE 18

Relative Values (Area %) for Fatty Acid Composition and Quantified Values (μg/ml) for Fatty Acid in Cerebral Cortex

| Cerebral cortex FA | Control group av (%) | s.e. (%) | av (μg/mg) | s.e. (μg/mg) | 5% Krill oil av (%) | s.e. (%) | av (μg/mg) | s.e. (μg/mg) | 2.5% Fish oil av (%) | s.e. (%) | av (μg/mg) | s.e. (μg/mg) |
|---|---|---|---|---|---|---|---|---|---|---|---|---|
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.06 | 0.03 | 0.02 | 0.01 | 0.16 | 0.00 | 0.06 | 0.00 | 0.14 | 0.00 | 0.05 | 0.00 |
| 16:0 | 20.28 | 0.13 | 7.74 | 0.04 | 20.41 | 0.07 | 7.69 | 0.06 | 20.40 | 0.05 | 7.75 | 0.03 |
| 16:1n-7 | 0.53 | 0.01 | 0.20 | 0.00 | 0.68 | 0.01 | 0.26 | 0.01 | 0.60 | 0.01 | 0.23 | 0.00 |
| 18:0 | 20.32 | 0.07 | 7.75 | 0.05 | 20.08 | 0.05 | 7.57 | 0.08 | 20.20 | 0.12 | 7.68 | 0.04 |
| 18:1n-9 | 13.11 | 0.09 | 5.00 | 0.05 | 13.85 | 0.07 | 5.22 | 0.06 | 13.67 | 0.04 | 5.19 | 0.01 |
| 18:1n-7 | 3.42 | 0.02 | 1.30 | 0.01 | 3.49 | 0.02 | 1.32 | 0.01 | 3.29 | 0.01 | 1.25 | 0.01 |
| 18:2n-6 | 0.75 | 0.01 | 0.29 | 0.00 | 0.49 | 0.02 | 0.19 | 0.01 | 0.69 | 0.02 | 0.26 | 0.01 |
| 18:3n-6 | 0.00 | 0.00 | 0.00 | 0.00 | 0.00 | 0.00 | 0.00 | 0.00 | 0.00 | 0.00 | 0.00 | 0.00 |
| 18:3n-3 | 0.00 | 0.00 | 0.00 | 0.00 | 0.00 | 0.00 | 0.00 | 0.00 | 0.00 | 0.00 | 0.00 | 0.00 |
| 20:0 | 0.28 | 0.00 | 0.11 | 0.00 | 0.27 | 0.01 | 0.10 | 0.00 | 0.27 | 0.00 | 0.10 | 0.00 |
| 20:1n-9 | 0.96 | 0.03 | 0.37 | 0.01 | 0.95 | 0.02 | 0.36 | 0.01 | 0.93 | 0.01 | 0.35 | 0.00 |
| 20:2n-6 | 0.06 | 0.03 | 0.02 | 0.01 | 0.05 | 0.03 | 0.02 | 0.01 | 0.00 | 0.00 | 0.00 | 0.00 |
| 20:3n-6 | 0.44 | 0.01 | 0.17 | 0.00 | 0.54 | 0.01 | 0.20 | 0.00 | 0.53 | 0.01 | 0.20 | 0.00 |
| 20:4n-6 | 9.61 | 0.10 | 3.66 | 0.03 | 7.4*** | 0.08 | 2.79*** | 0.04 | 7.96 | 0.04 | 3.03 | 0.01 |
| 20:3n-3 | 0.00 | 0.00 | 0.00 | 0.00 | 0.00 | 0.00 | 0.00 | 0.00 | 0.00 | 0.00 | 0.00 | 0.00 |
| 20:5n-3 | 0.00 | 0.00 | 0.00 | 0.00 | 0.54 | 0.09 | 0.20 | 0.03 | 0.27 | 0.02 | 0.10 | 0.01 |
| 22:0 | 0.32 | 0.01 | 0.12 | 0.01 | 0.30 | 0.01 | 0.11 | 0.01 | 0.31 | 0.01 | 0.12 | 0.01 |
| 22:1n-9 | 0.05 | 0.03 | 0.02 | 0.01 | 0.03 | 0.02 | 0.01 | 0.01 | 0.02 | 0.02 | 0.01 | 0.01 |
| 22:2n-6 | 0.02 | 0.02 | 0.01 | 0.01 | 0.00 | 0.00 | 0.00 | 0.00 | 0.00 | 0.00 | 0.00 | 0.00 |
| 22:4n-6 | 2.10 | 0.03 | 0.80 | 0.01 | 1.34 | 0.02 | 0.51 | 0.01 | 1.44 | 0.02 | 0.55 | 0.00 |
| 22:5n-3 | 0.08 | 0.04 | 0.03 | 0.01 | 0.57 | 0.01 | 0.21 | 0.00 | 0.46 | 0.00 | 0.17 | 0.00 |
| 24:0 | 0.48 | 0.01 | 0.18 | 0.01 | 0.47 | 0.02 | 0.18 | 0.01 | 0.48 | 0.00 | 0.18 | 0.00 |
| 22:6n-3 | 17.15 | 0.16 | 6.54 | 0.06 | 18.94** | 0.11 | 7.13* | 0.08 | 18.85* | 0.14 | 7.16* | 0.07 |
| 24:1 | 1.00 | 0.02 | 0.38 | 0.01 | 0.88 | 0.03 | 0.33 | 0.01 | 0.91 | 0.01 | 0.35 | 0.00 |

With significant difference from the standard diet at *$P<0.05$, $P<0.01$, and *$P<0.001$ (Kruskal-Wallis-Dunn test); the test was performed on arachidonic acid and docosahexaenoic acid.

TABLE 19

Relative Values (Area %) for Fatty Acid Composition and Quantified Values (μg/ml) for Fatty Acid in Hippocampus

| Hippo-campus FA | Control group av (%) | s.e. (%) | av (μg/mg) | s.e. (μg/mg) | 5% Krill oil av (%) | s.e. (%) | av (μg/mg) | s.e. (μg/mg) | 2.5% Fish Oil av (%) | s.e. (%) | av (μg/mg) | s.e. (μg/mg) |
|---|---|---|---|---|---|---|---|---|---|---|---|---|
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.00 | 0.00 | 0.00 | 0.00 | 0.00 | 0.00 | 0.00 | 0.00 | 0.00 | 0.00 | 0.00 | 0.00 |
| 16:0 | 20.37 | 0.19 | 6.88 | 0.15 | 20.06 | 0.18 | 6.83 | 0.09 | 20.65 | 0.12 | 6.78 | 0.11 |
| 16:1n-7 | 0.47 | 0.01 | 0.16 | 0.01 | 0.63 | 0.02 | 0.21 | 0.01 | 0.53 | 0.02 | 0.18 | 0.01 |

TABLE 19-continued

Relative Values (Area %) for Fatty Acid Composition and
Quantified Values (μg/ml) for Fatty Acid in Hippocampus

| Hippo-campus FA | Control group av (%) | Control group s.e. (%) | Control group av (μg/mg) | Control group s.e. (μg/mg) | 5% Krill oil av (%) | 5% Krill oil s.e. (%) | 5% Krill oil av (μg/mg) | 5% Krill oil s.e. (μg/mg) | 2.5% Fish Oil av (%) | 2.5% Fish Oil s.e. (%) | 2.5% Fish Oil av (μg/mg) | 2.5% Fish Oil s.e. (μg/mg) |
|---|---|---|---|---|---|---|---|---|---|---|---|---|
| 18:0 | 21.07 | 0.13 | 7.12 | 0.17 | 20.64 | 0.06 | 7.03 | 0.10 | 21.00 | 0.06 | 6.89 | 0.14 |
| 18:1n-9 | 13.22 | 0.16 | 4.47 | 0.16 | 14.46 | 0.20 | 4.93 | 0.13 | 13.73 | 0.11 | 4.51 | 0.12 |
| 18:1n-7 | 3.43 | 0.04 | 1.16 | 0.04 | 3.49 | 0.04 | 1.19 | 0.03 | 3.24 | 0.01 | 1.06 | 0.02 |
| 18:2n-6 | 0.69 | 0.01 | 0.23 | 0.01 | 0.49 | 0.02 | 0.17 | 0.01 | 0.68 | 0.02 | 0.22 | 0.01 |
| 18:3n-6 | 0.00 | 0.00 | 0.00 | 0.00 | 0.00 | 0.00 | 0.00 | 0.00 | 0.00 | 0.00 | 0.00 | 0.00 |
| 18:3n-3 | 0.00 | 0.00 | 0.00 | 0.00 | 0.00 | 0.00 | 0.00 | 0.00 | 0.00 | 0.00 | 0.00 | 0.00 |
| 20:0 | 0.18 | 0.06 | 0.06 | 0.02 | 0.27 | 0.01 | 0.09 | 0.00 | 0.04 | 0.04 | 0.01 | 0.01 |
| 20:1n-9 | 0.82 | 0.04 | 0.28 | 0.02 | 0.88 | 0.06 | 0.30 | 0.02 | 0.71 | 0.03 | 0.24 | 0.01 |
| 20:2n-6 | 0.00 | 0.00 | 0.00 | 0.00 | 0.07 | 0.04 | 0.02 | 0.02 | 0.00 | 0.00 | 0.00 | 0.00 |
| 20:3n-6 | 0.46 | 0.01 | 0.16 | 0.01 | 0.56 | 0.01 | 0.19 | 0.00 | 0.58 | 0.01 | 0.19 | 0.01 |
| 20:4n-6 | 11.59 | 0.17 | 3.91 | 0.08 | 8.66*** | 0.10 | 2.95*** | 0.04 | 9.65 | 0.12 | 3.17 | 0.06 |
| 20:3n-3 | 0.04 | 0.04 | 0.01 | 0.01 | 0.00 | 0.00 | 0.00 | 0.00 | 0.00 | 0.00 | 0.00 | 0.00 |
| 20:5n-3 | 0.00 | 0.00 | 0.00 | 0.00 | 0.49 | 0.07 | 0.17 | 0.03 | 0.14 | 0.06 | 0.05 | 0.02 |
| 22:0 | 0.05 | 0.05 | 0.01 | 0.01 | 0.12 | 0.06 | 0.04 | 0.02 | 0.09 | 0.06 | 0.03 | 0.02 |
| 22:1n-9 | 0.00 | 0.00 | 0.00 | 0.00 | 0.00 | 0.00 | 0.00 | 0.00 | 0.00 | 0.00 | 0.00 | 0.00 |
| 22:2n-6 | 0.00 | 0.00 | 0.00 | 0.00 | 0.00 | 0.00 | 0.00 | 0.00 | 0.00 | 0.00 | 0.00 | 0.00 |
| 22:4n-6 | 2.45 | 0.02 | 0.83 | 0.02 | 1.58 | 0.02 | 0.54 | 0.01 | 1.66 | 0.02 | 0.55 | 0.01 |
| 22:5n-3 | 0.00 | 0.00 | 0.00 | 0.00 | 0.60 | 0.00 | 0.20 | 0.00 | 0.49 | 0.01 | 0.16 | 0.00 |
| 24:0 | 0.06 | 0.06 | 0.02 | 0.02 | 0.20 | 0.09 | 0.07 | 0.03 | 0.00 | 0.00 | 0.00 | 0.00 |
| 22:6n-3 | 16.24 | 0.13 | 5.48 | 0.12 | 17.53 | 0.25 | 5.97 | 0.09 | 18.21** | 0.15 | 5.98 | 0.09 |
| 24:1 | 0.80 | 0.17 | 0.27 | 0.06 | 0.92 | 0.06 | 0.31 | 0.03 | 0.74 | 0.06 | 0.24 | 0.02 |

With significant difference from the standard diet at P < 0.01 and *P < 0.001 (Kruskal-Wallis-Dunn test); the test was performed on arachidonic acid and docosahexaenoic acid.

TABLE 20

Relative Values (Area %) for Fatty Acid Composition and Quantified Values (μg/ml) for Fatty Acid in Serum

| Serum FA | Control group av (%) | Control group s.e.(%) | Control group av (μg/ml) | Control group s.e.(μg/ml) | 2.5% Fish oil + olive oil av (%) | 2.5% Fish oil + olive oil s.e.(%) | 2.5% Fish oil + olive oil av (μg/ml) | 2.5% Fish oil + olive oil s.e.(μg/ml) | 5% Fish Oil av (%) | 5% Fish Oil s.e.(%) | 5% Fish Oil av (μg/ml) | 5% Fish Oil s.e.(μg/ml) |
|---|---|---|---|---|---|---|---|---|---|---|---|---|
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.30 | 0.06 | 8.61 | 1.84 | 0.46 | 0.01 | 10.76 | 0.33 | 0.69 | 0.01 | 13.89 | 0.63 |
| 14:1 | 0.00 | 0.00 | 0.00 | 0.00 | 0.00 | 0.00 | 0.00 | 0.00 | 0.00 | 0.00 | 0.00 | 0.00 |
| 16:0 | 21.68 | 0.75 | 598.78 | 23.61 | 24.05 | 0.40 | 564.19 | 22.48 | 24.91 | 0.20 | 503.45 | 26.45 |
| 16:1n-7 | 2.21 | 0.09 | 61.54 | 3.99 | 2.72 | 0.17 | 63.19 | 2.78 | 3.82 | 0.09 | 77.15 | 4.21 |
| 18:0 | 7.06 | 0.48 | 195.85 | 15.96 | 6.22 | 0.29 | 144.96 | 3.49 | 6.27 | 0.27 | 125.41 | 3.36 |
| 18:1n-9 | 12.12 | 0.58 | 336.94 | 23.83 | 17.00 | 0.67 | 399.89 | 25.25 | 10.57 | 0.16 | 213.40 | 11.25 |
| 18:1n-7 | 1.58 | 0.15 | 43.95 | 4.95 | 1.06 | 0.04 | 24.65 | 0.62 | 0.92 | 0.01 | 18.56 | 0.94 |
| 18:2n-6 | 25.67 | 0.70 | 709.67 | 27.33 | 19.13 | 1.13 | 450.58 | 34.42 | 17.51 | 1.44 | 360.07 | 40.97 |
| 18:3n-6 | 0.46 | 0.03 | 12.68 | 1.03 | 0.00 | 0.00 | 0.00 | 0.00 | 0.00 | 0.00 | 0.00 | 0.00 |
| 18:3n-3 | 0.66 | 0.04 | 18.28 | 1.44 | 0.34 | 0.07 | 7.96 | 1.69 | 0.46 | 0.09 | 9.62 | 1.98 |
| 20:0 | 0.00 | 0.00 | 0.00 | 0.00 | 0.00 | 0.00 | 0.00 | 0.00 | 0.00 | 0.00 | 0.00 | 0.00 |
| 20:1n-9 | 0.00 | 0.00 | 0.00 | 0.00 | 0.00 | 0.00 | 0.00 | 0.00 | 0.00 | 0.00 | 0.00 | 0.00 |
| 20:2n-6 | 0.00 | 0.00 | 0.00 | 0.00 | 0.00 | 0.00 | 0.00 | 0.00 | 0.00 | 0.00 | 0.00 | 0.00 |
| 20:3n-6 | 1.52 | 0.27 | 41.19 | 6.65 | 0.63 | 0.07 | 14.65 | 1.29 | 0.47 | 0.10 | 9.43 | 1.93 |
| 20:4n-6 | 16.68 | 0.41 | 460.92 | 15.29 | 4.86 | 0.18 | 113.54** | 3.66 | 5.68 | 0.20 | 115.26* | 7.84 |
| 20:5n-3 | 0.43 | 0.02 | 11.86 | 0.56 | 8.58 | 1.11 | 197.76 | 20.42 | 11.98** | 0.72 | 238.51** | 4.43 |
| 22:0 | 0.28 | 0.06 | 7.54 | 1.54 | 0.18 | 0.09 | 4.10 | 1.95 | 0.11 | 0.11 | 1.66 | 1.66 |
| 22:4n-6 | 0.00 | 0.00 | 0.00 | 0.00 | 0.00 | 0.00 | 0.00 | 0.00 | 0.00 | 0.00 | 0.00 | 0.00 |
| 22:5n-3 | 0.34 | 0.01 | 9.45 | 0.13 | 1.25 | 0.08 | 29.20 | 1.27 | 1.43 | 0.16 | 28.03 | 1.50 |
| 22:6n-3 | 6.76 | 0.20 | 186.44 | 4.34 | 11.92 | 0.22 | 279.22* | 9.67 | 14.25*** | 0.65 | 284.67** | 5.11 |
| 24:1 | 0.52 | 0.02 | 14.44 | 0.39 | 0.44 | 0.04 | 10.29 | 0.57 | 0.12 | 0.07 | 2.45 | 1.55 |

With significant difference from the standard diet at *P < 0.05, P < 0.01, and *P < 0.001 (Kruskal-Wallis-Dunn test); the test was performed on arachidonic acid, eicosapentaenoic acid, and docosahexaenoic acid.

TABLE 21

Relative Values (Area %) for Fatty Acid Composition and Quantified
Values (μg/ml) for Fatty Acid in Cerebral Cortex

| Cerebral cortex FA | Control group av (%) | Control group s.e. (%) | Control group av (μg/mg) | Control group s.e. (μg/mg) | 2.5% Fish oil + olive oil av (%) | 2.5% Fish oil + olive oil s.e. (%) | 2.5% Fish oil + olive oil av (μg/mg) | 2.5% Fish oil + olive oil s.e. (μg/mg) | 5% Fish oil av (%) | 5% Fish oil s.e. (%) | 5% Fish oil av (μg/mg) | 5% Fish oil s.e. (μg/mg) |
|---|---|---|---|---|---|---|---|---|---|---|---|---|
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.10 | 0.02 | 0.03 | 0.01 | 0.07 | 0.03 | 0.02 | 0.01 | 0.12 | 0.02 | 0.04 | 0.01 |

TABLE 21-continued

Relative Values (Area %) for Fatty Acid Composition and Quantified Values (μg/ml) for Fatty Acid in Cerebral Cortex

| Cerebral cortex FA | Control group | | | | 2.5% Fish oil + olive oil | | | | 5% Fish oil | | | |
|---|---|---|---|---|---|---|---|---|---|---|---|---|
| | av (%) | s.e. (%) | av (μg/mg) | s.e. (μg/mg) | av (%) | s.e. (%) | av (μg/mg) | s.e. (μg/mg) | av (%) | s.e. (%) | av (μg/mg) | s.e. (μg/mg) |
| 14:1 | 0.31 | 0.31 | 0.10 | 0.10 | 0.00 | 0.00 | 0.00 | 0.00 | 0.00 | 0.00 | 0.00 | 0.00 |
| 16:0 | 19.82 | 0.28 | 5.71 | 0.09 | 19.99 | 0.14 | 5.93 | 0.08 | 19.81 | 0.29 | 5.98 | 0.06 |
| 16:1n-7 | 0.49 | 0.01 | 0.14 | 0.00 | 0.55 | 0.01 | 0.16 | 0.00 | 0.53 | 0.11 | 0.16 | 0.03 |
| 18:0 | 20.56 | 0.17 | 5.92 | 0.09 | 20.61 | 0.13 | 6.11 | 0.07 | 20.33 | 0.24 | 6.14 | 0.06 |
| 18:1n-9 | 12.44 | 0.22 | 3.59 | 0.13 | 13.86 | 0.14 | 4.11 | 0.08 | 13.67 | 0.05 | 4.13 | 0.10 |
| 18:1n-7 | 2.94 | 0.06 | 0.85 | 0.03 | 2.88 | 0.03 | 0.85 | 0.02 | 2.86 | 0.02 | 0.86 | 0.02 |
| 18:2n-6 | 0.69 | 0.02 | 0.20 | 0.00 | 0.46 | 0.02 | 0.14 | 0.00 | 0.37 | 0.02 | 0.11 | 0.01 |
| 18:3n-6 | 0.00 | 0.00 | 0.00 | 0.00 | 0.00 | 0.00 | 0.00 | 0.00 | 0.02 | 0.01 | 0.01 | 0.00 |
| 18:3n-3 | 0.00 | 0.00 | 0.00 | 0.00 | 0.00 | 0.00 | 0.00 | 0.00 | 0.00 | 0.00 | 0.00 | 0.00 |
| 20:0 | 0.33 | 0.05 | 0.09 | 0.01 | 0.29 | 0.01 | 0.09 | 0.00 | 0.30 | 0.01 | 0.09 | 0.00 |
| 20:1n-9 | 0.78 | 0.08 | 0.23 | 0.03 | 0.86 | 0.05 | 0.26 | 0.02 | 0.82 | 0.04 | 0.25 | 0.02 |
| 20:2n-6 | 0.13 | 0.05 | 0.04 | 0.01 | 0.07 | 0.03 | 0.02 | 0.01 | 0.10 | 0.05 | 0.03 | 0.02 |
| 20:3n-6 | 0.42 | 0.00 | 0.12 | 0.00 | 0.49 | 0.00 | 0.15 | 0.00 | 0.36 | 0.01 | 0.11 | 0.00 |
| 20:4n-6 | 10.90 | 0.14 | 3.14 | 0.04 | 7.87* | 0.16 | 2.33* | 0.04 | 7.55** | 0.12 | 2.28** | 0.04 |
| 20:3n-3 | 0.00 | 0.00 | 0.00 | 0.00 | 0.00 | 0.00 | 0.00 | 0.00 | 0.00 | 0.00 | 0.00 | 0.00 |
| 20:5n-3 | 0.00 | 0.00 | 0.00 | 0.00 | 0.33 | 0.01 | 0.10 | 0.00 | 0.50 | 0.02 | 0.15 | 0.00 |
| 22:0 | 0.38 | 0.04 | 0.11 | 0.01 | 0.44 | 0.03 | 0.13 | 0.01 | 0.45 | 0.02 | 0.14 | 0.01 |
| 22:1n-9 | 0.04 | 0.02 | 0.01 | 0.01 | 0.04 | 0.02 | 0.01 | 0.01 | 0.07 | 0.02 | 0.02 | 0.01 |
| 22:2n-6 | 0.00 | 0.00 | 0.00 | 0.00 | 0.00 | 0.00 | 0.00 | 0.00 | 0.03 | 0.02 | 0.01 | 0.01 |
| 22:4n-6 | 2.37 | 0.05 | 0.68 | 0.01 | 1.46 | 0.04 | 0.43 | 0.01 | 1.26 | 0.03 | 0.38 | 0.01 |
| 22:5n-3 | 0.16 | 0.00 | 0.04 | 0.00 | 0.50 | 0.01 | 0.15 | 0.00 | 0.63 | 0.01 | 0.19 | 0.00 |
| 24:0 | 0.51 | 0.07 | 0.15 | 0.02 | 0.60 | 0.05 | 0.18 | 0.02 | 0.62 | 0.05 | 0.19 | 0.02 |
| 22:6n-3 | 16.44 | 0.19 | 4.74 | 0.11 | 18.75* | 0.24 | 5.56* | 0.11 | 18.96** | 0.26 | 5.73** | 0.06 |
| 24:1 | 0.91 | 0.12 | 0.26 | 0.04 | 1.09 | 0.09 | 0.32 | 0.03 | 1.08 | 0.08 | 0.33 | 0.03 |

With significant difference from the standard diet at *P < 0.05 and **P < 0.01 (Kruskal-Wallis-Dunn test); the test was performed on arachidonic acid and docosahexaenoic acid.

TABLE 22

Relative Values (Area %) for Fatty Acid Composition and Quantified Values (μg/ml) for Fatty Acid in Hippocampus

| Hippo-campus FA | Control group | | | | 2.5% Fish oil + olive oil | | | | 5% Fish oil | | | |
|---|---|---|---|---|---|---|---|---|---|---|---|---|
| | av (%) | s.e. (%) | av (μg/mg) | s.e. (μg/mg) | av (%) | s.e. (%) | av (μg/mg) | s.e. (μg/mg) | av (%) | s.e. (%) | av (μg/mg) | s.e. (μg/mg) |
| 12:0 | 0.00 | 0.00 | 0.00 | 0.00 | 0.00 | 0.00 | 0.00 | 0.00 | 0.00 | 0.00 | 0.00 | 0.00 |
| 14:0 | 0.00 | 0.00 | 0.00 | 0.00 | 0.00 | 0.00 | 0.00 | 0.00 | 0.00 | 0.00 | 0.00 | 0.00 |
| 16:0 | 19.48 | 0.14 | 6.66 | 0.15 | 19.45 | 0.14 | 6.75 | 0.12 | 19.61 | 0.10 | 7.01 | 0.08 |
| 16:1n-7 | 0.48 | 0.00 | 0.16 | 0.00 | 0.55 | 0.01 | 0.19 | 0.01 | 0.63 | 0.01 | 0.22 | 0.01 |
| 18:0 | 20.73 | 0.07 | 7.09 | 0.14 | 20.41 | 0.12 | 7.09 | 0.10 | 20.58 | 0.05 | 7.34 | 0.08 |
| 18:1n-9 | 13.75 | 0.14 | 4.71 | 0.12 | 15.70 | 0.42 | 5.46 | 0.22 | 14.96 | 0.05 | 5.31 | 0.06 |
| 18:1n-7 | 3.02 | 0.03 | 1.03 | 0.03 | 2.87 | 0.01 | 1.00 | 0.02 | 2.88 | 0.01 | 1.02 | 0.01 |
| 18:2n-6 | 0.73 | 0.03 | 0.25 | 0.01 | 0.59 | 0.05 | 0.20 | 0.02 | 0.36 | 0.07 | 0.12 | 0.03 |
| 18:3n-6 | 0.00 | 0.00 | 0.00 | 0.00 | 0.00 | 0.00 | 0.00 | 0.00 | 0.00 | 0.00 | 0.00 | 0.00 |
| 18:3n-3 | 0.00 | 0.00 | 0.00 | 0.00 | 0.00 | 0.00 | 0.00 | 0.00 | 0.00 | 0.00 | 0.00 | 0.00 |
| 20:0 | 0.16 | 0.07 | 0.06 | 0.03 | 0.20 | 0.06 | 0.07 | 0.02 | 0.10 | 0.06 | 0.02 | 0.02 |
| 20:1n-9 | 1.00 | 0.04 | 0.34 | 0.02 | 0.90 | 0.04 | 0.31 | 0.01 | 0.86 | 0.03 | 0.30 | 0.01 |
| 20:2n-6 | 0.00 | 0.00 | 0.00 | 0.00 | 0.00 | 0.00 | 0.00 | 0.00 | 0.00 | 0.00 | 0.00 | 0.00 |
| 20:3n-6 | 0.38 | 0.08 | 0.13 | 0.03 | 0.16 | 0.10 | 0.06 | 0.04 | 0.18 | 0.08 | 0.05 | 0.03 |
| 20:4n-6 | 11.51 | 0.17 | 3.93 | 0.06 | 9.10 | 0.06 | 3.16* | 0.04 | 8.66*** | 0.02 | 3.09*** | 0.04 |
| 20:3n-3 | 0.00 | 0.00 | 0.00 | 0.00 | 0.00 | 0.00 | 0.00 | 0.00 | 0.00 | 0.00 | 0.00 | 0.00 |
| 20:5n-3 | 0.00 | 0.00 | 0.00 | 0.00 | 0.42 | 0.01 | 0.15 | 0.00 | 0.62 | 0.03 | 0.21 | 0.01 |
| 22:0 | 0.46 | 0.02 | 0.16 | 0.01 | 0.43 | 0.02 | 0.15 | 0.01 | 0.44 | 0.01 | 0.16 | 0.00 |
| 22:1n-9 | 0.00 | 0.00 | 0.00 | 0.00 | 0.00 | 0.00 | 0.00 | 0.00 | 0.11 | 0.11 | 0.05 | 0.05 |
| 22:2n-6 | 0.00 | 0.00 | 0.00 | 0.00 | 0.00 | 0.00 | 0.00 | 0.00 | 0.00 | 0.00 | 0.00 | 0.00 |
| 22:4n-6 | 2.58 | 0.02 | 0.88 | 0.02 | 1.69 | 0.02 | 0.59 | 0.01 | 1.50 | 0.01 | 0.53 | 0.01 |
| 22:5n-3 | 0.00 | 0.00 | 0.00 | 0.00 | 0.56 | 0.01 | 0.20 | 0.00 | 0.68 | 0.01 | 0.24 | 0.01 |
| 24:0 | 0.56 | 0.03 | 0.19 | 0.01 | 0.52 | 0.03 | 0.18 | 0.01 | 0.53 | 0.02 | 0.19 | 0.01 |
| 22:6n-3 | 15.61 | 0.12 | 5.34 | 0.11 | 17.18 | 0.19 | 5.96 | 0.10 | 17.91*** | 0.14 | 6.42*** | 0.09 |
| 24:1 | 1.01 | 0.04 | 0.35 | 0.02 | 0.95 | 0.05 | 0.33 | 0.02 | 0.94 | 0.03 | 0.33 | 0.01 |

With significant difference from the standard diet at *P < 0.05, P < 0.01, and *P < 0.001 (Kruskal-Wallis-Dunn test); the test was performed on arachidonic acid and docosahexaenoic acid.

Test Example 11

Effect of Cannabinoid Receptor Inverse Agonist on the Fear Memory Alleviating Action of Krill Oil Since the foregoing results suggested the importance of the ω3/ω6 ratio in the intracerebral fatty acid composition for the fear memory alleviating action, the present inventors focused on the cannabinoid in the brain which is metabolized from the ω6 essential fatty acid arachidonic acid (AA). Cannabinoid has been shown to act as a retrograde signaling substance in signal transmission between synapses in the brain and a lot of reports have been published on the correlation between this substance and fear memory. In order to investigate whether the cannabinoid signal is involved in the actions of krill oil and fish oil, the present inventors conducted a fear conditioning test using the cannabinoid receptor inverse agonist rimonabant. A control group and a group fed on the 5% krill oil diet for 6 weeks were administered rimonabant or a solvent 30 minutes before fear conditioning.

Results

Figure 12:
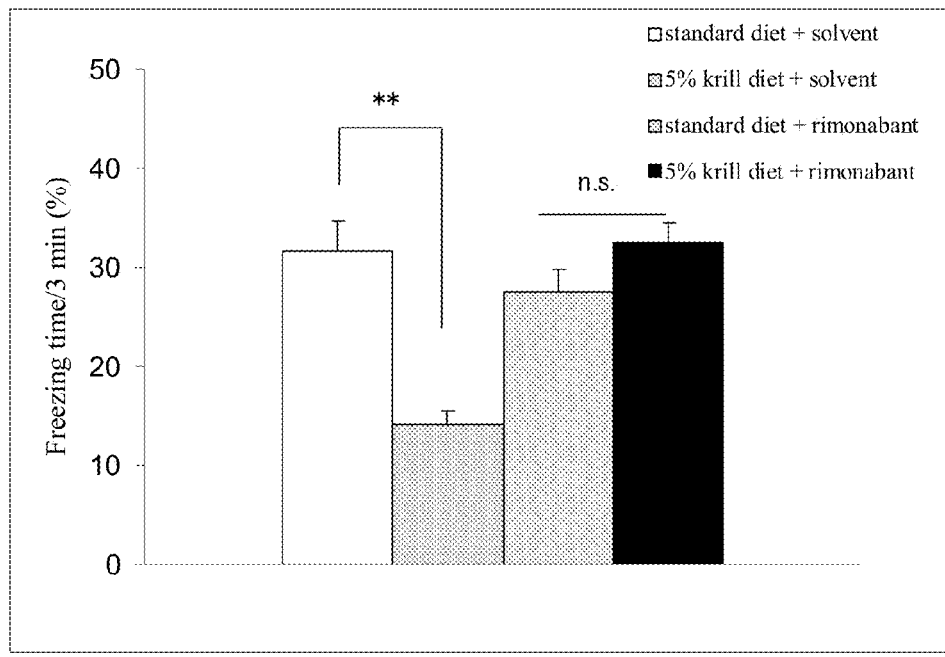
FIG. 12 is a graph showing the effect of rimonabant (cannabinoid CB 1 receptor antagonist) on the effect of 6-week feeding of 5% krill solid diet on the freezing response of mice in a fear conditioning experiment; each group consisted of 10 animals; the vertical axis represents the freezing time in a 3-min period; all values refer to mean±standard error; NS indicates the absence of any significant difference; and ** indicates the presence of a significant difference at $P<0.01$.

No significant difference was observed between the rimonabant-administered krill oil group and the solvent-administered control group. Administration of the solvent caused a significant shortening of the freezing time in the krill oil group as compared with the control group (FIG. 12). These results suggested the exertion of the krill oil's action via the cannabinoid signal.

Test Example 12

Effect of μ-Opioid Receptor Antagonist on the Fear Memory Alleviating Action of Krill Oil It has also been reported of the above-mentioned rimonabant that it has a μ-opioid receptor antagonistic action as well as the cannabinoid receptor blocking action. Hence, in order to confirm that the action of krill oil is exerted via the cannabinoid signal, the present inventors performed a fear conditioning test using the μ-opioid receptor antagonist naloxone. A control group and a group fed on the 5% krill oil diet for 6 weeks were administered naloxone or a solvent 30 minutes before fear conditioning.

Results

Figure 13:
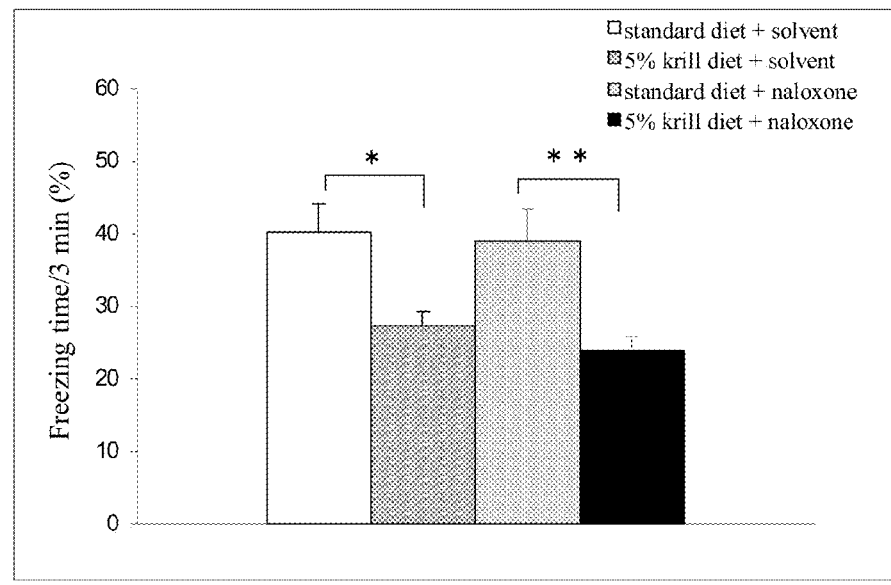
FIG. 13 is a graph showing the effect of naloxone (μ-opioid receptor antagonist) on the effect of 6-week feeding of 5% krill solid diet on the freezing response of mice in a fear conditioning experiment; each group consisted of 10 animals; the vertical axis represents the freezing time in a 3-min period; all values refer to mean±standard error; and * indicates the presence of a significant difference ($P<0.05$) between the control group and the krill oil group and between the naloxone administered control group and the naloxone administered krill oil group.

There was no difference in freezing time between the naloxone-administered krill oil group and the solvent-administered hill group (FIG. 13). Administration of the solvent caused a significant shortening of the freezing time in the krill oil group as compared with the control group. In view of this, the action of rimonabant demonstrated in Test Example 11 presumably neutralized the action of krill oil by blocking the cannabinoid signal.

Test Example 13

The values of ω3/ω6 ratio, DHA/AA ratio, and EPA/AA ratio as calculated from the fatty acid composition of diet, serum, cerebral cortex, and hippocampus in the foregoing animal experiments, as well as the relative values of freezing time in the fear conditioning tests (with respect to the freezing time in the control group which was taken as 1) were plotted to construct correlation diagrams. The values of ω3/ω6 ratio were calculated from the relative values (Area %) in each Test Example and essentially the same values would be obtained by calculation from the quantified values of fatty acids (μg/ml).

Results

Figures 1, 14:
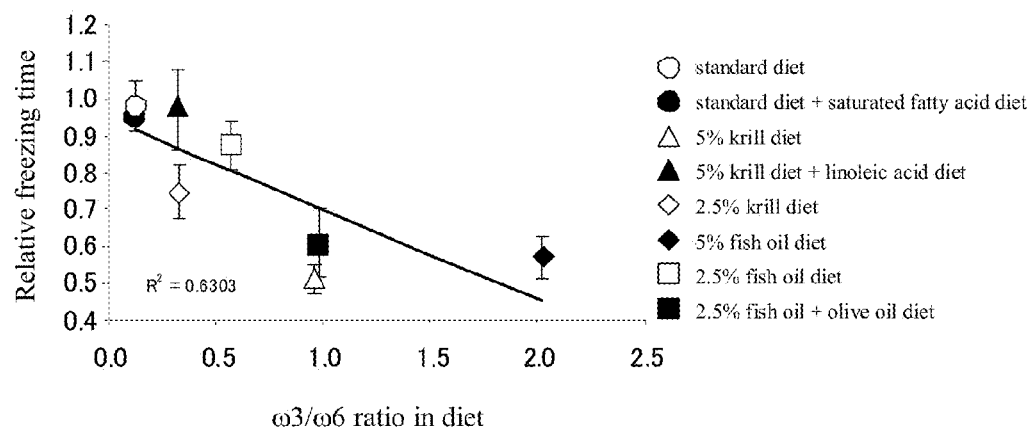
Figures 2, 14:
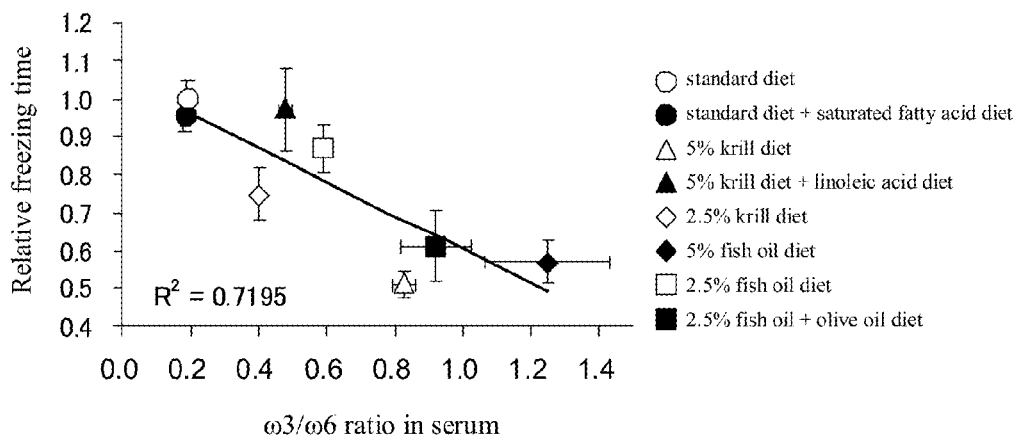
Figures 3, 14:
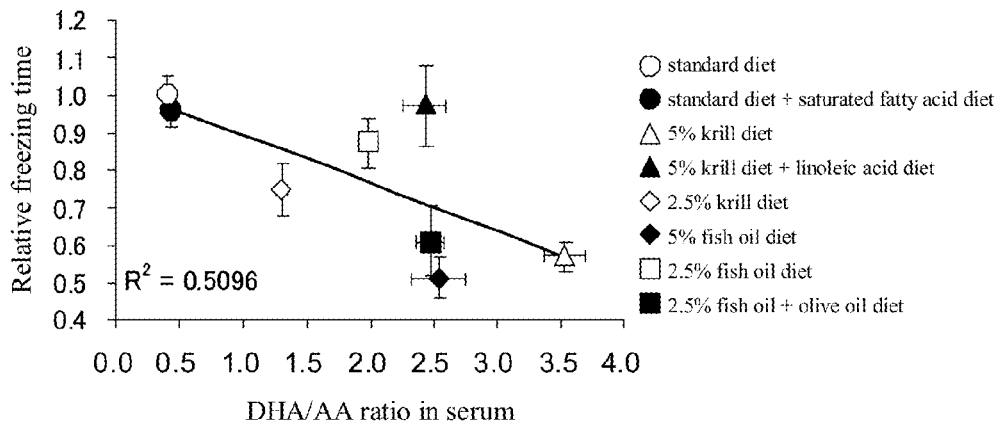
Figures 4, 14:
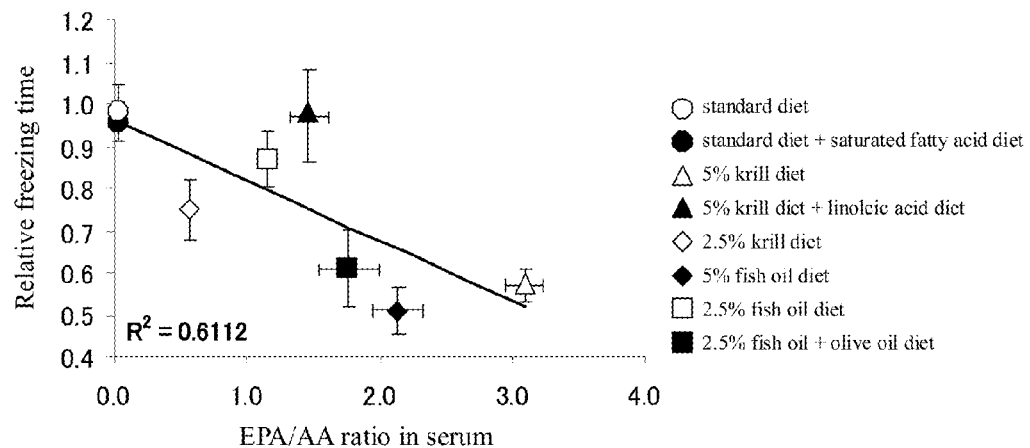
Figures 5, 14:
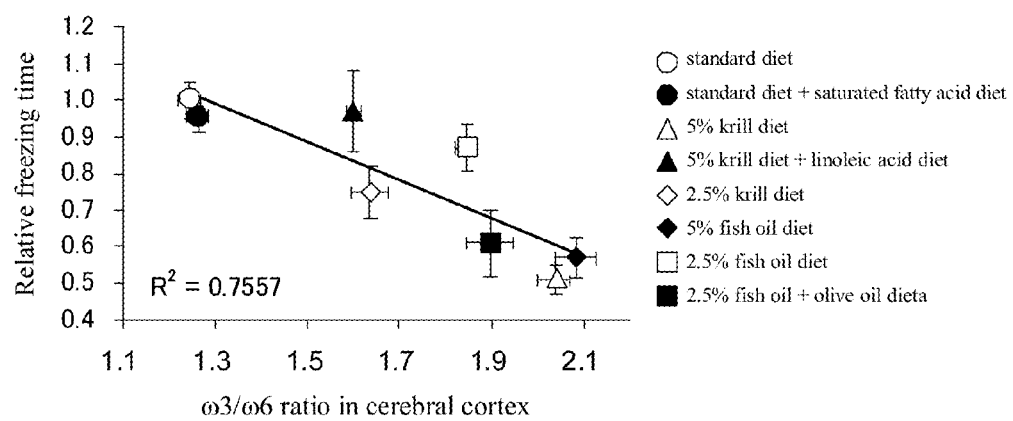
Figures 6, 14:
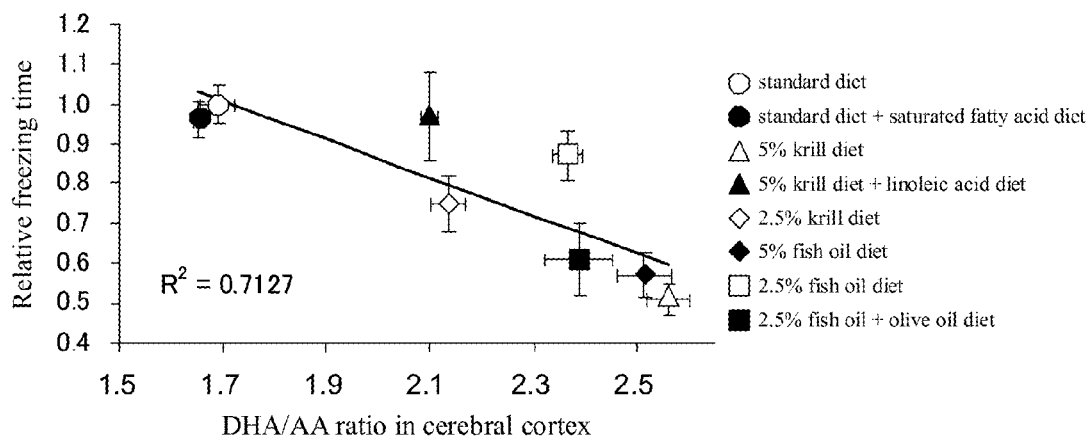
Figures 7, 14:
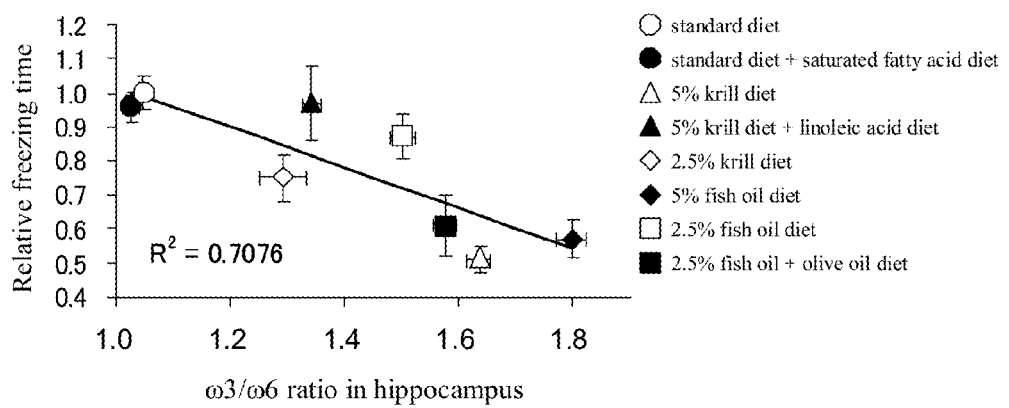
Figures 8, 14:
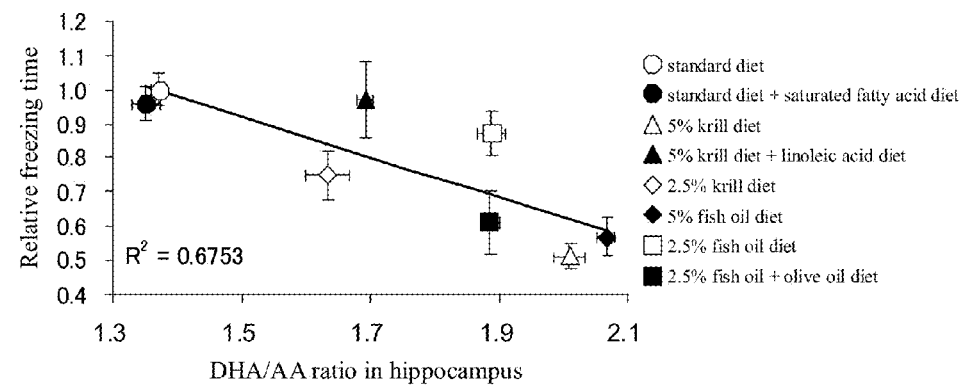

High degrees of correlation (as indicated by the square of correlation coefficient R in the diagrams) were noted in all cases (FIGS. 14-1 to 14-8), so the ω3/ω6 ratio in serum was expected to be effective as a marker for determining the risk of suffering a fear memory associated disorder. From its correlation with the ω3/ω6 ratio in diet, the ω3/ω6 ratio in serum was also expected to be promising in alimentary therapy for the treatment of anxiety disorders.

Test Example 14

Electrophysiological Study 1 in Brain Slices Using the Patch-Clamp Method

Since the fear memory alleviating action of the 5% krill diet was suppressed by the cannabinoid receptor inverse agonist rimonabant in Test Example 11, ingestion of the 5% krill diet might have changed the modification of cannabinoid-dependent synaptic transmission in the brain. In this connection, it is known that endocannabinoid is postsynaptically produced as triggered by depolarization and released into the synaptic cleft, where it acts as a retrograde signal on the presynaptic cannabinoid receptor and suppresses excitatory synaptic transmission (depolarization-induced suppression of excitation (DSE)) (Non-Patent Document 22.) Hence, in Test Example 14, the present inventors studied the above-mentioned possibility by applying the whole-cell patch-clamp method to neurons in the amygdala which plays an important role in the processing of fear memory.

Patch-clamp recordings from pyramidal cells in the amygdala were taken in accordance with the methods described in Non-Patent Documents 21 and 22. Mice were fed on the standard diet or the 5% krill diet for 6 weeks and, thereafter, the brain was taken out of mice fed on the standard diet and mice fed on the 5% krill diet, and sliced brain specimens including the amygdala were prepared using a slice preparing apparatus (VIBRATOME 3000, Vibratome, St Louis, Mo.) in a 95% $O_2$/5% $CO_2$ saturated, cooled artificial cerebrospinal fluid (124 mM NaCl, 3 mM KCl, 2 mM $CaCl_2$, 1.2 mM $KH_2PO_4$, 1.3 mM $MgSO_4$, 26 mM $NaHCO_3$, 10 mM glucose, pH 7.35, 295 mosM) (Non-Patent Documents 20 and 21.) The patch electrode (with a resistance of 4-7 MΩ) had been filled with an internal fluid of the following composition (132 mM K-gluconate, 3 mM KCl, 10 mM HEPES, 0.5 mM EGTA, 1 mM $MgCl_2$, 12 mM sodium phosphocreatine, 3 mM ATP magnesium salt, 0.5 mM GTP, pH 7.4, with KOH, 285-290 mOsm/l.) Electrophysiological signals were amplified with a patch-clamp amplifier (Multiclamp 700B (Axon Instruments, Union City, Calif., USA)) and, after passage through a 5 kHz filter, A/D converted at 50 kHz and loaded into a computer by Clampex software (ver. 9.2, Axon Instruments.) The access resistance was 7-18 MΩ. The access resistance was frequently checked during recording and any cells that experienced substantial changes (±20%) in its value during recording were excluded from analysis.

Whole-cell patch recordings were taken from pyramidal cells in the basolateral nucleus of amygdala. A bipolar glass electrode filled with an artificial cerebrospinal fluid was placed in the vicinity of the cell to be recorded and an electric stimulus was applied to the slice. First, the evoked excitatory postsynaptic current (eEPSC) was recorded from neurons in the amygdala. Subsequently, the cell being recorded was depolarized for 10 seconds and, immediately thereafter, eEPSC was recorded again. The ratio of the amplitude of eEPSC after depolarization ($I_{post}$) to that of EPSC before depolarization ($I_{pre}$) ($I_{post}/I_{pre}$) was calculated, and was used to assess the degree of DSE. In addition, to confirm the cannabinoid receptor dependency of DSE, recording was conducted with a brain slice immersed in an artificial cerebrospinal fluid containing rimonabant (5 mM). It has been suggested that DSE is attenuated by a capsaicin receptor mediated mechanism. Thus, DSE was recorded in a brain slice immersed in an artificial cerebrospinal fluid containing capsaicin (10 mM) and the resulting changes were also studied.

Results

In the amygdala of the mice fed on the 5% krill diet, the degree of DSE was significantly potentiated in comparison with the mice fed on the standard diet (FIG. 15.) Rimonabant suppressed DSE almost completely in both groups of mice. Capsaicin was also found to suppress DSE in both groups of mice (FIG. 15.)

Test Example 15

Electrophysiological Study 2 in Brain Slices Using the Patch-Clamp Method

From the results of Test Example 14, it was suggested that excitation of the neural circuits in the amygdale was lowered due to potentiation of DSE in the amygdala of the mice fed on the 5% krill diet.

It is known that the activity of the excitatory neural circuits in the amygdala is potentiated by fear conditioning (Non-Patent Document 23.) Hence, in this test, mice fed on the standard diet or the 5% krill diet for 6 weeks as in Test Example 14 were studied for changes in the input-output relation of eEPSC with or without fear conditioning. Whole-cell patch recordings were taken by essentially the same method as in Test Example X. The intensity of an eEPSC evoking electric stimulus was increased from 1 V to 10 V and the peak value of the amplitude of eEPSC as evoked at each stimulus intensity was recorded.

Results

Figure 16:
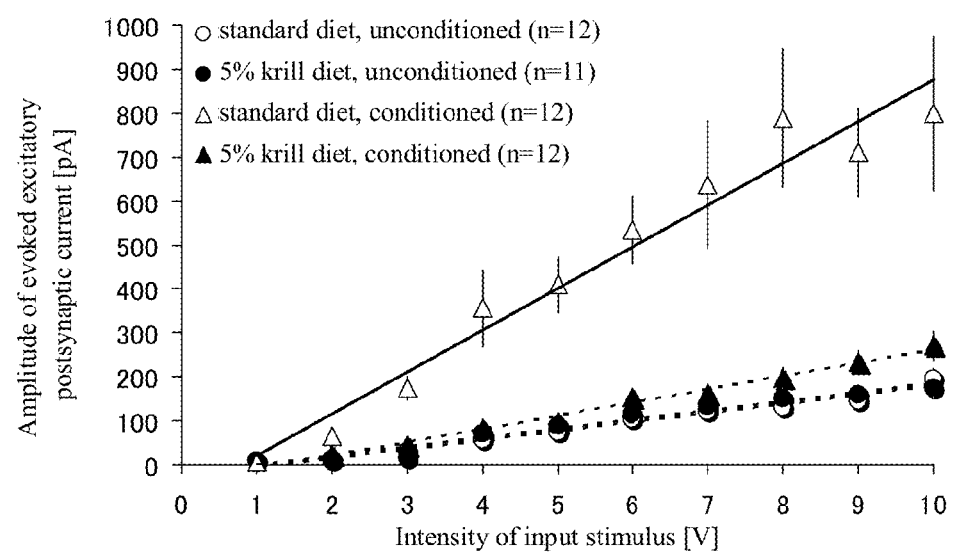
FIG. 16 is a graph showing the attenuation in the amplitude of excitatory postsynaptic currents from pyramidal cells in the amygdala; all values refer to mean±standard error.

FIG. 16 is a plot of the magnitude of eEPSC amplitude vs the intensity of input stimulus (input-output relation.) In the conditioned, standard diet fed mice, the slope of the curve describing the input-output relation of eEPSC markedly increased in comparison with the unconditioned mice. On the other hand, in the 5% krill diet fed mice, the slope of the curve describing the input-output relation of eEPSC did not show any statistically significant change whether conditioning was performed or not. It was therefore suggested that the activity of excitatory neural circuits might have been lowered in the amygdala of the 5% hill diet fed mice.

In view of these results, the attenuation of fear memory as observed in the 5% hill diet fed mice might be attributable to the lowered excitation of the amygdala due to the potentiation of cannabinoid receptor dependent DSE in the amygdala.

Considering the foregoing test results, the present inventors speculated that as a result of the DHA/AA ratio or ω3/ω6 ratio in the brain shifting toward the ω3 side, the cannabinoid signaling system in the brain would be enhanced to cause a display of the fear memory alleviating action or anxiety disorder alleviating action. This leads to the expectation that by adjusting the ω3/ω6 ratio in meals to appropriate values, the DHA/AA ratio or ω3/ω6 ratio in the brain can be controlled, and a higher value of the ratio might help prevent or treat anxiety disorders.

The invention claimed is:

1. A method of treating a human suffering from post-traumatic stress disorder comprising administering to said human a therapeutically effective amount of krill oil to treat the post-traumatic stress disorder in said human.

2. The method according to claim 1, wherein the krill oil is purified via a thermal coagulum of said krill oil.

3. The method according to claim 1, wherein the krill oil has a phospholipid content of at least 30 wt %.

4. The method according to claim 1, wherein the krill oil contains at least 15% of n-3polyunsaturated fatty acid.

5. The method according to claim 1, wherein the krill oil contains at least 10% of eicosapentaenoic acid.

6. The method according to claim 1, wherein the krill oil contains at least 5% docosahexaenoic acid.

7. The method according to claim 1, wherein the krill oil is administered at a dose of 50-5000 mg/50 kg body weight/day.

8. The method according to claim 1, wherein the krill oil is administered as an ingredient of a pharmaceutical composition.

9. The method according to claim 1, wherein the krill oil is administered as an ingredient of a food or beverage.

10. The method according to claim 1, wherein the krill oil is administered as an ingredient of a food or beverage for an emergency food in disaster or as a field ration.

11. The method according to claim 10, wherein the food or beverage is in a container or package for long storage.

* * * * *

UNITED STATES PATENT AND TRADEMARK OFFICE
CERTIFICATE OF CORRECTION

PATENT NO.       : 9,107,891 B2                    Page 1 of 1
APPLICATION NO.  : 14/129794
DATED            : August 18, 2015
INVENTOR(S)      : Masayuki Sekiguchi et al.

It is certified that error appears in the above-identified patent and that said Letters Patent is hereby corrected as shown below:

In the Claims:

Column 58, Claim 2, Line 24

Delete "a thermal coagulum of said krill oil." and insert -- "a thermal coagulum of krill" --

Signed and Sealed this
Fifteenth Day of March, 2016

Michelle K. Lee
*Director of the United States Patent and Trademark Office*